United States Patent [19]
Bitonti et al.

[11] Patent Number: 5,877,202
[45] Date of Patent: Mar. 2, 1999

[54] INDOLE DERIVATIVES USEFUL TO TREAT ESTROGEN-RELATED NEOPLASMS AND DISORDERS

[76] Inventors: Alan J. Bitonti, 8204 Mariner La., Maineville, Ohio 45039; Ian A. McDonald, 4722 Shadwell Pl., San Diego, Calif. 92130; Francesco G. Salituro, 25 Baker Dr., Marlborough, Mass. 01752; Jeffrey P. Whitten, 4966 Gunston Ct., San Diego, Calif. 92130; Esa T. Jarvi, 7924 Jolain Dr., Cincinnati, Ohio 45242; Paul S. Wright, 9332 Hunters Creek Dr., Cincinnati, Ohio 45242

[21] Appl. No.: 594,505

[22] Filed: Jan. 31, 1996

Related U.S. Application Data

[63] Continuation of Ser. No. 362,046, Dec. 22, 1994, abandoned, which is a continuation-in-part of Ser. No. 200,057, Feb. 22, 1994, abandoned.

[51] Int. Cl.$^6$ .......................... A61K 31/40; C07D 209/14
[52] U.S. Cl. .......................... 514/419; 548/493; 548/494; 548/500
[58] Field of Search ..................... 548/493, 500, 548/494; 514/419

[56] References Cited

FOREIGN PATENT DOCUMENTS

| 650261 | 10/1991 | Australia . |
|---|---|---|
| 0431520 | 12/1991 | European Pat. Off. . |
| 0693567 | 2/1995 | European Pat. Off. . |
| 1124972 | 8/1968 | United Kingdom . |
| 1124973 | 8/1968 | United Kingdom . |
| 9113874 | 9/1991 | WIPO . |
| 9214709 | 9/1992 | WIPO . |
| 9323374 | 11/1993 | WIPO . |

OTHER PUBLICATIONS

Dauvois, et al., Proc. Natl. Acad. Sci. USA, vol.89, pp. 4037–4041 (1992).

Bowler, et al., Steroids 54/1, pp. 71–99 (1989).

Mueller, Estrogen/Anti–estrogen Action and Breast Camcer Therapy, Ed. V. Craig Jordan, The Univ. of Wisconsin Press, pp. 3–17 (1986).

Rastogi et al., Research Communications in Chemical Pathology and Pharmacology, pp. 763–770 (1974).

von Angerer et al., J.Med.Chem. vol.26, pp. 112–116 (1963).

Wieland et al., Justus Liebigs Ann. Chem. vol. 591, pp. 192–199 (1955).

Kozikowski et al., J. Med. Chem. 36, pp. 2908–2920 (1993).

Thyagarajan et al., Tetrahedron Letters No. 23, pp. 1999–2002 (1974).

E. von Angerer et al., J. Med. Chem, 30, pp. 131–136 (1987).

E. von Angerer et al., J. Med. Chem, 27, pp. 1439–1447 (1984).

S.E. Fawell et al., Proc. Natl. Acad. Sci. USA, vol.87, pp. 6883–6887 (1990).

E. von Angerer et al., Eur. J. Cancer and Clin. Oncol. vol. 21, No. 4, pp. 531–537 (1985).

E. von Angerer et al, J. Med. Chem, 33, 2635–2640 (1990).

*Primary Examiner*—Johann Richter
*Assistant Examiner*—Laura Cross Lutz

[57] ABSTRACT

The present invention relates to novel indole derivatives useful in down-regulating estrogen receptor expression. Also included are methods for the treatment of neoplasms or of controlling the growth of a neoplasm in a patient afflicted with a neoplastic disease, especially estrogen-dependent neoplasms such as those associated with breast, ovarian and cervical tissue. Another embodiment of the present invention is a method of prophylactically treating a patient at risk of developing a neoplastic disease state. Also provided is a method for treating autoimmune diseases. Also included are pharmaceutical compositions of the novel indole derivatives.

72 Claims, No Drawings

INDOLE DERIVATIVES USEFUL TO TREAT ESTROGEN-RELATED NEOPLASMS AND DISORDERS

CROSS-REFERENCE TO RELATED APPLICATION

This is a continuation of application Ser. No. 08/362,046, filed Dec. 22, 1994 now abandoned, which is a continuation-in-part of application Ser. No. 08/200,057, filed Feb. 22, 1994, now abandoned, which is herein incorporated by reference.

BACKGROUND

The present invention relates to novel indole derivatives useful to down-regulate estrogen receptor expression and to treat neoplasms, especially estrogen-dependent neoplasms such as those associated with breast, ovarian, uterine and cervical tissue, and other disorders associated with estrogen activation.

The present invention provides novel indole derivatives compound of the formula

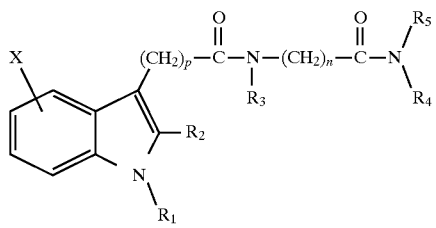

wherein n is an integer from 1 to 12;

P is 0 or 1;

X is from 1 to 3 substituents independently selected from the group consisting of hydrogen, halogen, hydroxy, $C_1$–$C_4$ alkyl, $C_1$–$C_4$ alkoxy and —OC(O)$R_6$;

$R_1$ is hydrogen, $C_1$–$C_4$ alkyl, or a radical chosen from the group consisting of

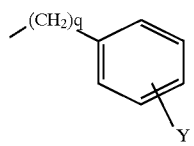

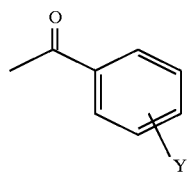

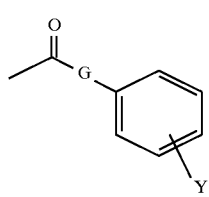

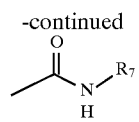

wherein q is 1, 2, 3, or 4;

Y is each time taken from 1 to 3 substituents independently selected from the group consisting of hydrogen, halogen, hydroxy, $C_1$–$C_4$ alkyl, $C_1$–$C_4$ alkoxy, and —OC(O)$R_6$;

G is —NH— or —(CH$_2$)$_r$— wherein r is 1, 2, or 3;

$R_7$ is $C_1$–$C_6$ alkyl;

$R_2$ is hydrogen, $C_1$–$C_4$ alkyl, or the radical

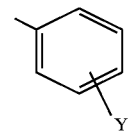

$R_3$ is hydrogen or $C_1$–$C_4$ alkyl;

$R_4$ is hydrogen or $C_1$–$C_4$ alkyl;

$R_5$ is hydrogen, $C_1$–$C_8$ alkyl, or phenyl; or $R_4$ and $R_5$ may be taken together with the adjacent nitrogen to form a ring —CH$_2$—CH$_2$—G$_1$—CH$_2$—CH$_2$— wherein G$_1$ is a direct bond, —NCH$_3$—, —CH$_2$—, or —O—; and $R_6$ is each time taken is independently selected from the group consisting of $C_1$–$C_4$ alkyl, phenyl and substituted phenyl having from 1 to 3 substituents independently selected from the group consisting of hydrogen, halogen, hydroxy, $C_1$–$C_4$ alkyl, or $C_1$–$C_4$ alkoxy;

with the proviso that when n is 1 then at least one $R_1$, $R_2$, $R_3$, $R_4$, and $R_5$ is not hydrogen;

or their pharmaceutically acceptable salts.

The present invention includes methods to treat neoplasms or of controlling the growth of a neoplasm in a patient afflicted with a neoplastic disease comprising administration of a compound of formula provided.

Another embodiment of the present invention is a method of prophylactically treating a patient at risk of developing a neoplastic disease state comprising administration of a compound of the formula provided.

Breast cancer is the leading cause of cancer among women and the second biggest killer of women. The age-adjusted incidence rate for breast cancer among women in the United States between 1986 and 1987 was 108.9 per 100,000. This is over two times greater than the age-adjusted incidence rate for cancer of the colon, the second leading form of cancer in women. Satariano, W. A., Aging, Comorbidity, and Breast Cancer Survival: An Epidemiologic View. in *The Underlying Molecular, Cellular, and Immunological Factors in Cancer and Aging*, (Young, S. S. and Warner, H. R., eds.) Plenum Press, New York, pp. 1–11, 1993.

In women, the risk of developing breast cancer increases dramatically with age (Pike et al., "The epidemiology of breast cancer as it relates to menarche pregnancy and menopause." in *Banbury Report 8: Hormones and Breast Cancer* (Pike, M. C., Siiteri, P. K. and Welsch, C. W., eds.), Cold Spring Harbor Laboratory, pp. 3–21, 1981). The risk of a woman developing breast cancer by age 30 is about one in 2,500. The risk of a woman developing breast cancer by age 60 is one in 24. Although significant advances have been made regarding the treatment options for those with breast cancer, the mortality rate for breast cancer remains high.

The difference of incidence of breast cancer among pre- and post-menopausal women suggests exposure to estrogen is critical to onset and malignant progression of breast cancer. This conclusion is strengthened by comparing the incidence of breast cancer in women and men; women develop breast cancer about 100 times the frequency of men. Ovariectomy and/or antiestrogenic and antiprogestational drugs have been successfully used in treatment of breast cancer (Iino, Y. et al., Antiestrogen therapy for breast cancer: Current strategies and potential causes for therapeutic failure, in: *Regulatory Mechanisms in Breast Cancer*, Lippman, M. E. and Dickson, R. B., eds., Klower Academic Publishers, Norwell, Mass., pp. 221–238, 1990).

The steroid dependence of some breast cancers has been known for almost 100 years and both endocrine therapy and surgery (ovariectomy/adrenalectromy) have been used for the control of this disease. Steroid dependence has been explained by varying estrogen receptor levels in breast tumors. Of those tumors possessing detectable estrogen receptor, determined by cytosols containing greater than ten fmol of estrogen receptor per mg of protein, over 60% have proved to be responsive to endocrine therapy, whereas those containing less than ten fmol of receptor per mg of protein, less than 5% have responded.

Estrogens are thought to regulate the growth of tumor cells via estrogen receptors (ERs) present in the cytosol. ERs are "activated" upon binding with ligands such as estradiol and estrogen. Once bound, the estrogen-estrogen receptor complex migrates through the cytosol and into the nucleus, where the complex is thought to initiate the transcription of other proteins. The binding of estrogen to the estrogen receptor exposes groups which enable the complex to form tight complexes with both acidic and basic macromolecules such as DNA, acidic polysaccharides, histones and other basic proteins. After binding, a series of events follows, including dissociation from heat shock proteins, dimerization and binding to DNA at an estrogen response element (ERE). After binding to the DNA, the activated estrogen-ER complex is thought to interact with transcription factors and stabilize preinitiation complex at the promoter, allowing RNA polymerase to initiate gene transcription and resulting in transcription of mRNA. Subsequent steps in the transformation of normal cells to tumor cells has yet to be elucidated; but prevention of estrogen activation of breast cells is thought to prevent subsequent development of uncontrolled cellular growth resulting from estrogen-activated transcription.

Many of the receptors for virtually all relevant steroid hormones have been cloned and sequenced. As a result, it has been discovered that the steroid hormone receptors belong to a large superfamily of nuclear receptors, that includes the receptors for retinoic acid, thyroid hormones and several genes for which a physiological ligand is as of yet not know, designated "orphan" receptors.

Common to all members of the nuclear receptor family is a short DNA-binding domain composed of about 70 amino acid residues containing many conserved cysteines. Eight of these conserved cysteines can be organized into two so-called "zinc" fingers, a structure first proposed for the transcription factor FTIIIA from *Xenopus laevis*. Each zinc finger contains four cysteine residues tetrahedrally coordinating a zinc ion.

Based on sequence conservation of the two zinc "fingers", each of which is encoded by a separate exon, the nuclear receptor genes have been classified into two subfamilies. The glucocorticoid receptor (GR) is the prototype of the smaller subfamily that includes the progesterone receptor (PR), androgen receptor and the mineralocorticoid receptor. The prototype of the larger subfamily is the estrogen receptor (ER) and this group includes the vitamin $D_3$ receptor, the various thyroid hormone receptors, the receptors for retinoic acid and many of the orphan receptors.

ER has been characterized as having two activation domains, referred to as TAF1 (located at the amino terminus of the receptor) and TAF2 (located in the 60 amino acid-carboxyl terminus). TAF1 activation is estrogen independent; once delivered to DNA it can activate transcription. Studies on human ER mutants have demonstrated that the action of TAF1 and TAF2 depends on the promoter context; on certain promoters, both the TAF1 and TAF2 activations are required for transcriptional activity. On other promoters, the TAF1 and TAF2 activators function independently.

Significant research has been conducted on estrogen agonists and antagonists useful to treat neoplasms associated with the breast. The antiestrogen tamoxifen is widely used in the endocrine therapy of hormone-dependent breast cancer. About 40% of the patients do not respond to tamoxifen treatment despite the presence of ERs in the malignant tissue. Maass, H., et al., *Cancer*, 46:2783 (1980). One possible reason for failure may be due to the weak estrogenic activity of tamoxifen or due to the incomplete antagonism of tamoxifen. The antagonist activity of tamoxifen is thought to arise from its intrinsic inability to activate the TAF2 function of the estrogen receptor. Tzukerman, M. T., et al., *Mol. Endocrin.*, 8(1):21–30 (1994). However, toxicological problems associated with tamoxifen treatment, including tumor flares, vaginal cornification and hypercalciemia, make long term tamoxifen treatment undesirable in some situations. In addition, some tumors are tamoxifen-resistant despite the existence of estrogen receptors. Therefore, there is a need for a better method of treating estrogen-dependent neoplasms.

In an effort to develop "pure" antiestrogen drugs, researchers investigated estrogen-like compounds. One of the earliest was ICI 164,384 (11-(3-17β-dihydroxyoestra-1, 3,-5(10)-trien-7α-yl)-N-n-butyl-N-methylundecanamide). ICI 164,384 has been shown to inhibit DNA binding of the mouse estrogen receptor by interfering with receptor dimerization. Fawell, S. E., et al., *Proc. Nat'l. Acad. Sci. USA*, 87:6883–6887 (1990). Von Angerer and his colleagues have developed derivatives of 2-phenylindole with an aminoalkyl chain at the indole nitrogen. Von Angerer, E., et al., *J. Med. Chem.* 1990, 33, 2635–2640. These 1-(amino-alkyl)-2-phenylindoles are estrogen antagonists and were thought to avoid the problems associated with the estrogenic activity of tamoxifen.

The statistics of incidence of breast cancer in men and women, pre and postmenopausal, indicates that exposure of the mammary gland to ovarian estrogens and progestins is critical to onset and malignant progression of breast cancer. Other growth regulatory mechanisms may also play a role in the loss of ovarian function during menopause and may also play a role in the onset of breast cancer. Furthermore, a genetic factor(s), inherited familial autosomal dominant genes, are also thought to influence the risk of breast cancer.

ERs are widely distributed throughout the body in organ tissues associated with female reproduction, e.g., vagina, cervix, corpus uteri, fallopian tubes, ovaries and breast. The presence of ERs are not limited to cells in female reproductive organs; ERs are also found in cells throughout the body, including the uterus [(Quarmby, V. E., et al., *Endocrin.*, 114:694–702 (1984)], bone [Yamamoto, T. T., et al, *Proc.*

Natl. Acad. Sci. USA, 48:2172–2176 (1990); Migliaccio, S. et al., Endocrin., 130:1756–1758 (1992); Eriksen E. F., et al, Science, 241:84–86 (1988)], kidney [Davidoff, M., et al., Histochem., 9:39–48 (1980)], and brain [Fox, T. O., Nature, 258:441–443 (1975)]. As of yet, the understanding of the role these ERs play in normal and disease states is not well defined. Given the pleotrophic effect estrogen is known to have on cells, it is logical to expect that gene transcription resulting from activation of ERs contributes uncontrolled cell growth (neoplasia) and/or cellular dysfunction in ER-expressing cells.

Heightened estrogen activity may play a role in the symptoms associated with a number of seemingly unrelated diseases. Autoimmune diseases appear to be due to the failure of normal mechanisms of self-tolerance. Some autoimmune diseases involve an immune response against self-molecules that are expressed in anatomically remote sites; others are due to immune responses to ubiquitous nuclear and cytomplasmic antigens. Human autoimmune diseases have been classified in several ways; many have been linked to genes encoding the major histocompatibilty complex (MHC), class I or class II. Susceptibility to autoimmune diseases is also associated with environmental factors, such as preceding infection, and endocrine factors. Many autoimmune diseases have a peak incidence at or shortly after puberty and a second peak incidence in the forties and fifties, ages when the endocrine system is changing. Autoimmune diseases are generally worse in women than in men, often flaring after pregnancy, and approximately two thirds of those afflicted with autoimmune diseases are women. Therefore, estrogen activity is implicated in the etiology of autoimmune diseases such as multiple sclerosis, rheumatoid arthritis, insulin-dependent diabetes, Graves' disease, myasthenia gravis, and systemic lupus erythematosus. Multiple sclerosis, rheumatoid arthritis, systemic lupus erythematosus and myasthenia gravis typically proceed with periods of deterioration and remission. The periods of deterioration correlate with female hormones, stress and infection. An explanation for these observations may be that estrogen activation of the estrogen receptor results in gene transcription of the nearby gene encoding gamma-interferon, which aggravates the autoimmune process. Therefore, prevention of estrogen-induced transcription would be expected to alleviate or even prevent the symptoms of such diseases.

SUMMARY OF THE INVENTION

The present invention provides novel indoles of the formula

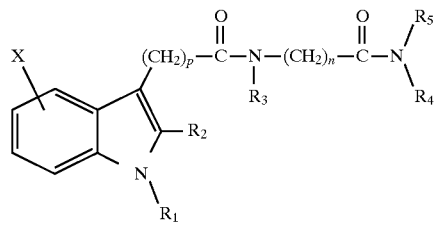

wherein n is an integer from 1 to 12;

P is 0 or 1;

X is from 1 to 3 substituents independently selected from the group consisting of hydrogen, halogen, hydroxy, $C_1$–$C_4$ alkyl, $C_1$–$C_4$ alkoxy and —OC(O)$R_6$;

$R_1$ is hydrogen, $C_1$–$C_4$ alkyl, or a radical chosen from the group consisting of

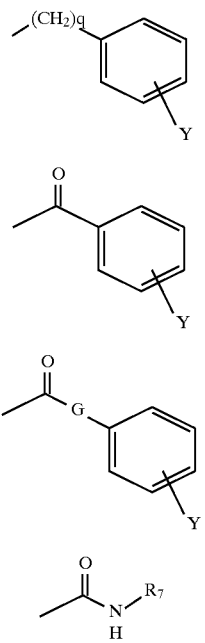

wherein q is 1, 2, 3, or 4;

Y is each time taken from 1 to 3 substituents independently selected from the group consisting of hydrogen, halogen, hydroxy, $C_1$–$C_4$ alkyl, $C_1$–$C_4$ alkoxy, and —OC(O)$R_6$;

G is —NH— or —(CH$_2$)$_r$— wherein r is 1, 2, or 3;

$R_7$ is $C_1$–$C_6$ alkyl;

$R_2$ is hydrogen, $C_1$–$C_4$ alkyl, or the radical

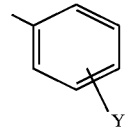

$R_3$ is hydrogen or $C_1$–$C_4$ alkyl;

$R_4$ is hydrogen or $C_1$–$C_4$ alkyl;

$R_5$ is hydrogen, $C_1$–$C_8$ alkyl, or phenyl; or $R_4$ and $R_5$ may be taken together with the adjacent nitrogen to form a ring —CH$_2$—CH$_2$—G$_1$—CH$_2$—CH$_2$— wherein G$_1$ is a direct bond, —NCH$_3$—, —CH$_2$—, or —O—; and $R_6$ is each time taken is independently selected from the group consisting of $C_1$–$C_4$ alkyl, phenyl and substituted phenyl having from 1 to 3 substituents independently selected from the group consisting of hydrogen, halogen, hydroxy, $C_1$–$C_4$ alkyl, or $C_1$–$C_4$ alkoxy;

with the proviso that when n is 1 then at least one $R_1$, $R_2$, $R_3$, $R_4$, and $R_5$ is not hydrogen;

or their pharmaceutically acceptable salts.

The present invention relates to pharmaceutical compositions comprising novel indoles. Also presented are methods to down-regulate expression of ERs and prevent estrogen-dependent transcription. The present invention also relates to methods to treat neoplasms, particularly estrogen-dependent neoplasms associated with breast, uterine and cervical tissue and other estrogen-dependent disorders, including autoimmune diseases.

DETAILED DESCRIPTION OF THE INVENTION

As used herein:

a) the term "$C_1$–$C_4$ alkyl" refers to a saturated straight or branched chain hydrocarbyl radical of from one to four carbon atoms and includes methyl, ethyl, propyl, isopropyl, n-butyl, isobutyl, and tertiary butyl;

b) the term "$C_1$–$C_8$ alkyl" refers to saturated straight or branched chain hydrocarbyl radicals of one to eight, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like;

c) the term "halogen", "halo", "halide", or "Hal" refers to fluorine atom, chlorine atom, bromine atom, or iodine atom;

d) the term "$C_1$–$C_4$ alkoxy" refers to a straight or branched alkoxy group containing from one to four carbon atoms, such as methoxy, ethoxy, n-propoxy, isopropoxy, n-butoxy, isobutoxy, t-butoxy, and the like;

e) the designation "—C(O)—" refers to a carbonyl group of the formula:

f) the term "phenyl" refers to

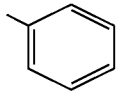

g) the term "substituted phenyl" refers to

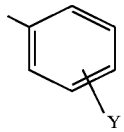

wherein

Y is from 1 to 3 substituents independently chosen from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$ alkyl, phenyl or substituted phenyl having from 1 to 3 substituents independently selected from the group consisting of hydrogen, halogen, hydroxy, $C_1$–$C_4$ alkyl, or $C_1$–$C_4$ alkoxy;

h) the term "benzyl" refers to

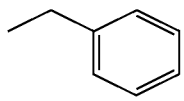

i) the term "substituted benzyl" refers to

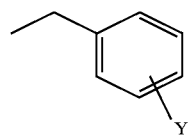

wherein

Y is from 1 to 3 substituents independently chosen from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$ alkyl, phenyl or substituted phenyl having from 1 to 3 substituents independently selected from the group consisting of hydrogen, halogen, hydroxy, $C_1$–$C_4$ alkyl, or $C_1$–$C_4$ alkoxy;

j) the term "benzoyl" refers to

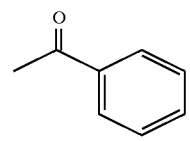

k) the term "substituted benzoyl" refers to

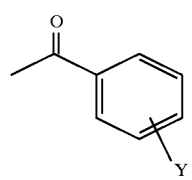

wherein

Y is from 1 to 3 substituents independently selected from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$ alkyl, phenyl or substituted phenyl having from 1 to 3 substituents independently selected from the group consisting of hydrogen, halogen, hydroxy, $C_1$–$C_4$ alkyl, or $C_1$–$C_4$ alkoxy;

l) the term "Pg" refers to a protecting group as described in *Protecting Groups in Organic Synthesis* by T. Greene as is well known and appreciated by those skilled in the art; and m) the term "pharmaceutically acceptable salts" refers to base addition salts including any non-toxic organic or inorganic basic addition salts of a compound of the formula provided or any of its intermediates. Illustrative bases which form suitable salts include alkali metal or alkaline-earth metal hydroxides such as sodium, potassium, calcium, magnesium, or barium hydroxides; ammonia, and aliphatic, cyclic, or aromatic organic amines such as methylamine, dimethylamine, trimethylamine, triethylamine, diethylamine, isopropyldiethylamine, pyridine and picoline.

n) the term "$C_1$–$C_6$ alkyl" refers to a saturated straight or branched chain hydrocarbyl radical of from one to six carbon atoms and includes methyl, ethyl, propyl, isopropyl, n-butyl, isobutyl, tertiary butyl, pentyl, hexyl, cyclopentyl, cyclohexyl and the like;

o) the designation

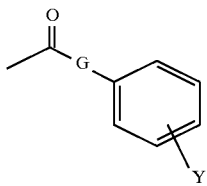

when G is —NH— refers to wherein
Y is from 1 to 3 substituents independently chosen from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$

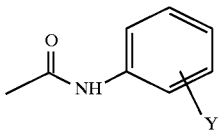

alkyl, phenyl or substituted phenyl having from 1 to 3 substituents independently selected from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$ alkyl, phenyl or substituted phenyl having from 1 to 3 substituents independently selected from the group consisting of hydrogen, halogen, hydroxy, $C_1$–$C_4$ alkyl, or $C_1$–$C_4$ alkoxy; and
when G is —(CH$_2$)$_r$— refers to

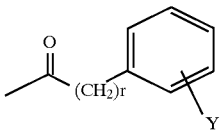

wherein
r is 1, 2, or 3; and
Y is from 1 to 3 substituents independently chosen from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$ alkyl, phenyl or substituted phenyl having from 1 to 3 substituents independently selected from the group consisting of hydrogen, halogen, hydroxy, $C_1$–$C_4$ alkyl, $C_1$–$C_4$ alkoxy, and —OC(O)$R_6$ wherein $R_6$ is $C_1$–$C_4$ alkyl, phenyl or substituted phenyl having from 1 to 3 substituents independently selected from the group consisting of hydrogen, halogen, hydroxy, $C_1$–$C_4$ alkyl, or $C_1$–$C_4$ alkoxy.

It being understood that when $R_4$ and $R_5$ are taken together with the adjacent nitrogen to form a ring —CH$_2$—CH$_2$—G$_1$—CH$_2$—CH$_2$— and G$_1$ is a direct bond the ring formed is pyrrolidine, when G$_1$ is —NCH$_3$— the ring formed is 4-methylpiperazine, when G1 is —CH$_2$— the ring formed is piperidine and when G1 is —O— the ring formed is morpholine.

It being further understood that each time a Y substituent occurs in $R_1$ or $R_2$, the Y substituent is independently selected for $R_1$ or $R_2$. It being further understood that each time $R_6$ occurs in $R_1$ or $R_2$, the $R_6$ substituent is independently selected for $R_1$ or $R_2$.

Examples of compounds encompassed by the present invention include:

8-[[5-Methoxy-1-benzoyl-2-methyl-1H-indol-3-yl]-acetylamino]-octanoic acid methyl-butyl-amide;
8-[[5-Methoxy-1-(4-chlorobenzoyl)-2-methyl-1H-indol-3-yl]-acetylamino]-octanoic acid methyl-butyl-amide;
8-[[5-Methoxy-1-methyl-2-[(4-methoxy)phenyl]-1H-indol-3-yl]-acetylamino]-octanoic acid methyl-butyl-amide;
8-[[5-Methoxy-1-benzyl-2-[(4-methoxy)phenyl]-1H-indol-3-yl]-acetylamino]-octanoic acid methyl-butyl-amide;
8-[[5-Methoxy-1-methyl-2-methyl-1H-indol-3-yl]-acetylamino]-octanoic acid methyl-butyl-amide;
8-[[5-Methoxy-1-benzyl-2-methyl-1H-indol-3-yl]-acetylamino]-octanoic acid methyl-butyl-amide;
6-[[5-Methoxy-1-benzyl-2-[(4-methoxy)phenyl]-1H-indol-3-yl]-acetylamino]-hexanoic acid methyl-butyl-amide;
8-[[5-Methoxy-1-benzyl-2-[(4-methoxy)phenyl]-1H-indol-3-yl]-acetylamino]-octanoic acid butyl-amide;
12-[[5-Chloro-1-ethyl-2-methyl-1H-indol-3-yl]-acetylamino]-dodecanoic acid methyl-butyl-amide;
8-[[5-Chloro-1-ethyl-2-methyl-1H-indol-3-yl]-acetyl-N-butylamino]-dodecanoic acid methyl-butyl-amide;
6-[[5-Chloro-1-ethyl-2-methyl-1H-indol-3-yl]-acetylamino]-hexanoic acid methyl-butyl-amide;
1-[[5-Chloro-1-ethyl-2-methyl-1H-indol-3-yl]-acetylamino]-acetic acid methyl-butyl-amide;
8-[[5-Methyl-1-[(4-methyl)benzyl]-2-methyl-1H-indol-3-yl]-acetyl-N-methylamino]-octanoic acid methyl-butyl-amide;
8-[[5-Methoxy-1-benzyl-2-methyl-1H-indol-3-yl]-acetylamino]-octanoic acid butyl-octyl-amide;
8-[[5-Methoxy-1-benzyl-2-methyl-1H-indol-3-yl]-acetylamino]-octanoic acid dimethyl-amide;
8-[[5-Methoxy-1-benzoyl-2-methyl-1H-indol-3-yl]-acetylamino]-octanoic acid methyl-amide;
8-[[5-Methoxy-1-benzyl-2-methyl-1H-indol-3-yl]-acetylamino]-octanoic acid dibutyl-amide;
5-Chloro-1-methyl-1H-indole-3-carboxylic acid [8-(butyl-methyl-carbamoyl)-octyl]-amide;
5-Methoxy-1-methyl-1H-indole-3-carboxylic acid [8-(butyl-methyl-carbamoyl)-octyl]-amide;
5-Chloro-1-benzyl-1H-indole-3-carboxylic acid [8-(butyl-methyl-carbamoyl)-octyl]-amide;
5-Methoxy-1-benzyl-1H-indole-3-carboxylic acid [8-(butyl-methyl-carbamoyl)-octyl]-amide;
1-Benzoyl-2-methyl-1H-indole-3-caboxylic acid [8-(butyl-methyl-carbamoyl)-octyl]-amide;
1-Benzoyl-2-[4-(methoxy)phenyl]-1H-indole-3-caboxylic acid [8-(butyl-methyl-carbamoyl)-octyl]-amide;
5-Chloro-1-benzyl-1H-indole-3-carboxylic acid [8-(butyl-methyl-carbamoyl)-octyl]-amide;
5-Methoxy-1-benzyl-1H-indole-3-carboxylic acid [8-(butyl-methyl-carbamoyl)-octyl]-amide;
8-[[5-Hydroxy-1-benzyl-2-methyl-1H-indol-3-yl]-acetylamino]-octanoic acid methyl-butyl-amide;
8-[[5-Hydroxy-1-benzoyl-2-methyl-1H-indol-3-yl]-acetylamino]-octanoic acid methyl-butyl-amide;
8-[[5-Hydroxy-1-(4-chlorobenzoyl)-2-methyl-1H-indol-3-yl]-acetylamino]-octanoic acid methyl-butyl-amide;
8-[[5-Hydroxy-1-benzyl-2-[(4-hydroxy)-phenyl]-1H-indol-3-yl]-acetylamino]-octanoic acid methyl-butyl-amide;
8-[[5-Hydroxy-1-methyl-2-[(4-hydroxy)-phenyl]-1H-indol-3-yl]-acetylamino]-octanoic acid methyl-butyl-amide;
6-[[5-Hydroxy-1-benzyl-2-[(4-hydroxy)phenyl]-1H-indol-3-yl]-acetylamino]-hexanoic acid methyl-butyl-amide;
8-[[5-Hydroxy-1-benzyl-2-[(4-hydroxy)phenyl]-1H-indol-3-yl]-acetylamino]-octanoic acid butyl-amide;
5-Hydroxy-1-methyl-1H-indole-3-carboxylic acid [8-(butyl-methyl-carbamoyl)-octyl]-amide;
5-Hydroxy-1-benzyl-1H-indole-3-carboxylic acid [8-(butyl-methyl-carbamoyl)-octyl]-amide;
8-[[5-Methoxy-2-methyl-1H-indol-3-yl]-acetylamino]-octanoic acid methyl-butyl-amide;

2-Methyl-1H-indole-3-caboxylic acid [8-(butyl-methyl-carbamoyl)-octyl]-amide;
2-[4-(Methoxy)phenyl]-1H-indole-3-caboxylic acid [8-(butyl-methyl-carbamoyl)-octyl]-amide;
8-[[5-Acetoxy-1-benzoyl-2-methyl-1H-indol-3-yl]-acetylamino]-octanoic acid methyl-butyl-amide;
8-[[5-Acetoxy-1-benzyl-2-methyl-1H-indol-3-yl]-acetylamino]-octanoic acid methyl-butyl-amide;
8-[[5-Acetoxy-1-(4-chlorobenzoyl)-2-methyl-1H-indol-3-yl]-acetylamino]-octanoic acid methyl-butyl-amide;
8-[[5-Acetoxy-1-benzyl-2-[(4-acetoxy)-phenyl]-1H-indol-3-yl]-acetylamino]-octanoic acid methyl-butyl-amide;
8-[[5-Acetoxy-1-benzyl-2-[(4-acetoxy)phenyl]-1H-indol-3-yl]-acetylamino]-hexanoic acid methyl-butyl-amide;
8-[[5-Acetoxy-1-benzyl-2-[(4-acetoxy)-phenyl]-1H-indol-3-yl]-acetylamino]-octanoic acid methyl-butyl-amide;
8-[[5-Benzoyloxy-1-benzyl-2-methyl-1H-indol-3-yl]-acetylamino]-octanoic acid methyl-butyl-amide;
8-[[5-Acetoxy-1-benzyl-2-[(4-hydroxy)-phenyl]-1H-indol-3-yl]-acetylamino]-octanoic acid methyl-butyl-amide;
8-[1-Benzyl-1H-indol-3-yl]-acetylamino]-octanoic acid methyl-butyl-amide;
8-[[5-Methoxy-1-(4-chlorobenzoyl)-2-methyl-1H-indol-3-yl]-acetylamino]-octanoic acid diethyl-amide;
8-[[5-Hydroxy-1-(4-chlorobenzoyl)-2-methyl-1H-indol-3-yl]-acetylamino]-octanoic acid diethyl-amide;
8-[[5-Acetoxy-1-(4-chlorobenzoyl)-2-methyl-1H-indol-3-yl]-acetylamino]-octanoic acid diethyl-amide;
8-[[5-Methoxy-1-(4-chlorobenzoyl)-2-methyl-1H-indol-3-yl]-acetylamino]-octanoic acid pyrrolidine-amide;
8-[[5-Hydroxy-1-(4-chlorobenzoyl)-2-methyl-1H-indol-3-yl]-acetylamino]-octanoic acid pyrrolidine-amide;
8-[[5-Acetoxy-1-(4-chlorobenzoyl)-2-methyl-1H-indol-3-yl]-acetylamino]-octanoic acid pyrrolidine-amide;
8-[[5-Methoxy-1-(4-methoxybenzoyl)-2-methyl-1H-indol-3-yl]-acetylamino]-octanoic acid methyl-butyl-amide;
8-[[5-Hydroxy-1-(4-methoxybenzoyl)-2-methyl-1H-indol-3-yl]-acetylamino]-octanoic acid methyl-butyl-amide;
8-[[5-Acetoxy-1-(4-methoxybenzoyl)-2-methyl-1H-indol-3-yl]-acetylamino]-octanoic acid methyl-butyl-amide;
7-[[5-Methoxy-1-benzoyl-2-methyl-1H-indol-3-yl]-acetylamino]-heptanoic acid methyl-butyl-amide;
7-[[5-Hydroxy-1-benzoyl-2-methyl-1H-indol-3-yl]-acetylamino]-heptanoic acid methyl-butyl-amide;
7-[[5-Acetoxy-1-benzoyl-2-methyl-1H-indol-3-yl]-acetylamino]-heptanoic acid methyl-butyl-amide;
7-[[5-Methoxy-1-benzoyl-2-methyl-1H-indol-3-yl]-acetylamino]-heptanoic acid methyl-phenyl-amide;
7-[[5-Hydroxy-1-benzoyl-2-methyl-1H-indol-3-yl]-acetylamino]-heptanoic acid methyl-phenyl-amide;
7-[[5-Acetoxy-1-benzoyl-2-methyl-1H-indol-3-yl]-acetylamino]-heptanoic acid methyl-phenyl-amide;
7-[[5-Methoxy-1-benzoyl-2-methyl-1H-indol-3-yl]-acetylamino]-heptanoic acid diethyl-amide;
7-[[5-Hydroxy-1-benzoyl-2-methyl-1H-indol-3-yl]-acetylamino]-heptanoic acid diethyl-amide;
7-[[5-Acetoxy-1-benzoyl-2-methyl-1H-indol-3-yl]-acetylamino]-heptanoic acid diethyl-amide;
7-[[5-Fluoro-1-benzoyl-1H-indol-3-yl]-acetylamino]-heptanoic acid diethyl-amide;
8-[[5-Fluoro-1-benzyl-1H-indol-3-yl]-acetylamino]-octanoic acid methyl-butyl-amide;
8-[[5-Methoxy-1-(3-phenylpropionyl)-2-methyl-1H-indol-3-yl]-acetylamino]-octanoic acid methyl-butyl-amide;
8-[[5-Hydroxy-1-(3-phenylpropionyl)-2-methyl-1H-indol-3-yl]-acetylamino]-octanoic acid methyl-butyl-amide;
8-[[5-Acetoxy-1-(3-phenylpropionyl)-2-methyl-1H-indol-3-yl]-acetylamino]-octanoic acid methyl-butyl-amide;
7-[[5-Methoxy-1-(3-phenylpropyl)-2-methyl-1H-indol-3-yl]-acetylamino]-heptanoic acid methyl-butyl-amide;
7-[[5-Hydroxy-1-(3-phenylpropyl)-2-methyl-1H-indol-3-yl]-acetylamino]-heptanoic acid methyl-butyl-amide;
7-[[5-Acetoxy-1-(3-phenylpropyl)-2-methyl-1H-indol-3-yl]-acetylamino]-heptanoic acid methyl-butyl-amide;
8-[[5-Methoxy-1-(4-chlorobenzoyl)-2-methyl-1H-indol-3-yl]-acetylamino]-octanoic acid morpholine-amide;
8-[[5-Hydroxy-1-(4-chlorobenzoyl)-2-methyl-1H-indol-3-yl]-acetylamino]-octanoic acid morpholine-amide;
8-[[5-Acetoxy-1-(4-chlorobenzoyl)-2-methyl-1H-indol-3-yl]-acetylamino]-octanoic acid morpholine-amide;
7-[[5-Methoxy-1-benzyl-2-[(4-methoxy)phenyl]-1H-indol-3-yl]-acetylamino]-heptanoic acid methyl butyl-amide;
7-[[5-Hydroxy-1-benzyl-2-[(4-hydroxy)phenyl]-1H-indol-3-yl]-acetylamino]-heptanoic acid methyl butyl-amide;
7-[[5-Acetoxy-1-benzyl-2-[(4-acetoxy)phenyl]-1H-indol-3-yl]-acetylamino]-heptanoic acid methyl butyl-amide;
6-[[5-Methoxy-1-(4-chlorobenzoyl)-2-methyl-1H-indol-3-yl]-acetylamino]-hexanoic acid methyl-butyl-amide;
6-[[5-Hydroxy-1-(4-chlorobenzoyl)-2-methyl-1H-indol-3-yl]-acetylamino]-hexanoic acid methyl-butyl-amide;
6-[[5-Acetoxy-1-(4-chlorobenzoyl)-2-methyl-1H-indol-3-yl]-acetylamino]-hexanoic acid methyl-butyl-amide;
8-[[5-Methoxy-1-benzyl-2-(4-fluorophenyl)-1H-ind;ol-3-yl]-acetylamino]-octanoic acid methyl-butyl-amide;
8-[[5-Hydroxy-1-benzyl-2-(4-fluorophenyl)-1H-indol-3-yl]-acetylamino]-octanoic acid methyl-butyl-amide;
8-[[5-Acetoxy-1-benzyl-2-(4-fluorophenyl)-1H-indol-3-yl]-acetylamino]-octanoic acid methyl-butyl-amide;
6-[[5-Methoxy-1-benzyl-2-[(4-methoxy)phenyl]-1H-indol-3-yl]-acetylamino]-hexanoic acid methyl-butyl-amide;
6-[[5-Hydroxy-1-benzyl-2-[(4-hydroxy)phenyl]-1H-indol-3-yl]-acetylamino]-hexanoic acid methyl-butyl-amide;
6-[[5-Acetoxy-1-benzyl-2-[(4-acetoxy)phenyl]-1H-indol-3-yl]-acetylamino]-hexanoic acid methyl-butyl-amide;
7-[[5-Methoxy-1-(carboxylic acid 4-methoxyphenyl amide)-1H-indol-3-yl]-acetylamino]-heptanoic acid diethyl-amide;
7-[[5-Hydroxy-1-(carboxylic acid 4-hydroxyphenyl amide)-1H-indol-3-yl]-acetylamino]-heptanoic acid diethyl-amide;
7-[[5-Acetoxy-1-(carboxylic acid 4-acetoxyphenyl amide)-1H-indol-3-yl]-acetylamino]-heptanoic acid diethyl-amide;
7-[[5-Methoxy-1-(carboxylic acid 4-chlorophenyl amide)-1H-indol-3-yl]-acetylamino]-heptanoic acid diethyl-amide;
7-[[5-Hydroxy-1-(carboxylic acid 4-chlorophenyl amide)-1H-indol-3-yl]-acetylamino]-heptanoic acid diethyl-amide;
7-[[5-Acetoxy-1-(carboxylic acid 4-chlorophenyl amide)-1H-indol-3-yl]-acetylamino]-heptanoic acid diethyl-amide;
7-[[5-Methoxy-1-(carboxylic acid butyl amide)-1H-indol-3-yl]-acetylamino]-heptanoic acid diethyl-amide;
7-[[5-Hydroxy-1-(carboxylic acid butyl amide)-1H-indol-3-yl]-acetylamino]-heptanoic acid diethyl-amide;
7-[[5-Acetoxy-1-(carboxylic acid butyl amide)-1H-indol-3-yl]-acetylamino]-heptanoic acid diethyl-amide;
7-[[5-Methoxy-1-(4-butylbenzoyl)-2-methyl-1H-indol-3-yl]-acetylamino]-heptanoic acid diethyl-amide;
7-[[5-Hydroxy-1-(4-butylbenzoyl)-2-methyl-1H-indol-3-yl]-acetylamino]-heptanoic acid diethyl-amide;
8-[[5-Methoxy-2-methyl-1H-indol-3-yl]-acetylamino]-octanoic acid methyl-butyl-amide;
8-[[5-Hydroxy-2-methyl-1H-indol-3-yl]-acetylamino]-octanoic acid methyl-butyl-amide;

7-[[5-Acetoxy-1-(4-butylbenzoyl)-2-methyl-1H-indol-3-yl]-acetylamino]-heptanoic acid diethyl-amide.

A general synthetic procedure is set forth in Scheme A for preparing compounds of the present formula, Formula (I). In Scheme A, all substituents unless otherwise indicated, are as previously defined. Starting materials, reagents, techniques, and procedures used in Scheme A are well known and appreciated by one of ordinary skill in the art.

SCHEME A

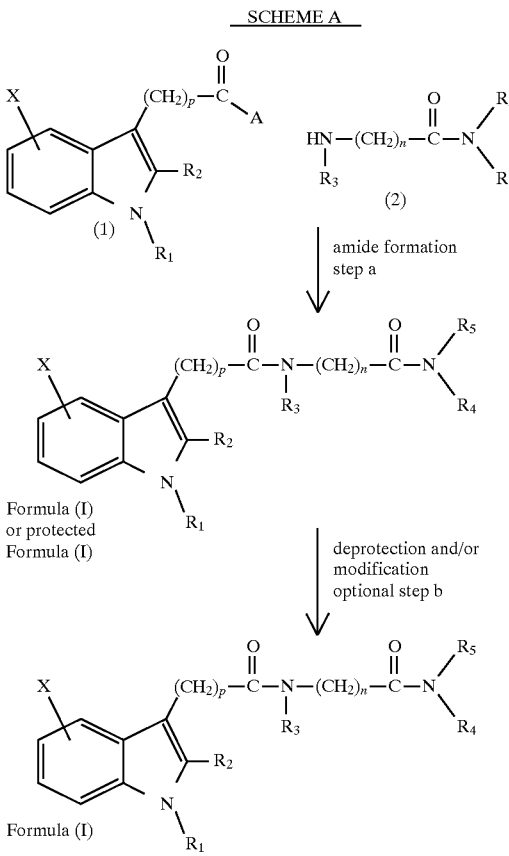

In Scheme A, step a, an appropriate indole compound of structure (1) undergoes an amidation reaction with an appropriate amine of structure (2) or the salt of an appropriate amine of structure (2) to give a protected compound of Formula (I) or a compound of Formula (I). An appropriate indole compound of structure (1) is one in which the group A undergoes an amidation reaction, X, $R_1$, $R_2$, and p are as desired in the final product of Formula (I) or give rise upon deprotection to X, $R_1$, and $R_2$, are as desired in the final product of Formula (I). An appropriate amine of structure (2) is one in which $R_3$, $R_4$, $R_5$ and n are as desired in the final product of Formula (I).

An amidation reaction may proceed through an acid, A is —OH; or an acid may be first converted to an acid chloride, A is —Cl; or an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; of an activated ester, such as phenol ester, p-nitrophenol ester, 2,4-dinitrophenlo ester, pentafluorophenol ester, pentachlorophenol ester, N-hydroxysuccinimide ester, N-hydroxyphthalimide ester, 1-hydroxy-1H-benztriazole eater, and the like; activated amide, such as imidazole, dimethylpyrazole, triazole, or tetrazole; or an intermediate formed in the presence of coupling agents, such as dicyclohexylcarbodiimide or 1-(3-dimethylaminopropyl)-3-ethylcarbodiimide. Acid chlorides and activated intermediates may be prepared but is not necessarily isolated before the addition of an appropriate amine of structure (2) or the salt of an appropriate amine of structure (2). Alternately, acid chlorides and activated intermediates may be prepared and isolated but not purified before the addition of an appropriate amine of structure (2). The use and formation of acid chlorides and activated intermediates is well known and appreciated in the art.

For example, an appropriate indole compound of structure (1) in which A is —OH is converted to the acid chloride, A is —Cl. An indole compound of structure (1) in which A is —OH is contacted with thionyl chloride or oxalyl chloride. The reaction is carried out using thionyl chloride or oxalyl chloride as a solvent or the reaction can be carried out in a suitable solvent, such as toluene, benzene, dichloromethane, carbon tetrachloride, or chloroform. The reaction may be carried out in the presence of a suitable catalyst, such as dimethylformamide or pyridine. The reaction is carried out at temperatures of from –40° C. to the refluxing temperature of the solvent. The reaction generally requires from 30 minutes to 24 hours. The product can be used after formation or used directly after isolation, or used after isolation and purification by techniques well known in the art, such as evaporation, extraction, chromatography, and recrystallization.

An indole compound of structure (1) in which A is —Cl is contacted with an amine of structure (2) or the salt of an amine of structure (2). The reaction is carried out in a suitable solvent, such as toluene, tetrahydrofuran, dimethylformamide, dichloromethane, pyridine, or chloroform. The reaction is carried out in the presence of a slight molar excess of a suitable base, such as triethyl amine, sodium carbonate, potassium bicarbonate, pyridine, or diisopropylethyl amine, if the salt of an amine of structure (2) is used an additional equimolar molar mount of a suitable base is used. The reaction is carried out a temperature of from –70° C. to the refluxing temperature of the solvent. The reaction generally requires from 30 minutes to 24 hours. The product can be isolated and purified by techniques well known in the art, such as extraction, evaporation, chromatography, and recrystallization.

Alternatively, for example, an indole compound of structure (1) in which A is —OH is contacted with 1.2 to 1.7 equivalents of a suitable base, such as N-methylmorpholine, in a suitable solvent, such as tetrahydrofuran. The reaction mixture is cooled to a temperature of between –50° C. and 0° C. with –25° C. to –20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between –50° C. and 0° C. an appropriate amine of structure (2) is added, if the salt of an amine of structure (2) is used an additional equimolar molar mount of a suitable base is used. The reaction may, after the addition of amine is complete, be warmed to room temperature. The reaction requires from 2 to 48 hours. The product can be isolated and purified by techniques well known in the art, such as extraction, evaporation, chromatography, and recrystallization.

Alternatively, for example, an indole compound of structure (1) in which A is —OH is contacted with a slight molar excess of an appropriate amine of structure (2) or a salt of an appropriate amine of structure (2) and 1-hydroxybenzotriazole hydrate in the presence of a slight molar excess of a coupling agent, such as dicyclohexylcarbodiimide or 1-(3-dimethyaminopropyl)-3-ethylcarbodiimide. The reaction is carried out in the presence of a suitable base, such as diisopropylethyl amine, if the salt of an amine of structure (2) is used an additional equimolar molar mount of a suitable base is used. The reaction is carried out in a suitable solvent, such as dichloromethane or chloroform. The product can be isolated and purified by techniques well known in the art, such as extraction, evaporation, chromatography, and recrystallization.

In Scheme A, optional step b, a compound of Formula (I) or a protected compound of Formula (I) undergoes an modification and/or a deprotection reaction to give a compound of Formula (I). The use and removal of protecting groups is well known in the art, specifically, the selection, use, and removal of hydroxy protecting groups and indole NH protecting groups and the removal of hydroxy protecting groups and indole NH protecting groups in a sequential manner utilizing suitable protecting groups such as those described in *Protecting Groups in Organic Synthesis* by T. Greene is well known and appreciated by those skilled in the art. The removal of protecting groups or the removal of protecting groups in a sequential manner as required gives compounds of Formula (I). Compounds of Formula (I) in which X and/or Y are hydroxy can be modified by an alkylation or acylation, as is well known in the art to give the alkylated and acylated compounds of Formula (I) in which X and Y are $C_1$–$C_4$ alkoxy or —OC(O)$R_6$. As is appreciated by one skilled in the art the number and order of the modification and deprotection reactions can be varied to obtain the desired compound of Formula (I).

The indole compounds of structure (1) are well known in the art and can be prepared by a variety of methods including, the Fischer indole synthesis; M. Julia and P. Manoury, *Bull. Soc. Chim Fr.* 1411 (1965); B. S. Thyagarajan et al, *Tet. Lets.* 1999–2002 (1974); E. E. Fischer and R. B. Carlin, *JACS* 70, 3421 (1948); A. P. Kozikowski et al, *J. Med. Chem.* 36, 2908–2920 (1993); B. Robinson, *Chem. Rev.* 63, 373 (1963); B. Robinson, *Chem. Rev.* 69, 227 (1963); *Indoles Part* 1, W. A. Remers and R. K. Brown, Chap 2 pp. 227–558, ed. by W. J. Houlihan, Wiley-Interscience 1972; T.-Y. Shen, British Patent No. 1,124,972 published Aug. 21, 1968; and British Patent No. 1,124,973 published Aug. 21, 1968; D. L. Hughes, *Org. Preps. and Proc. Int.* 25, 609–632 (1993); P. R. Ashton et al, *Synlett* 919–922 (1992); D. Zhoa et al, *JOC* 56, 3001–3006 (1991); R. S. Eichen-Conn et al, *JOC* 55, 2908–2913 (1990). In addition, an indole compound of structure (1) in which p is 0 can be obtained by the carboxylation of a suitable 1H-indoles under basic conditions by reagents suitable for transferring a carboxy group or a protected carboxy group, such as carbon dioxide, methyl chloroformate, diethylcarbonate, or ethyl chloroformate. Alternately, an indole compounds of structure (1) in which p is 0 and $R_1$ is non-hydrogen can be obtained from 1-$R_1$-indoles by formation of a 1-$R_1$-indole-3-aldehyde by the Vilsmeier-Haack reaction followed by oxidation to the corresponding 1-$R_1$-indole-3-carboxylic acid.

A general synthetic procedure for preparing indole compounds of structure (1) by the Fischer indole synthesis is set forth in Scheme B. In Scheme B, all substituents unless otherwise indicated, are as previously defined. Starting materials, reagents, techniques, and procedures used in Scheme B are well known and appreciated by one of ordinary skill in the art.

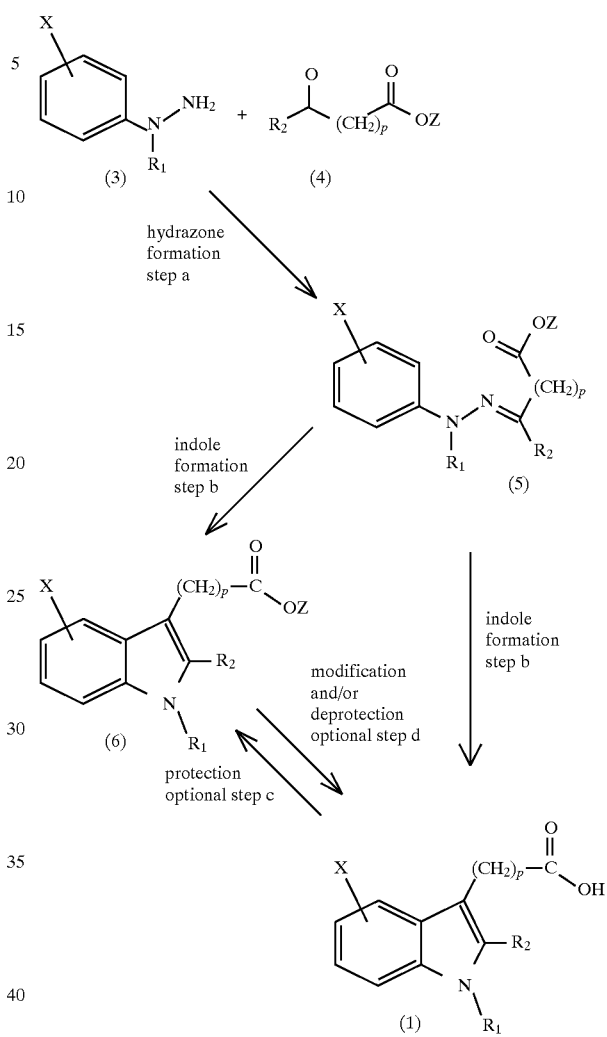

SCHEME B

In Scheme B, step a, an appropriate hydrazine of structure (3) or salt of an appropriate hydrazine of structure (3) is contacted with an appropriate carbonyl compound of structure (4) to give a hydrazone of structure (5).

An appropriate hydrazine of structure (3) or a salt of an appropriate hydrazine of structure (3) is one in which X and $R_1$ are as desired in the final product of Formula (I) or give rise after deprotection and/or modification to X and $R_1$ are as desired in the final product of Formula (I). An appropriate hydrazine of structure (3) or a salt of an appropriate hydrazine of structure (3) is readily available to one of ordinary skill in the art by reduction of an appropriate diazonium salt prepared from the corresponding aniline. As is well known in the art, an appropriate hydrazine of structure (3) or a salt of an appropriate hydrazine of structure (3) in which $R_1$ is $C_1$–$C_4$ alkyl, benzyl, substituted benzyl, benzoyl, or substituted benzoyl can be prepared by an alkylation, benzylation, or benzoylation reaction on a suitably protected hydrazine of structure (3) in which $R_1$ is hydrogen. Suitable protecting groups include imines and the t-BOC protecting group [P. R. Ashton, et al, *Synlett* 919–922 (1992)]. Deprotection of the alkylated, benzylated, or benzoylated hydrazine provides an appropriate hydrazine of structure (3) in which $R_1$ is $C_1$–$C_4$ alkyl, benzyl, substituted benzyl, benzoyl, or substituted benzoyl.

An appropriate carbonyl compound of structure (4) is one in which $R_2$, and p are as desired in the final product of Formula (I) or give rise after deprotection and/or modification to $R_2$ as desired in the final product of Formula (I).

An appropriate carbonyl compound of structure (4) in which p is 0 can be obtained by the carboxylation of a suitable ketone by reagents suitable for transferring a carboxy group or a protected carboxy group, such as carbon dioxide, methyl chloroformate, diethylcarbonate, or ethyl chloroformate [E. J. Corey and R. H. K. Chen, *JOC* 38, 4086 (1973); S. B. Soloway and F. B. LaForge, *JACS* 69, 2677 (1947); N. Green and F. B. LaForge, *JACS* 70, 2287 (1948); Y.-L. Chen and W. F. Barthel, *JACS* 75, 4287 (1953)]. Alternately, an appropriate carbonyl compound of structure (4) in which p is 0 can be obtained from a suitable activated acid, such as an acid chloride by reaction with a reagent which transfers an methylcarboxy group or a protected methylcarboxy group, such as malonate esters, malonate half-esters, acetoacetate esters, or acetic acid esters [*Org. Syn.* 37, 32–33 (1957) (John Wiley & Sons Inc.); *J. Heterocyclic Chem.* 24, 453 (1987)].

An appropriate carbonyl compound of structure (4) in which p is 1 can be obtained by the cyanide ion catalyzed addition of a suitable aldehyde to acrylonitrile followed by hydrolysis [H. Stetter and H. Kulhmann, *Org. Reactions* 40, 407–496 (1991)]. Alternately, an appropriate carbonyl compound of structure (4) in which p is 1 can be obtained by the well known Friedel-Crafts reaction of succinic anhydride with a suitable phenyl or substituted phenyl. [A. P. Kozikowski et al, *J. Med. Chem.* 36, 2908–2920 (1993)]

For example, in Scheme B, step a, an appropriate carbonyl compound of structure (4) is contacted with an equimolar amount or a slight molar excess of an appropriate hydrazine of structure (3) or a salt of an appropriate hydrazine of structure (3). The reaction is carried out in a suitable solvent, such as methanol, ethanol, or acetic acid. When a salt of an appropriate hydrazine of structure (3) is used the reaction is carried out in the presence of an equimolar amount of a suitable base, such as sodium acetate, triethylamine, or diisopropylethylamine. The reaction is carried out at from ambient temperature to the refluxing temperature of the solvent. The reaction generally requires from 5 minutes to 8 hours. The product can be used directly, or can be isolated before its use or can be isolated and purified by techniques well known in the art, such as filtration, trituration, evaporation, chromatography, and recrystallization.

In Scheme B, step b, an appropriate hydrazone of structure (5) in which Z is hydrogen undergoes an indole forming reaction to give an indole compound of structure (1).

For example, in Scheme B, step b, an appropriate hydrazone of structure (5) in which Z is hydrogen undergoes an indole forming reaction. The reaction is carried out in a suitable solvent, such as toluene, benzene, methanol, ethanol, water, sulfuric acid, or acetic acid. The reaction is carried out thermally or in the presence of a suitable catalyst, such as strong acids (p-toluenesulfonic acid, hydrochloric acid, sulfuric acid, polyphosphoric acid, and the like), weak acids (acetic acid, formic acid, pyridine hydrochloride, and the like), solid acids (Zeolite catalysts, such as Zeolite Y, Mordenite, sulfonic acid resins, and the like), or Lewis acids (zinc chloride, phosphorous trichloride, boron trifluoride, and the like). The reaction is generally carried out at from ambient temperature to the refluxing temperature of the solvent. The reaction generally requires from 30 minutes to 48 hours. The product can be isolated and purified by techniques well known in the art, such as filtration, trituration, evaporation, chromatography, and recrystallization.

Alternately, in Scheme B, step b, an appropriate hydrazone of structure (5) in which Z is a protecting group, such as $C_1$–$C_4$ alkyl or benzyl, undergoes an indole forming reaction as taught in Scheme B, step b, to give an indole compound of structure (6) in which Z is a protecting group, such as $C_1$–$C_4$ alkyl or benzyl. An appropriate indole compounds of structure (6) in which Z is a protecting group and $R_1$ is hydrogen are useful as starting materials for an alternative route to introduce, by a modification reaction, $R_1$ which are $C_1$–$C_4$, benzyl, substituted benzyl, benzoyl, and substituted benzoyl.

In Scheme B, optional step c, a compound of Formula (I) can be esterified by procedures well known in the art to give an indole compound of structure (6) in which Z is a protecting group, such as $C_1$–$C_4$ alkyl or benzyl.

In Scheme B, optional step d, an indole compound of structure (6) in which $R_1$ is hydrogen, $C_1$–$C_4$ alkyl, benzyl, substituted benzyl, benzoyl, and substituted benzoyl; and Z is a protecting group, such as $C_1$–$C_4$ alkyl or benzyl is deprotected. A deprotection reaction, such as the hydrolysis of an esters utilizing suitable protecting groups such as those described in *Protecting Groups in Organic Synthesis* by T. Greene is well known and appreciated in the art. Optionally, an indole compound of structure (6) in which $R_1$ is hydrogen and Z is a protecting group, such as $C_1$–$C_4$ alkyl or benzyl is modified to give an indole compound of structure (6) in which $R_1$ is $C_1$–$C_4$ alkyl, benzyl, substituted benzyl, benzoyl, and substituted benzoyl; and Z is a protecting group. A modification reaction, such as an alkylation, benzylation, or acylation, as are well known in the art, to give an indole compound of structure (6) in which Z is a protecting group and $R_1$ is $C_1$–$C_4$, benzyl, substituted benzyl, benzoyl, or substituted benzoyl. Removal of the protecting group Z by a deprotection reaction, such as those described in *Protecting Groups in Organic Synthesis* by T. Greene gives an indole compound of structure (1) in which $R_1$ is $C_1$–$C_4$, benzyl, substituted benzyl, benzoyl, or substituted benzoyl.

As is appreciated by one of ordinary skill in the art the number and order of the modification and deprotection reactions can be varied to obtain the desired compound of Formula (I).

A general synthetic procedure is set forth in Scheme C for preparing amines of structure (2). In Scheme C, all substituents unless otherwise indicated, are as previously defined. Starting materials, reagents, techniques, and procedures used in Scheme C are well known and appreciated by one of ordinary skill in the art.

SCHEME C

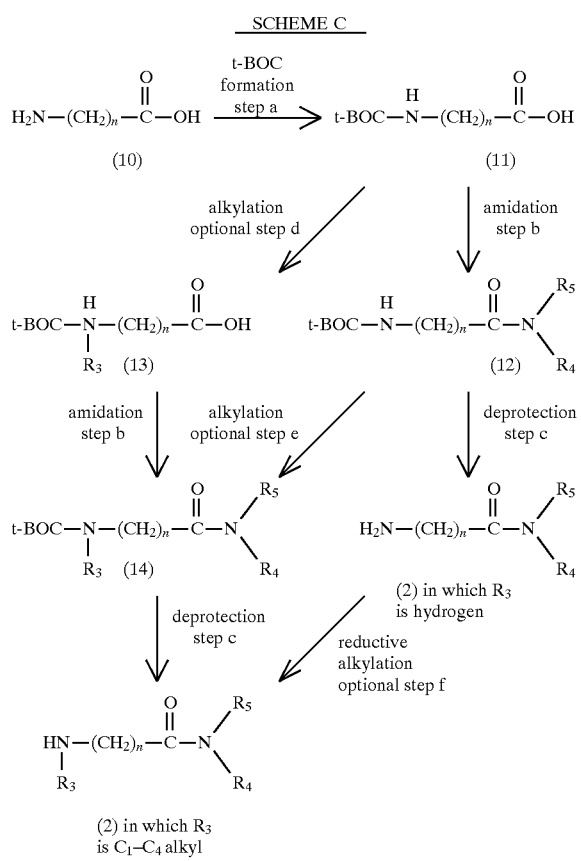

In Scheme C, step a, an appropriate ω-amino acid of structure (10) undergoes an t-BOC forming reaction to give a t-BOC protected ω-amino acid of structure (11). An appropriate ω-amino acid of structure (10) is one in which n is as desired in the final product o Formula (I).

For example, an appropriate ω-amino acid of structure (10) is contacted with a reagent which transfers a t-BOC group, such as di-t-butyl dicarbonate or 2-(t-butoxycarbonyloxyimino)-2-phenylaceto-nitrile. The reaction is carried out in a suitable such as toluene, methanol, ethanol, dichloromethane, tetrahydrofuran, or acetonitrile. The reaction may be carried out in the presence of a suitable catalyst, such as 4-dimethylaminopyridine. The reaction is generally carried out at from 0° C. to the refluxing temperature of the solvent. The reaction generally requires from 30 minutes to 24 hours. The product can be isolated and purified by techniques well known in the art, such as filtration, trituration, evaporation, extraction, chromatography, and recrystallization.

In Scheme C, step b, a t-BOC protected ω-amino acid of structure (11) undergoes an amidation reaction with an appropriate amine or a salt of an appropriate amine to give a t-BOC protected ω-amino acid amide of structure (12). An appropriate amine, $HNR_4R_5$ is one in which $R_4$ and $R_5$ are as desired in the final product of Formula (I).

An amidation reaction may proceed through a t-BOC protected ω-amino acid of structure (11) or the acid function of t-BOC protected ω-amino acid of structure (11) may be first converted to an activated intermediate; such as an anhydride; a mixed anhydride of substituted phosphoric acid, such as dialkylphosphoric acid, diphenylphosphoric acid, halophosphoric acid; of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; an activated ester, such as phenol ester, p-nitrophenol ester, 2,4-dinitrophenlo ester, pentafluorophenol ester, pentachlorophenol ester, N-hydroxysuccinimide ester, N-hydroxyphthalimide ester, 1-hydroxy-1H-benztriazole eater, and the like; activated amide, such as imidazole, dimethylpyrazole, triazole, or tetrazole; or the intermediate formed in the presence of coupling agents, such as dicyclohexylcarbodiimide or 1-(3-dimethyaminopropyl)-3-ethylcarbodiimide. Activated intermediates may be prepared and used directly, or are prepared and isolated before the addition of an appropriate amine, $HNR_4R_5$. Alternately, activated intermediates may be prepared isolated and purified before the addition of an appropriate amine, $HNR_4R_5$. The use and formation of activated intermediates is well known and appreciated in the art.

For example, a t-BOC protected ω-amino acid of structure (11) is contacted with a slight molar excess of an appropriate amine, $HNR_4R_5$ or a salt of an appropriate amine and 1-hydroxybenzotriazole hydrate in the presence of a slight molar excess of a coupling agent, such as dicyclohexylcarbodiimide or 1-(3-dimethyaminopropyl)-3-ethylcarbodiimide. The reaction is carried out in the presence of a suitable base, such as diisopropylethyl amine, if the salt of an amine is used an additional equimolar molar mount of a suitable base is added. The reaction is carried out in a suitable solvent, such as dichloromethane or chloroform. The product can be isolated and purified by techniques well known in the art, such as extraction, evaporation, chromatography, and recrystallization.

Alternatively, for example, a t-BOC protected ω-amino acid of structure (11) is contacted with 1.2 to 1.7 equivalents of a suitable base, such as N-methylmorpholine, in a suitable solvent, such as tetrahydrofuran. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between −50° C. and 0° C. an appropriate amine, $HNR_4R_5$ is added, if the salt of an amine is used an additional equimolar molar mount of a suitable base is added. The reaction may, after the addition of amine is complete, be warmed to room temperature. The reaction requires from 2 to 48 hours. The product can be isolated and purified by techniques well known in the art, such as extraction, evaporation, chromatography, and recrystallization.

In Scheme C, step c, a t-BOC protected ω-amino acid amide of structure (12) is deprotected to give an amine of structure (2) in which $R_3$ is hydrogen or a salt of an amine of structure (2) in which $R_3$ is hydrogen.

For example, a t-BOC protected ω-amino acid amide of structure (12) is contacted with a suitable protic acid, such as trifluoroacetic acid, hydrochloric acid, hydrobromic acid, or sulfuric acid. The reaction is carried out in a suitable solvent, such as dioxane, methanol, ethanol, ethyl acetate, or water. The reaction is generally carried out at from 0° C. to the refluxing temperature of the solvent. The reaction generally requires from 30 minutes to 24 hours. The product can be isolated and purified by techniques well known in the art, such as extraction, evaporation, chromatography, and recrystallization. The product may be used directly after isolation as a solution or may be further purified.

In Scheme C, optional step d, a t-BOC protected ω-amino acid of structure (11) is alkylated to give a a t-BOC protected N-alkyl-ω-amino acid of structure (13).

For example, a t-BOC protected ω-amino acid of structure (11) is contacted with a slight excess of an appropriate alkylating agent. An appropriate alkylating agent is one which transfers an $C_1$–$C_4$ alkyl group, such as methyl iodide, methyl bromide, ethyl iodide, ethyl bromide, propyl iodide, propyl tosylate, butyl iodide, or butyl trifluoromethane sulfonate. The reaction is carried out in the presence of 2.0 to 4.0 molar equivalents of a suitable base, such as sodium hydride, as potassium t-butoxide, sodium ethoxide, lithium hexamethyldisilazide, or lithium diisopropylamide with sodium hydride being preferred. The reaction is carried out in a suitable solvent, such as tetrahydrofuran. The reaction is generally carried out at from −78° C. to the refluxing temperature of the solvent. The reaction generally requires from 30 minutes to 24 hours. The product can be isolated and purified by techniques well known in the art, such as extraction, evaporation, chromatography, and recrystallization.

In Scheme C, step b, a t-BOC protected N-alkyl-ω-amino acid of structure (13) undergoes an amidation reaction with an appropriate amine, $HNR_4R_5$, as taught above to give a t-BOC protected N-alkyl-ω-amino acid amide of structure (14).

Alternately, in Scheme C, optional step e, a t-BOC protected ω-amino acid amide of structure (12) is alkylated to give a a t-BOC protected N-alkyl-ω-amino acid amide of structure (14).

For example, a t-BOC protected ω-amino acid amide of structure (12) is contacted with a slight excess of an appropriate alkylating agent. An appropriate alkylating agent is one which transfers an $C_1$–$C_4$ alkyl group, such as methyl iodide, methyl bromide, ethyl iodide, ethyl bromide, propyl iodide, propyl tosylate, butyl iodide, or butyl trifluoromethane sulfonate. The reaction is carried out in the presence of 1.0 to 2.0 molar equivalents of a suitable base, such as sodium hydride, potassium t-butoxide, sodium ethoxide, lithium hexamethyldisilazide, or lithium diisopropylamide with sodium hydride being preferred. The reaction is carried out in a suitable solvent, such as tetrahydrofuran. The reaction is generally carried out at from −78° C. to the refluxing temperature of the solvent. The reaction generally requires from 30 minutes to 24 hours. The product can be isolated and purified by techniques well known in the art, such as extraction, evaporation, chromatography, and recrystallization.

In Scheme C step c, a t-BOC protected N-alkyl-ω-amino acid amide of structure (14) is deprotected as taught above to give an amine of structure (2) in which $R_3$ is $C_1$–$C_4$ alkyl or a salt of an amine of structure (2) in which $R_3$ is $C_1$–$C_4$ alkyl.

Alternately, in Scheme C, optional step f, an amine of structure (2) in which $R_3$ is hydrogen or a salt of an amine of structure (2) in which $R_3$ is hydrogen undergoes a reductive amination to give an amine of structure (2) in which $R_3$ is $C_1$–$C_4$ alkyl or a salt of an amine of structure (2) in which $R_3$ is $C_1$–$C_4$ alkyl.

For example, an amine of structure (2) in which $R_3$ is hydrogen or a salt of an amine of structure (2) is contacted with an appropriate aldehyde, such as formaldehyde, acetaldehyde, propionaldehyde, or butyraldehyde. The reaction is carried out in the presence of an excess of sodium cyanoborohydride by the method of R. F. Borch et al, *JACS* 93, 2891–2904 (1971). The reaction is carried out in a suitable solvent, such as ethanol, methanol or tetrahydrofuran/methanol mixtures. The pH of the reaction mixture is maintained between 6 and 8 during the course of the reaction by the addition of concentrated aqueous hydrochloric acid. The reaction is generally carried out at from ambient temperature to the refluxing temperature of the solvent. The reaction generally requires from 15 minutes to 24 hours. The product can be isolated and purified by techniques well known in the art, such as extraction, evaporation, chromatography, and recrystallization.

The following preparations and examples present typical syntheses as described in Schemes A, B and C. These preparations examples are understood to be illustrative only and are not intended to limit the scope of the invention in any way. As used in the following preparations and examples, the following terms have the meanings indicated: "g" refers to grams, "mg" refers to milligrams, "mmol" refers to millimoles, "mL" refers to milliliters, "°C." refers to degrees Celsius, "mp" refers to melting point, "dec" refers to decomposition.

PREPARATION 1 a) 1-[5-Methoxy-1-benzoyl-2-methyl-1H-indol-3-yl]-acetic acid chloride

Combine 1-[5-methoxy-1-benzoyl-2-methyl-1H-indol-3-yl]-acetic acid (1.0 g, 3.0 mmol) and thionyl chloride (1.5 mL, 6.0 mmol) in toluene (10 mL). Heat to 70° C. for 1 hour. Cool to ambient temperature and evaporate under a stream of nitrogen to give the title compound as a residue which is used without further purification.

b) [5-Methoxy-1-(4-chlorobenzoyl)-2-methyl-1H-indol-3-yl]-acetic acid chloride

Prepare by a method similar to Preparation 1a using [5-methoxy-1-(4-chlorobenzoyl)-2-methyl-1H-indol-3-yl]-acetic acid.

PREPARATION 2 a) N-Benzoyl-N-(4-methoxyphenyl)-hydrazine hydrochloride salt

Combine (4-methoxyphenyl)-hydrazine hydrochloride salt (10 g, 57 mmol), sodium hydroxide solution (50 mL, 1M), and extract with toluene. Dry the organic layer over $MgSO_4$, filter, and evaporate in vacuo to give a residue. Combine the residue and toluene (50 mL) and cool to 0° C. Add acetaldehyde (3.5 mL, 63 mmol) dropwise as a solution in toluene (10 mL). When the addition is complete, warm to ambient temperature. After 1 hour at ambient temperature evaporate under a stream of nitrogen to give N-(4-methoxyphenyl)-N'-ethylidene hydrazine.

Combine N-(4-methoxyphenyl)-N'-ethylidene hydrazine (6.0 g, 43 mmol), benzoyl chloride (5.2 mL. 44 mmol), pyridine (3.7 mL, 46 mmol), and diethyl ether (25 mL). After 24 hours, add diethyl ether (100 mL), remove the solid by filtration and dry in vacuo to give N-benzoyl-N-(4-methoxyphenyl)-N'-ethylidene hydrazine as a solid.

Combine N-benzoyl-N-(4-methoxyphenyl)-N'-ethylidene hydrazine obtained above, diethyl ether (10 mL) and ethanol (10 mL). Add hydrochloric acid gas until the solution is saturated. After 20 minutes, add diethyl ether (100 mL) to form a solid. Remove the solid by filtration and dry in vacuo to give the title compound.

b) N-Benzoyl-N-phenyl-hydrazine hydrochloride salt

Prepare by a method similar to Preparation 2a using phenylhydrazine hydrochloride salt.

c) N-(4-Chlorobenzoyl)-N-(4-methoxyphenyl)-hydrazine hydrochloride salt

Prepare by a method similar to Preparation 2a using 4-chlorobenzoyl chloride.

PREPARATION 3

Levulinic acid methyl ester

Combine levulinic acid (6.0 g) and Amberlyst 15 in methanol (75 mL). After 24 hours, remove the resin by filtration and evaporate in vacuo to obtain a residue. Partition the residue between ethyl acetate and saturated sodium bicarbonate solution. Dry the organic layer over $MgSO_4$, filter, and evaporate in vacuo to give the title compound.

EXAMPLE 1

8-[[5-Methoxy-1-benzoyl-2-methyl-1H-indol-3-yl]-acetylamino]-octanoic acid methyl-butyl-amide Scheme A, step a

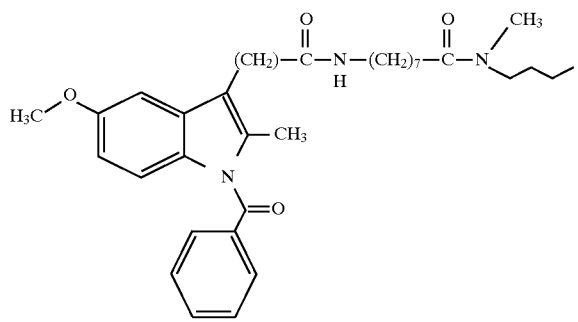

Combine 1-[5-methoxy-1-benzoyl-2-methyl-1H-indol-3-yl]-acetic acid chloride (3.0 mmol), 8-amino-octanoic acid methyl-butyl-amide (3.0 mmol, in toluene (100 mL)), and diisopropylethylamine 1.0 mL, 6.0 mmol). Stir at ambient temperature for 4 hours. Partition the reaction mixture between ethyl acetate and a saturated sodium chloride solution. Dry the organic layer over $MgSO_4$, filter, and evaporate in vacuo to give a residue. Chromatograph the residue on silica gel eluting with 25% acetone/dichloromethane to give the title compound.

EXAMPLE 2

8-[[5-Methoxy-1-(4-chlorobenzoyl)-2-methyl-1H-indol-3-yl]-acetylamino]-octanoic acid methyl-butyl-amide Scheme A, step a

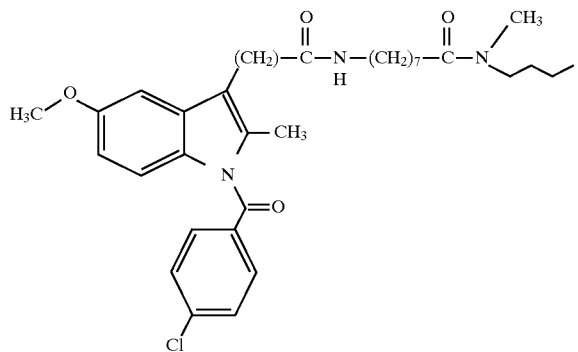

Prepare by a method similar to Example 1 using 1-[5-methoxy-1-(4-chlorobenzoyl)-2-methyl-1H-indol-3-yl]-acetic acid chloride.

EXAMPLE 3

8-[[5-Methoxy-1-methyl-2-[(4-methoxy)phenyl]-1H-indol-3-yl]-acetylamino]-octanoic acid methyl-butyl-amide Scheme A, step a

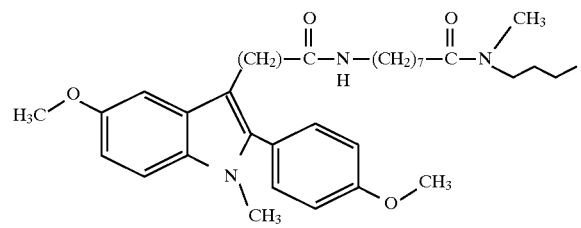

Combine 1-[5-methoxy-1-methyl-2-[(4-methoxy)phenyl]-1H-indol-3-yl]-acetic acid (0.2 g, 0.64 mmol), 8-amino-octanoic acid methyl-butyl-amide hydrochloric acid salt (0.64 mmol), N-methylmorpholine (0.38 mL, 3.0 mmol), 1-(3-dimethylaminopropyl)-3-ethyl carbodiimide hydrochloride salt (0.12 g, 0.64 mmol), and 4-hydroxybenztriazole hydrate (0.01 g) in dichloromethane (20 mL). After 18 hours, add water and extract with ethyl acetate. Dry the organic layer over $MgSO_4$ and evaporate in vacuo to give a residue. Chromatograph the residue on silica gel eluting with 50% ethyl acetate/hexane.

EXAMPLE 4

8-[[5-Methoxy-1-benzyl-2-[(4-methoxy)phenyl]-1H-indol-3-yl]-acetylamino]-octanoic acid methyl-butyl-amide Scheme A, step a

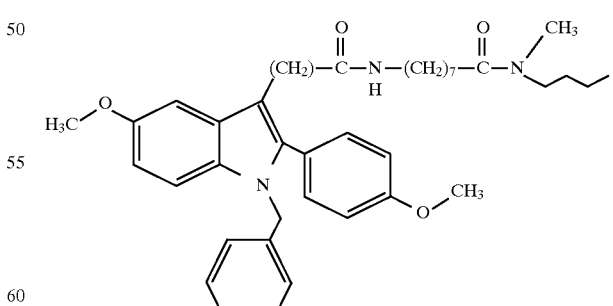

Prepare by a method similar to Example 3 using 1-[5-methoxy-1-benzyl-2-[(4-methoxy)phenyl]-1H-indol-3-yl]-acetic acid.

EXAMPLE 5

8-[[5-Methoxy-1-methyl-2-methyl-1H-indol-3-yl]-acetylamino]-octanoic acid methyl-butyl-amide

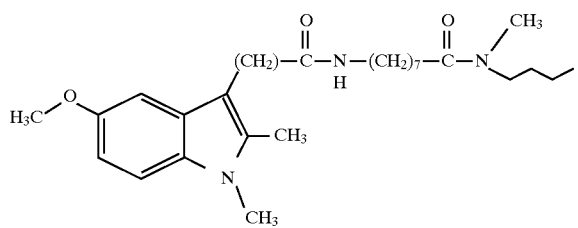

Prepare by a method similar to Example 3 using 1-[5-methoxy-1-methyl-2-methyl-1H-indol-3-yl]-acetic acid.

EXAMPLE 6

8-[[5-Methoxy-1-benzyl-2-methyl-1H-indol-3-yl]-acetylamino]-octanoic acid methyl-butyl-amide

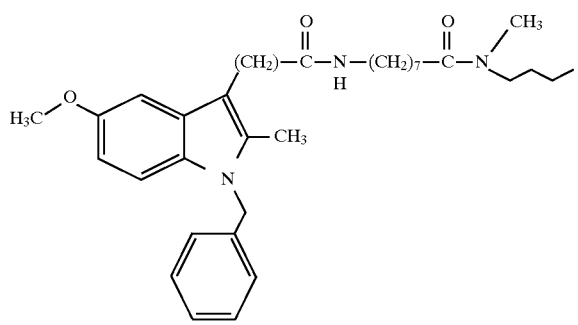

Prepare by a method similar to Example 3 using 1-[5-methoxy-1-benzyl-2-methyl-1H-indol-3-yl]-acetic acid.

EXAMPLE 7

8-[[5-Methoxy-1-benzyl-2-[(4-methoxy)phenyl]-1H-indol-3-yl]-acetylamino]-hexanoic acid methyl-butyl-amide Scheme A, step a

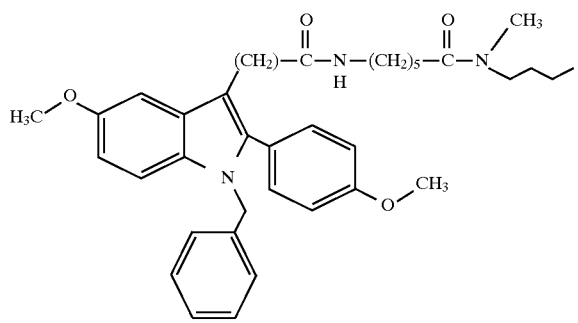

Prepare by a method similar to Example 3 using 1-[5-methoxy-1-benzyl-2-[(4-methoxy)phenyl]-1H-indol-3-yl]-acetic acid and 6-amino-hexanoic acid methyl-butyl-amide.

EXAMPLE 8

8-[[5-Methoxy-1-benzyl-2-[(4-methoxy)phenyl]-1H-indol-3-yl]-acetylamino]-octanoic acid butyl-amide Scheme A, step a

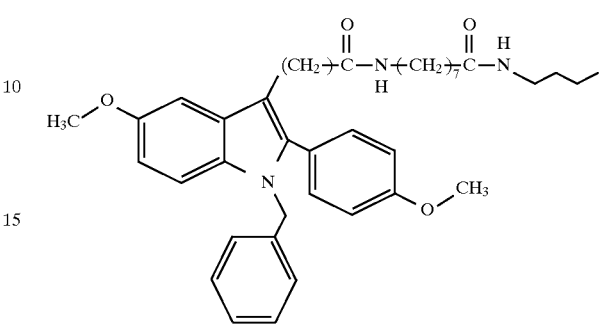

Prepare by a method similar to Example 3 using 1-[5-methoxy-1-benzyl-2-[(4-methoxy)phenyl]-1H-indol-3-yl]-acetic acid.

EXAMPLE 9

12-[[5-Chloro-1-ethyl-2-methyl-1H-indol-3-yl]-acetylamino]-dodecanoic acid methyl-butyl-amide Scheme A, step a

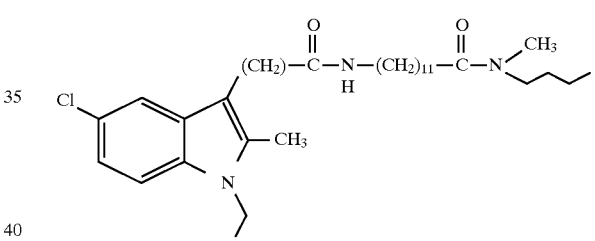

Prepare by a method similar to Example 3 using 1-[5-chloro-1-ethyl-2-methyl-1H-indol-3-yl]-acetic acid and 12-amino-dodecanoic acid butyl-methyl-amide.

EXAMPLE 10

8-[[5-Chloro-1-ethyl-2-methyl-1H-indol-3-yl]-acetyl-N-butylamino]-octanoic acid methyl-butyl-amide Scheme A, step a

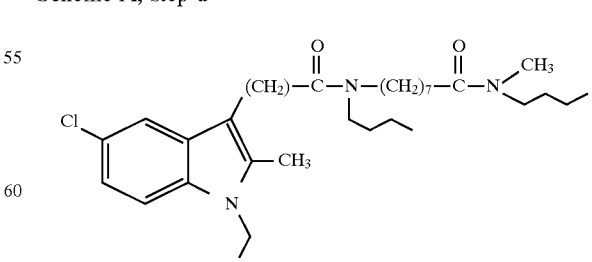

Prepare by a method similar to Example 3 using 1-[5-chloro-1-ethyl-2-methyl-1H-indol-3-yl]-acetic acid and 8-N-butylamino-octanoic acid methyl-butyl-amide.

EXAMPLE 11

6-[[5-Chloro-1-ethyl-2-methyl-1H-indol-3-yl]-acetylamino]-hexanoic acid methyl-butyl-amide Scheme A, step a

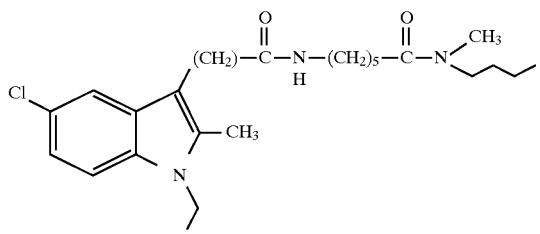

Prepare by a method similar to Example 3 using 1-[5-chloro-1-ethyl-2-methyl-1H-indol-3-yl]-acetic acid and 6-amino-hexanoic acid methyl-butyl-amide.

EXAMPLE 12

1-[[5-Chloro-1-ethyl-2-methyl-1H-indol-3-yl]-acetylamino]-acetic acid methyl-butyl-amide Scheme A, step a

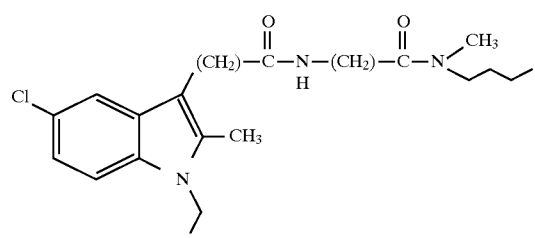

Prepare by a method similar to Example 3 using 1-[5-chloro-1-ethyl-2-methyl-1H-indol-3-yl]-acetic acid and 1-amino-acetic acid methyl-butyl-amide.

EXAMPLE 13

8-[[5-Methyl-1-[(4-methyl)benzyl]-2-[(4-methoxy)phenyl]-1H-indol-3-yl]-acetyl-N-methylamino]-octanoic acid methyl-butyl-amide Scheme A, step a

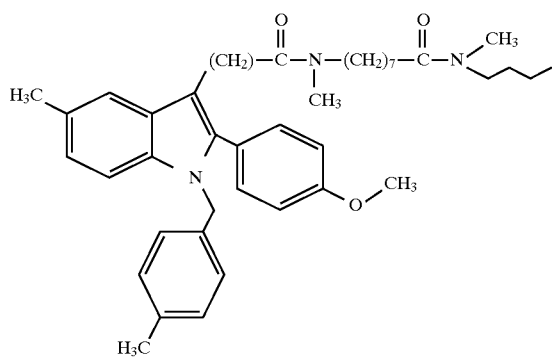

Prepare by a method similar to Example 3 using 1-[5-methyl-1-[(4-methyl)benzyl]-2-[(4-methoxy)phenyl]-1H-indol-3-yl]-acetic acid and 8-N-methylamino-octanoic acid methyl-butyl-amide.

EXAMPLE 14

8-[[5-Methoxy-1-benzyl-2-methyl-1H-indol-3-yl]-acetylamino]-octanoic acid butyl-octyl-amide

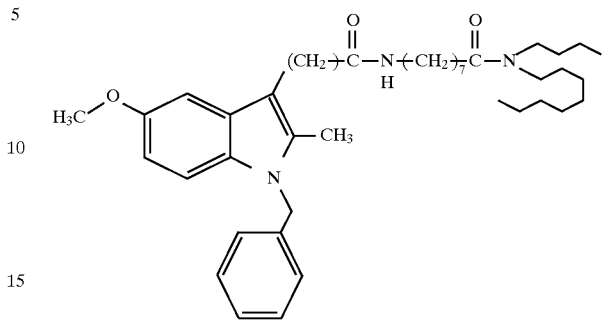

Scheme A, step a

Prepare by a method similar to Example 3 using 1-[5-methoxy-1-benzyl-2-methyl-1H-indol-3-yl]-acetic acid and 8-amino-octanoic acid butyl-octyl-amide.

EXAMPLE 15

8-[[5-Methoxy-1-benzyl-2-methyl-1H-indol-3-yl)-acetylamino]-octanoic acid methyl-amide

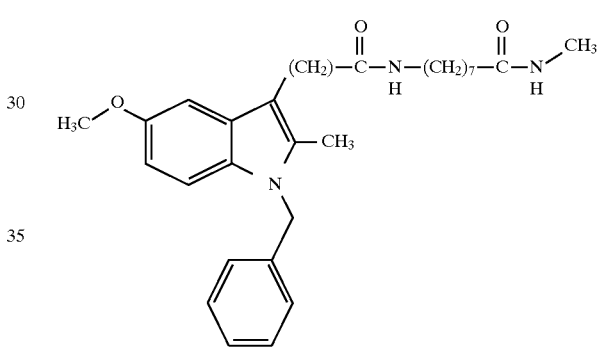

Scheme A, step a

Prepare by a method similar to Example 3 using 1-[5-methoxy-1-benzyl-2-methyl-1H-indol-3-yl]-acetic acid and 8-amino-octanoic acid methyl-amide.

EXAMPLE 16

8-[[5-Methoxy-1-benzyl-2-methyl-1H-indol-3-yl]-acetylamino]-octanoic acid dimethyl-amide Scheme A, step a

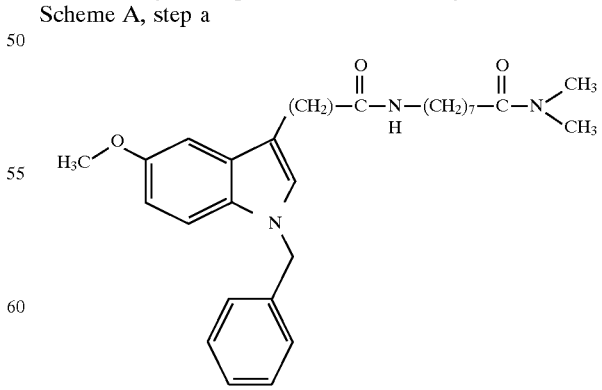

Prepare by a method similar to Example 3 using 1-[5-methoxy-1-benzyl-2-methyl-1H-indol-3-yl]-acetic acid and 8-amino-octanoic acid dimethyl-amide.

EXAMPLE 17

8-[[5-Methoxy-1-benzoyl-2-methyl-1H-indol-3-yl]-acetylamino]-octanoic acid methyl-amide Scheme A, step a

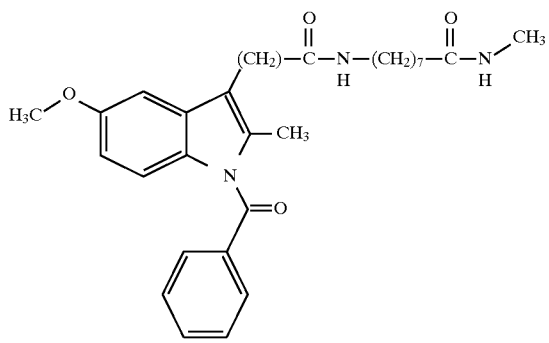

Prepare by a method similar to Example 3 using 1-[[5-methoxy-1-benzoyl-2-methyl-1H-indol-3-yl]-acetic acid and 8-amino-octanoic acid methyl-amide.

EXAMPLE 18

8-[[5-Methoxy-1-benzoyl-2-methyl-1H-indol-3-yl]-acetylamino]-octanoic acid dibutyl-amide Scheme A, step a

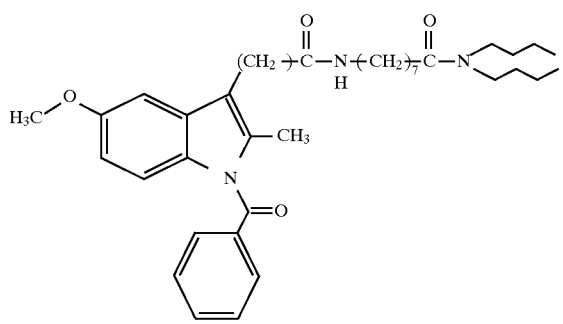

Prepare by a method similar to Example 3 using 1-[[5-methoxy-1-benzoyl-2-methyl-1H-indol-3-yl]-acetic acid and 8-amino-octanoic acid dibutyl-amide.

EXAMPLE 19

5-Chloro-1-methyl-1H-indole-3-carboxylic acid [8-(butyl-methyl-carbamoyl)-octyl]-amide Scheme A, step a

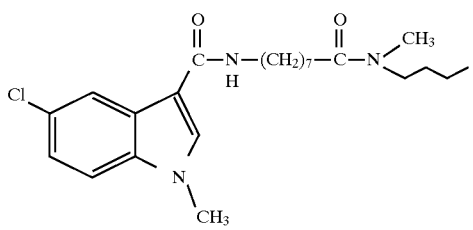

Prepare by a method similar to Example 3 using 5-chloro-1-methyl-1H-indole-3-carboxylic acid.

EXAMPLE 20

5-Methoxy-1-methyl-1H-indole-3-carboxylic acid [8-(butyl-methyl-carbamoyl)-octyl]-amide Scheme A, step a

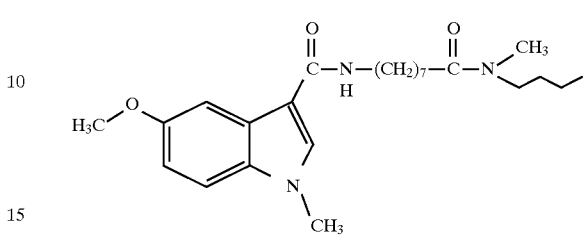

Prepare by a method similar to Example 3 using 5-methoxy-1-methyl-1H-indole-3-carboxylic acid.

EXAMPLE 21

5-Chloro-1-benzyl-1H-indole-3-carboxylic acid [8-(butyl-methyl-carbamoyl)-octyl]-amide Scheme A, step a

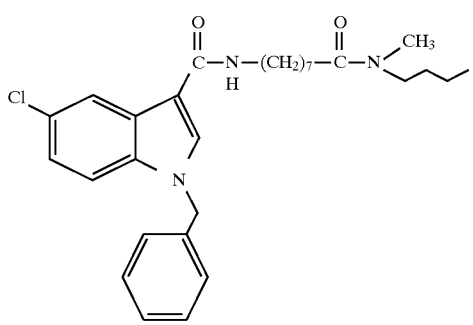

Prepare by a method similar to Example 3 using 5-chloro-1-benzyl-1H-indole-3-carboxylic acid.

EXAMPLE 22

5-Methoxy-1-benzyl-1H-indole-3-carboxylic acid [8-(butyl-methyl-carbamoyl)-octyl]-amide Scheme A, step a

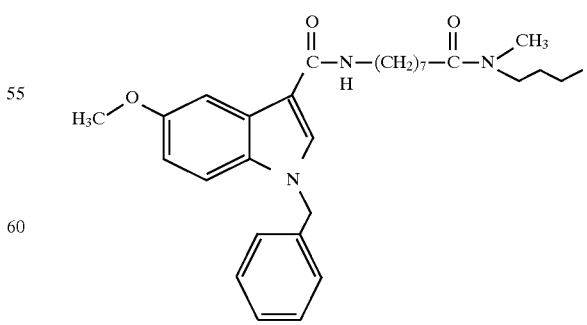

Prepare by a method similar to Example 3 using 5-methoxy-1-benzyl-1H-indole-3-carboxylic acid.

EXAMPLE 23

1-Benzoyl-2-methyl-1H-indole-3-caboxylic acid [8-(butyl-methyl-carbamoyl)-octyl]-amide Scheme A, step a

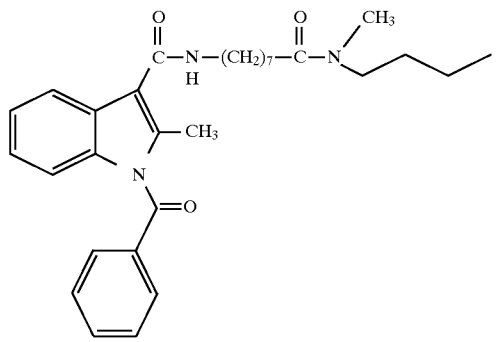

Prepare by a method similar to Example 3 using 1-benzoyl-2-methyl-1H-indole-3-caboxylic acid.

EXAMPLE 24

1-Benzoyl-2-[4-(methoxy)phenyl]-1H-indole-3-caboxylic acid [8-(butyl-methyl-carbamoyl)-octyl]-amide Scheme A, step a

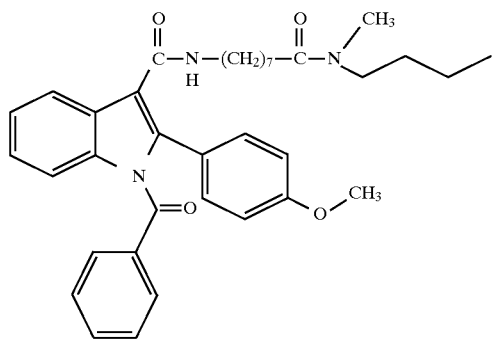

Prepare by a method similar to Example 3 using 1-benzoyl-2-[4-(methoxy)phenyl]-1H-indole-3-caboxylic acid.

EXAMPLE 25

5-Chloro-1-benzyl-1H-indole-3-carboxylic acid [6-(butyl-methyl-carbamoyl)-hexyl]-amide Scheme A, step a
Prepare by a method similar to

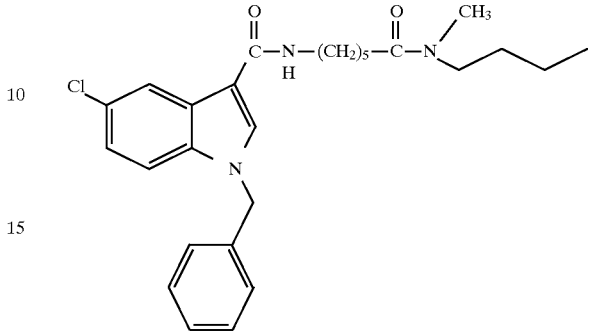

Example 3 using 5-Chloro-1-benzyl-1H-indole-3-carboxylic acid and 6-aminohexanoic acid methyl-butyl-amide.

EXAMPLE 26

5-Methoxy-1-benzyl-1H-indole-3-carboxylic acid [8-(butyl-methyl-carbamoyl)-hexyl]-amide Scheme A, step a

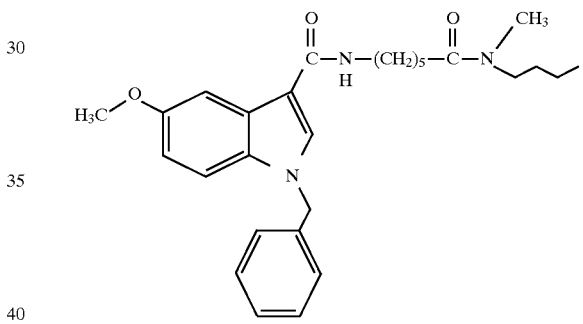

Prepare by a method similar to Example 3 using 5-methoxy-1-benzyl-1H-indole-3-carboxylic acid and 6-aminohexanoic acid methyl-butyl-amide.

EXAMPLE 27

8-[[5-Hydroxy-1-benzoyl-2-methyl-1H-indol-3-yl]-acetylamino]-octanoic acid methyl-butyl-amide Scheme A, optional deprotection step b

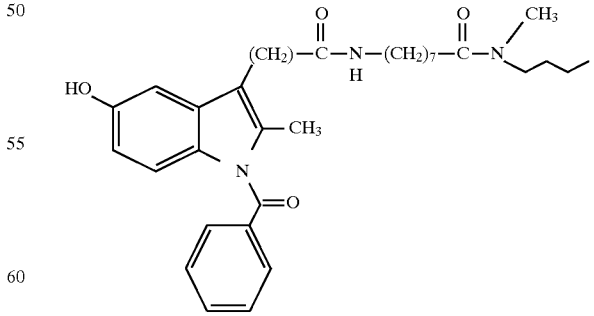

Combine 8-[[5-methoxy-1-benzoyl-2-methyl-1H-indol-3-yl]-acetylamino]-octanoic acid methyl-butyl-amide(0.4 g, 0.75 mmol) and dichloromethane (9 mL). Cool to −10° C. Add boron tribromide (1 mL, 1M on dichloromethane, 1 mmol). After the addition is complete, warm to ambient temperature. After 24 hours, partition the reaction mixture between ethyl acetate and water. Dry the organic layer over MgSO$_4$, filter, and evaporate in vacuo to give a residue. Chromatograph the residue on silica gel eluting with 25% acetone/chloroform to give the title compound.

EXAMPLE 28

8-[[5-Hydroxy-1-(4-chlorobenzoyl)-2-methyl-1H-indol-3-yl]-acetylamino]-octanoic acid methyl-butyl-amide Scheme A, optional deprotection step b

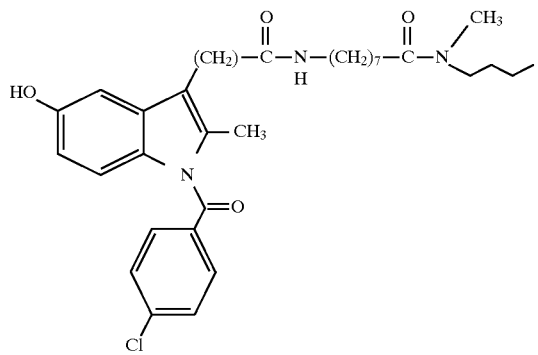

Prepare by a method similar to Example 27 using 8-[[5-methoxy-1-(4-chlorobenzoyl)-2-methyl-1H-indol-3-yl]-acetylamino]-octanoic acid methyl-butyl-amide.

EXAMPLE 29

8-[[5-Hydroxy-1-benzyl-2-[(4-hydroxy)-phenyl]-1H-indol-3-yl]-acetylamino]-octanoic acid methyl-butyl-amide Scheme A, optional deprotection step b

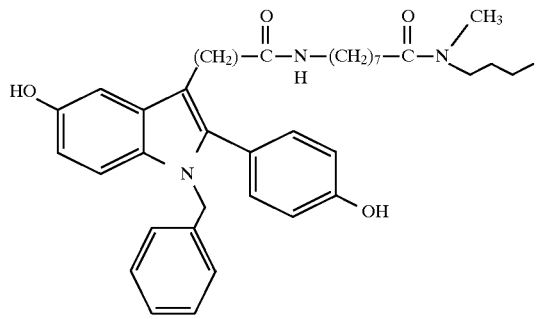

Combine 8-[[5-methoxy-1-phenyl-2-[(4-methoxy)phenyl]-1H-indol-3-yl]-acetylamino]-octanoic acid methyl-butyl-amide (0.31 g, 0.61 mmol) and dichloromethane (10 mL). Cool to −10° C. Add boron tribromide (2.44 mL, 1M in dichloromethane, 2.44 mmol). After the addition is complete, warm to ambient temperature. After 18 hours, partition the reaction mixture between ethyl acetate and water. Dry the organic layer over MgSO$_4$, filter, and evaporate in vacuo to give a residue. Chromatograph the residue on silica gel eluting with 25% acetone/chloroform to give the title compound.

EXAMPLE 30

8-[[5-Hydroxy-1-benzyl-2-[(4-hydroxy)phenyl]-1H-indol-3-yl]-acetylamino]-hexanoic acid methyl-butyl-amide Scheme A, optional deprotection step b

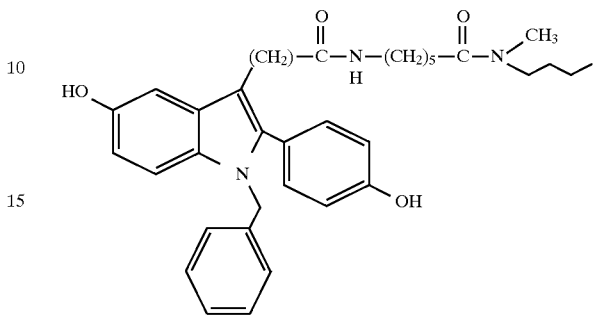

Prepare by a method similar to Example 29 using 8-[[5-methoxy-1-benzyl-2-[(4-methoxy)phenyl]-1H-indol-3-yl]-acetylamino]-hexanoic acid methyl-butyl-amide.

EXAMPLE 31

8-[[5-Hydroxy-1-benzyl-2-[(4-hydroxy)phenyl]-1H-indol-3-yl]-acetylamino]-octanoic acid butyl-amide Scheme A, optional deprotection step b

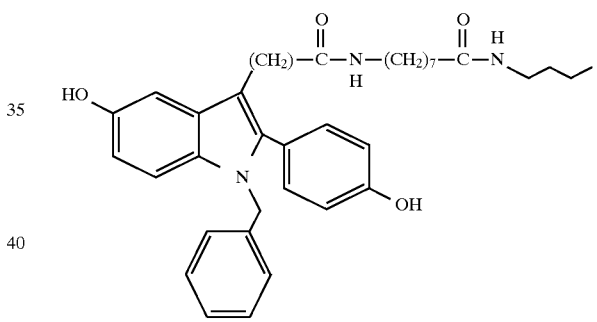

Prepare by a method similar to Example 29 using 8-[[5-methoxy-1-benzyl-2-[(4-methoxy)phenyl]-1H-indol-3-yl]-acetylamino]-octanoic acid butyl-amide.

EXAMPLE 32

5-Hydroxy-1-methyl-1H-indole-3-carboxylic acid [8-(butyl-methyl-carbamoyl)-octyl]-amide Scheme A, optional step b

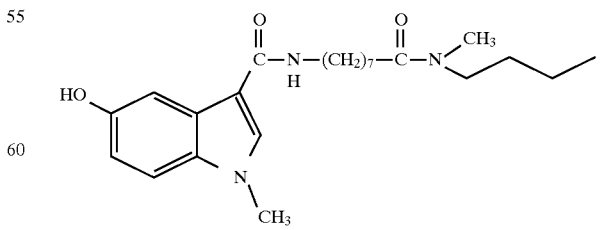

Prepare by a method similar to Example 27 using 5-methoxy-1-methyl-1H-indole-3-carboxylic acid [8-(butyl-methyl-carbamoyl)-octyl]-amide.

EXAMPLE 33

5-Hydroxy-1-benzyl-1H-indole-3-carboxylic acid [8-(butyl-methyl-carbamoyl)-octyl]-amide
Scheme A, optional step b

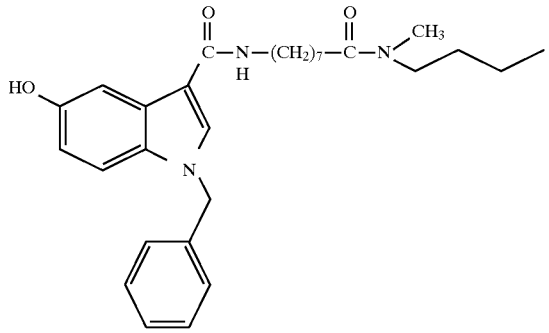

Prepare by a method similar to Example 27 using 5-methoxy-1-benzyl-1H-indole-3-carboxylic acid [8-(butyl-methyl-carbamoyl)-octyl]-amide.

EXAMPLE 34

8-[[5-Methoxy-2-methyl-1H-indol-3-yl]-acetylamino]-octanoic acid methyl-butyl-amide
Scheme A, optional deprotection step b

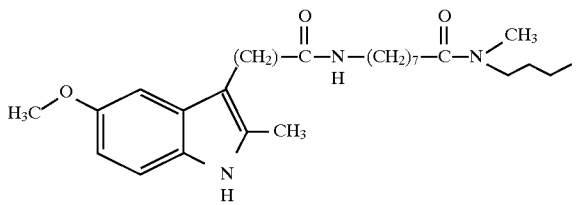

Combine 8-[[5-methoxy-1-benzoyl-2-methyl-1H-indol-3-yl]-acetylamino]-octanoic acid methyl-butyl-amide (3.0 mmol), sodium hydroxide (4.0 mmol), and ethanol/water (20 mL/5 mL). Heat to reflux. After 10 hours, partition the reaction mixture between ethyl acetate and a saturated sodium chloride solution. Dry the organic layer over MgSO₄, filter, and evaporate in vacuo to give a residue. Chromatograph the residue on silica gel to give the title compound.

EXAMPLE 35

2-Methyl-1H-indole-3-caboxylic acid [8-(butyl-methyl-carbamoyl)-octyl]-amide
Scheme A, optional deprotection step b

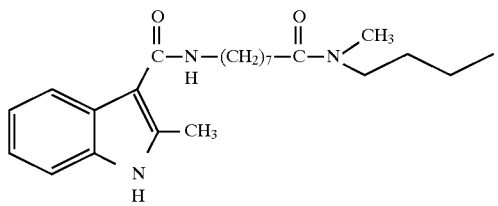

Prepare by a method similar to Example 34 using 1-benzoyl-2-methyl-1H-indole-3-caboxylic acid [8-(butyl-methyl-carbamoyl)-octyl]-amide.

EXAMPLE 36

2-[4-(Methoxy)phenyl]-1H-indole-3-caboxylic acid [8-(butyl-methyl-carbamoyl)-octyl]-amide
Scheme A, optional step b

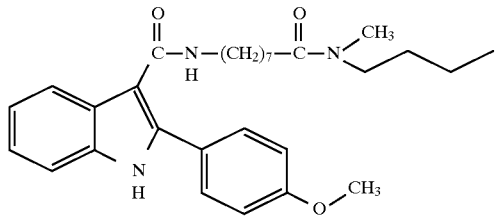

Prepare by a method similar to Example 34 using 1-benzoyl-2-[4-(methoxy)phenyl]-1H-indole-3-caboxylic acid [8-(butyl-methyl-carbamoyl)-octyl]-amide.

EXAMPLE 37

8-[[5-Acetoxy-1-benzyl-2-[(4-acetoxy)-phenyl]-1H-indol-3-yl]-acetylamino]-octanoic acid methyl-butyl-amide
Scheme A, optional modification step b

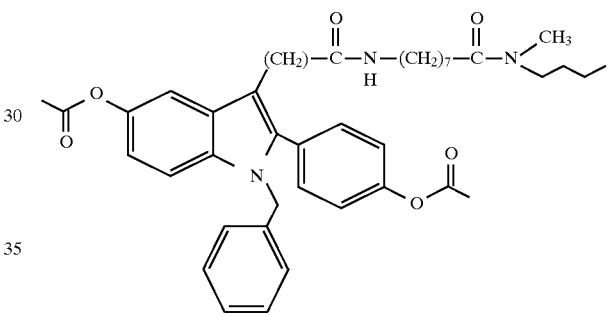

Combine 8-[[5-hydroxy-1-benzyl-2-[(4-hydroxy)-phenyl]-1H-indol-3-yl]-acetylamino]-octanoic acid methyl-butyl-amide (0.462 g, 0.79 mmol) and acetic anhydride (2.20 g, 1.74 mmol), 4-dimethylaminopyridine (1.97 mmol) and dichloromethane (10 mL). After 24 hours, partition the reaction mixture between ethyl acetate and water. Dry the organic layer over MgSO₄, filter, and evaporate in vacuo to give a residue. Chromatograph the residue on silica gel eluting with 25% acetone/chloroform to give a residue. Triturate the residue with diethyl ether and dry in vacuo to give the title compound: mp 60°–70° C.

EXAMPLE 38

1-[5-Methoxy-1-benzoyl-2-methyl-1H-indol-3-yl]-acetic acid
Scheme B, step a and step b
Combine N-benzoyl-N-(4-methoxyphenyl)-hydrazine hydrochloride salt (3.0 g, 11 mmol), sodium acetate (11 mmol), and levulinic acid (1.3 g, 11 mmol) in acetic acid (130 mL). Heat the reaction mixture to 80° C. After 3 hours, cool to ambient temperature and stir for 18 hours. Filter the solid which forms and dry in vacuo to give the title compound as a solid.

EXAMPLE 39

1-[5-Methoxy-1-(4-chlorobenzoyl)-2-methyl-1H-indol-3-yl]-acetic acid
Scheme B, step a and step b Prepare by a method similar to Example 38 using N-(4-chlorobenzoyl)-N-(4-methoxyphenyl)-hydrazine hydrochloride salt.

EXAMPLE 40

1-Benzoyl-2-methyl-1H-indole-3-caboxylic acid
Scheme B, step a and step b
Prepare by a method similar to Example 38 using N-benzoyl-N-phenyl-hydrazine hydrochloride salt.

EXAMPLE 41

1-[5-Methoxy-2-[(4-methoxy)phenyl]-1H-indol-3-yl]-acetic acid methyl ester
Scheme B, step a and step b followed by optional step c
Combine N-(4-methoxyphenyl)-hydrazine hydrochloride salt (12.22 g, 70 mmol), sodium acetate (5.74 g, 70 mmol), and p-methoxybenzoyl-propionic acid (19 g, 90 mmol) in methanol (100 mL). After 3 hours, cool to 0° C. and saturate with hydrogen chloride gas. Heat to reflux for 4 hours, cool to ambient temperature and evaporate in vacuo to obtain a residue. Chromatograph the residue on silica gel eluting with 50% ethyl acetate/hexane to give the title compound.

EXAMPLE 42

1-Benzoyl-2-[4-(methoxy)phenyl]-1H-indole-3-caboxylic acid
Scheme B, step a and step b
Prepare by a method similar to Example 41 using N-benzoyl-N-phenyl-hydrazine hydrochloride salt.

EXAMPLE 43

1-[5-Methyl-2-[(4-methoxy)phenyl]-1H-indol-3-yl]-acetic acid methyl ester
Scheme B, step a and step b followed by optional step c
Prepare by a method similar to Example 41 using N-p-tolyl-hydrazine hydrochloride salt.

EXAMPLE 44

1-[5-Methoxy-2-methyl-1H-indol-3-yl]-acetic acid methyl ester
Scheme B, step a and step b followed by optional step c
Combine N-(4-methoxyphenyl)-hydrazine hydrochloride salt (5.36 g, 30.7 mmol), and levulinic acid methyl ester (4.3 g, 30.7 mmol) in methanol (100 mL). After 24 hours, Add hydrochloric acid in dioxane (7.7 mL, 4M 31 mmol). Heat to reflux for 4 hours, cool to ambient temperature and evaporate in vacuo to obtain a residue. Chromatograph the residue on silica gel eluting with 50% ethyl acetate/hexane to give the title compound.

EXAMPLE 45

1-[5-Chloro-2-methyl-1H-indol-3-yl]-acetic acid methyl ester
Scheme B, step a and step b followed by optional step c
Prepare by a method similar to Example 41 using N-(-chlorophenyl)hydrazine hydrochloride salt.

EXAMPLE 46

5-Chloro-1H-indole-3-carboxylic acid methyl ester
Scheme B, optional step c
Combine 5-chloro-1H-indole-3-carboxylic acid (Aldrich Chemical Co.) (100 mmol) and methanol (200 mL). Add sulfuric acid (1 mL). After 24 hours, Partition the reaction mixture between ethyl acetate and a saturated sodium bicarbonate solution. Dry the organic layer over $MgSO_4$, filter and evaporate in vacuo to give a residue. Chromatograph the residue on silica gel to give the title compound.

EXAMPLE 47

5-Methoxy-1H-indole-3-carboxylic acid methyl ester
Scheme B, optional step c
Prepare by a method similar to Example 46 using 5-methoxy-1H-indole-3-carboxylic acid (Aldrich Chemical Co.).

EXAMPLE 48

1-[5-Methoxy-1-methyl-2-[(4-methoxy)phenyl]-1H-indol-3-yl]-acetic acid methyl ester
Scheme B, optional modification step d
Combine 1-[5-Methoxy-2-[(4-methoxy)phenyl]-1H-indol-3-yl]-acetic acid methyl ester (2.0 g, 6.2 mmol) and dimethylformamide (20 mL). Cool to −10° C. before adding sodium hydride (0.27 g, 60% in oil, 6.7 mmol). Stir until gas evolution ceases. Add methyl iodide (0.8 mL, 12.5 mmol). Warm to ambient temperature. After 18 hours, partition the reaction mixture between ethyl acetate and a saturated sodium chloride solution. Dry the organic layer over $MgSO_4$, filter, and evaporate in vacuo to give a residue. Chromatograph the residue on silica gel eluting with 33% ethyl acetate/hexane to give the title compound.

EXAMPLE 49

1-[5-Methoxy-1-methyl-2-methyl-1H-indol-3-yl]-acetic acid methyl ester
Scheme B. optional modification step d
Prepare by a method similar to Example 48 using 1-[5-methoxy-2-methyl-1H-indol-3-yl]-acetic acid methyl ester.

EXAMPLE 50

5-Chloro-1-methyl-1H-indole-3-carboxylic acid methyl ester
Scheme B, optional modification step d
Prepare by a method similar to Example 48 using 5-chloro-1H-indole-3-carboxylic acid methyl ester.

EXAMPLE 51

5-Methoxy-1-methyl-1H-indole-3-carboxylic acid methyl ester
Scheme B, optional modification step d
Prepare by a method similar to Example 48 using 5-methoxy-1H-indole-3-carboxylic acid methyl ester.

EXAMPLE 52

1-[5-Methoxy-1-benzyl-2-[(4-methoxy)phenyl]-1H-indol-3-yl]-acetic acid methyl ester
Scheme B, optional modification step d
Prepare by a method similar to Example 48 using 1-[5-methoxy-2-[(4-methoxy)phenyl]-1H-indol-3-yl]-acetic acid methyl ester and benzyl bromide.

EXAMPLE 53

1-(5-Methoxy-1-benzyl-2-methyl-1H-indol-3-yl]-acetic acid methyl ester
Scheme B, optional modification step d Prepare by a method similar to Example 48 using 1-[5-methoxy-2-methyl-1H-indol-3-yl]-acetic acid methyl ester and benzyl bromide.

EXAMPLE 54

5-Chloro-1-benzyl-1H-indole-3-carboxylic acid methyl ester

Scheme B, optional modification step d

Prepare by a method similar to Example 48 using 5-chloro-1H-indole-3-carboxylic acid methyl ester and benzyl bromide.

EXAMPLE 55

5-Methoxy-1-benzyl-1H-indole-3-carboxylic acid methyl ester

Scheme B, optional modification step d

Prepare by a method similar to Example 48 using 5-methoxy-1H-indole-3-carboxylic acid methyl ester and benzyl bromide.

EXAMPLE 56

1-[5-Chloro-1-ethyl-2-methyl-1H-indol-3-yl]-acetic acid methyl ester

Scheme B, optional modification step d

Prepare by a method similar to Example 48 using 1-[5-chloro-2-methyl-1H-indol-3-yl]-acetic acid methyl ester and ethyl bromide.

EXAMPLE 57

1-[5-Methyl-1-[(4-methyl)benzyl]-2-[(4-methoxy)phenyl]-1H-indol-3-yl]-acetic acid methyl ester Scheme B, optional modification step d Prepare by a method similar to Example 48 using 1-[5-methyl-2-[(4-methoxy)phenyl]-1H-indol-3-yl]-acetic acid methyl ester and 4-methylbenzyl bromide.

EXAMPLE 58

1-[5-Methoxy-1-methyl-2-[(4-methoxy)phenyl]-1H-indol-3-yl]-acetic acid

Scheme B, optional deprotection step d

Combine 1-[5-methoxy-1-methyl-2-[(4-methoxy)phenyl]-1H-indol-3-yl]-acetic acid methyl ester (1.9 g, 5.8 mmol) and lithium hydroxide (10 mL, 1M in water, 10 mmol) in tetrahydrofuran (20 mL). After 48 hours, pour the reaction mixture into 1M hydrochloric acid solution (20 mL) and extract with ethyl acetate. Dry the organic layer over MgSO$_4$, filter, and evaporate in vacuo to give the title compound.

EXAMPLE 59

5-Chloro-1-methyl-1H-indole-3-carboxylic acid

Scheme B, optional deprotection step d

Prepare by a method similar to Example 58 using 5-chloro-1-methyl-1H-indole-3-carboxylic acid methyl ester.

EXAMPLE 60

5-Methoxy-1-methyl-1H-indole-3-carboxylic acid

Scheme B, optional deprotection step d

Prepare by a method similar to Example 58 using 5-methoxy-1-methyl-1H-indole-3-carboxylic acid methyl ester.

EXAMPLE 61

5-Chloro-1-benzyl-1H-indole-3-carboxylic acid

Scheme B, optional deprotection step d

Prepare by a method similar to Example 58 using 5-Chloro-1-benzyl-1H-indole-3-carboxylic acid methyl ester.

EXAMPLE 62

5-Methoxy-1-benzyl-1H-indole-3-carboxylic acid

Scheme B, optional deprotection step d

Prepare by a method similar to Example 57 using 5-methoxy-1-benzyl-1H-indole-3-carboxylic acid methyl ester.

EXAMPLE 63

1-(5-Methoxy-1-benzyl-2-[(4-methoxy)phenyl]-1H-indol-3-yl]-acetic acid

Scheme B, optional deprotection step d

Prepare by a method similar to Example 57 using 1-[5-methoxy-1-benzyl-2-[(4-methoxy)phenyl]-1H-indol-3-yl]-acetic acid methyl ester.

EXAMPLE 64

1-[5-Methoxy-1-methyl-2-methyl-1H-indol-3-yl]-acetic acid

Scheme B, optional deprotection step d

Prepare by a method similar to Example 57 using 1-[5-methoxy-1-methyl-2-methyl-1H-indol-3-yl]-acetic acid methyl ester.

EXAMPLE 65

1-[5-Chloro-1-ethyl-2-methyl-1H-indol-3-yl]-acetic acid

Scheme B, optional deprotection step d

Prepare by a method similar to Example 57 using 1-[5-chloro-1-ethyl-2-methyl-1H-indol-3-yl]-acetic acid methyl ester.

EXAMPLE 66

1-[5-Methyl-1-[(4-methyl)benzyl]-2-[(4-methoxy)phenyl]-1H-indol-3-yl]-acetic acid Scheme B, optional deprotection step d Prepare by a method similar to Example 57 using [5-methyl-1-[(4-methyl)benzyl]-2-[(4-methoxy)phenyl]-1H-indol-3-yl]-acetic acid methyl ester.

EXAMPLE 67

8-(t-Butoxycarbonyl)amino-octanoic acid

Scheme C, step a

Combine 8-amino-octanoic acid (5.9 g, 34 mmol), triethylamine (5.0 mL, 30 mmol), and di-t-butyl dicarbonate (7.5 g, 34 mmol) in tetrahydrofuran (100 mL). After 24 hours, partition the reaction mixture between ethyl acetate and 1M hydrochloric acid solution. Dry the organic layer ove MgSO$_4$, filter and evaporate in vacuo to give the title compound.

EXAMPLE 68

12-(t-Butoxycarbonyl)amino-dodecanoic acid

Scheme C, step a

Prepare by a method similar to Example 67 using 12-amino-dodecanoic acid.

EXAMPLE 69

6-(t-Butoxycarbonyl)amino-hexanoic acid

Scheme C, step a

Prepare by a method similar to Example 67 using 6-amino-hexanoic acid.

EXAMPLE 70

8-(t-Butoxycarbonyl)amino-octanoic acid methyl-butyl-amide

Scheme C, step b

Combine 8-(t-butoxycarbonyl)amino-octanoic acid (1.28 g, 5 mmol), N-methylmorpholine (1.2 mL, 10 mmol), 1-(3-dimethylaminopropyl)-3-ethyl carbodiimide hydrochloride salt (0.95 g, 5.0 mmol), methyl-butyl amine hydrochloride salt (5.0 mmol), and 4-hydroxybenztriazole hydrate (0.05 g) in dichloromethane (20 mL). After 4 hours, add water and extract with ethyl acetate. Dry the organic layer over $MgSO_4$ and evaporate in vacuo to give the title compound.

EXAMPLE 71

8-(t-Butoxycarbonyl)amino-octanoic acid butyl-amide

Scheme C, step b

Prepare by a method similar to Example 70 using butylamine.

EXAMPLE 72

6-(t-Butoxycarbonyl)amino-hexanoic acid methyl-butyl-amide

Scheme C, step b

Prepare by a method similar to Example 70 using 6-(t-butoxycarbonyl)amino-hexanoic acid.

EXAMPLE 73

8-(t-Butoxycarbonyl)-N-methylamino-octanoic acid methyl-butyl-amide

Scheme C, step b

Prepare by a method similar to Example 70 using 8-(t-butoxycarbonyl)-N-methylamino-octanoic acid.

EXAMPLE 74

12-(t-Butoxycarbonyl)amino-dodecanoic acid butyl-methyl-amide

Scheme C, step b

Prepare by a method similar to Example 70 using 12-(t-butoxycarbonyl)amino-dodecanoic acid.

EXAMPLE 75

1-(t-Butoxycarbonyl)amino-acetic acid butyl-methyl-amide

Scheme C, step b

Prepare by a method similar to Example 70 using 1-(t-butoxycarbonyl)amino-acetic acid, (t-butoxycarbonyl-gylcine).

EXAMPLE 76

8-(t-Butoxycarbonyl)amino-octanoic acid butyl-octyl-amide

Scheme C, step b

Prepare by a method similar to Example 70 using butyl-octyl amine.

EXAMPLE 77

8-(t-Butoxycarbonyl)amino-octanoic acid methyl-amide

Scheme C, step b

Prepare by a method similar to Example 70 using methyl amine.

EXAMPLE 78

8-(t-Butoxycarbonyl)amino-octanoic acid dimethyl-amide

Scheme C, step b

Prepare by a method similar to Example 70 using dimethyl amine.

EXAMPLE 79

8-(t-Butoxycarbonyl)amino-octanoic acid dibutyl-amide

Scheme C, step b

Prepare by a method similar to Example 70 using dibutylamine.

EXAMPLE 80

8-Amino-octanoic acid methyl-butyl-amide

Scheme C, step c

Combine 8-(t-butoxycarbonyl)amino-octanoic acid methyl-butyl-amide and 4M hydrochloric acid in dioxane (10 mL). After 1 hour, the reaction mixture is evaporated to a residue. Partition the residue between toluene and 1M sodium hydroxide solution. Extract the aqueous layer with toluene. Combine the organic layers, dry over $MgSO_4$, and filter to give the title compound as a toluene solution. Evaporate in vacuo to give the title compound.

EXAMPLE 81

8-Amino-octanoic acid methyl-butyl-amide hydrochloric acid salt

Scheme C, step c

Combine 8-(t-butoxycarbonyl)amino-octanoic acid methyl-butyl-amide and 4M hydrochloric acid in dioxane (10 mL). After 1 hour, the reaction mixture is evaporated in vacuo to give a residue. Triturate the residue with diethyl ether to give a solid. Collect the solid by filtration and dry in vacuo to give the title compound.

EXAMPLE 82

8-Amino-octanoic acid butyl-amide hydrochloric acid salt

Scheme C, step c

Prepare by a method similar to Example 81 using 8-(t-butoxycarbonyl)amino-octanoic acid butyl-amide.

EXAMPLE 83

12-Amino-dodecanoic acid butyl-methyl-amide hydrochloric acid salt

Scheme C, step c

Prepare by a method similar to Example 81 using 12-(t-butoxycarbonyl)amino-dodecanoic acid butyl-methyl-amide.

EXAMPLE 84

1-Amino-acetic acid butyl-methyl-amide hydrochloric acid salt

Scheme C, step c

Prepare by a method similar to Example 81 using 1-(t-butoxycarbonyl)amino-acetic acid butyl-methyl-amide.

EXAMPLE 85

6-Amino-hexanoic acid butyl-methyl-amide hydrochloric acid salt

Scheme C, step c

Prepare by a method similar to Example 81 using 6-(t-butoxycarbonyl)amino-hexanoic acid butyl-methyl-amide.

EXAMPLE 86

8-N-Methylamino-octanoic acid methyl-butyl-amide hydrochloric acid salt

Scheme C, step c

Prepare by a method similar to Example 81 using 8-(t-butoxycarbonyl)-N-methylamino-octanoic acid methyl-butyl-amide.

EXAMPLE 87

8-Amino-octanoic acid butyl-octyl-amide hydrochloric acid salt

Scheme C, step b

Prepare by a method similar to Example 81 using 8-(t-butoxycarbonyl)amino-octanoic acid butyl-octyl-amide.

EXAMPLE 88

8-Amino-octanoic acid methyl-amide hydrochloric acid salt

Scheme C, step b

Prepare by a method similar to Example 81 using 8-(t-butoxycarbonyl)amino-octanoic acid methyl-amide.

EXAMPLE 89

8-Amino-octanoic acid dimethyl-amide hydrochloric acid salt

Scheme C, step b

Prepare by a method similar to Example 81 using 8-(t-butoxycarbonyl)amino-octanoic acid dimethyl-amide.

EXAMPLE 90

8-Amino-octanoic acid dibutyl-amide hydrochloric acid salt

Scheme C, step b

Prepare by a method similar to Example 81 using 8-(t-butoxycarbonyl)amino-octanoic acid dibutyl-amide.

EXAMPLE 91

8-(t-Butoxycarbonyl)-N-methylamino-octanoic acid

Scheme C, optional step d

Combine 8-(t-butoxycarbonyl)amino-octanoic acid (100 mmol) and sodium hydride (220 mmol) in tetrahydrofuran (250 mL). Stir until gas evolution ceases. Add methyl iodide (13.64 mL). After 3 hours, partition the reaction mixture between ethyl acetate and water, adjust the pH to 4 and extract. Dry the organic layer over $MgSO_4$, filter and evaporate in vacuo to give the title compound.

EXAMPLE 92

8-(t-Butoxycarbonyl)-N-methylamino-octanoic acid butyl-methyl-amide

Scheme C, optional step e

Combine 8-(t-butoxycarbonyl)amino-octanoic acid butyl-methyl-amide (10 mmol) and sodium hydride (11 mmol) in tetrahydrofuran (25 mL). Stir until gas evolution ceases. Add methyl iodide (11 mmol). After 24 hours, partition the reaction mixture between ethyl acetate and water, adjust the pH to 4 and extract. Dry the organic layer over $MgSO_4$, filter and evaporate in vacuo to give the title compound.

EXAMPLE 93

8-N-Butylamino-octanoic acid methyl-butyl-amide

Scheme C, optional step f

Combine 8-amino-octanoic acid methyl-butyl-amide (5 mmol) in methanol (50 mL) and add butyraldehyde (5 mmol), sodium cyanoborohydride (5 mmol) and 1 drop of 1% bromocresol green in ethanol. Maintain the pH of the reaction with 1N hydrochloric acid in methanol until the indicator no longer changes. Evaporate the in vacuo and partition the residue between 1N sodium hydroxide (50 mL) and ethyl acetate (100 mL). Separate the organic phase, dry ($MgSO_4$) and evaporate the solvent in vacuo to give the the title compound.

EXAMPLE 104

Ethyl [1-benzyl-indol-3-yl]-acetate

Scheme B, optional modification step d

Combine sodium hydride (1.08 g, 60% in oil, 27.1 mmol) and dimethylformamide (50 mL). Add a solution of ethyl indol-3-yl-acetic acid (5 g, 24.6 mmol) in dimethylformamide (20 mL). Stir until gas evolution ceases. Add benzyl bromide (5.85 mL, 49.2 mmol). Warm to ambient temperature. After 48 hours, partition the reaction mixture between ethyl acetate and water. Separate the organic layer and extract with a saturated sodium chloride solution. Dry the organic layer over $MgSO_4$, filter, and evaporate in vacuo to give a residue. Chromatograph the residue on silica gel eluting with 10% ethyl acetate/hexane to give the title compound.

EXAMPLE 105

[1-Benzyl-indol-3-yl]-acetic acid

Scheme B, optional deprotection step d

Combine ethyl [1-benzyl-indol-3-yl]-acetate (3.78 g, 13.5 mmol) and lithium hydroxide (0.91 g, 21.6 mmol) in water (5.5 mL) and tetrahydrofuran (20 mL). After 60 hours, pour the reaction mixture into 1M hydrochloric acid solution (20 mL) and extract with ethyl acetate. Dry the organic layer over $MgSO_4$, filter and evaporate in vacuo to give the title compound.

EXAMPLE 106

8-[1-benzyl-1H-indol-3-yl]-acetylamino]-octanoic acid methyl-butyl-amide

Scheme A, step a

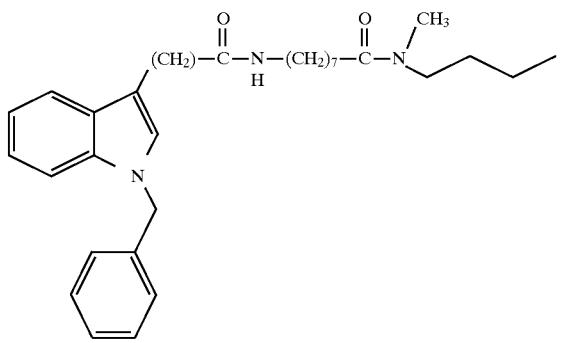

Prepare by a method similar to Example 3 using [1-benzyl-1H-indol-3-yl]-acetic acid.

EXAMPLE 107

8-(t-Butoxycarbonyl)amino-octanoic acid diethyl-amide

Scheme C, step b

Prepare by a method similar to Example 70 using diethylamine.

EXAMPLE 108

8-Amino-octanoic acid diethyl-amide hydrochloric acid salt

Scheme C, step c

Prepare by a method similar to Example 81 using 8-(t-butoxycarbonyl)amino-octanoic acid diethyl-amide.

EXAMPLE 109

8-[[5-Methoxy-1-(4-chlorobenzoyl)-2-methyl-1H-indol-3-yl]-acetylamino]-octanoic acid diethyl-amide Scheme A, step a

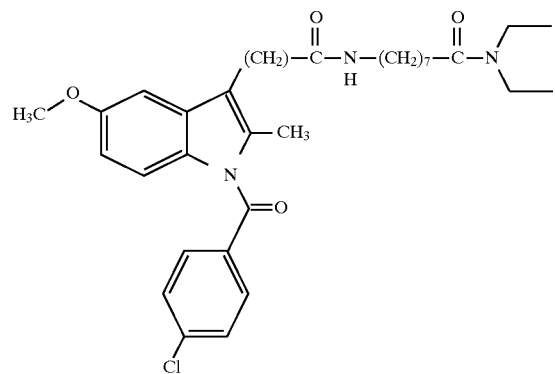

Prepare by a method similar to Example 3 using 8-amino-octanoic acid diethyl-amide hydrochloric acid salt.

EXAMPLE 110

8-[[5-Hydroxy-1-(4-chlorobenzoyl)-2-methyl-1H-indol-3-yl]-acetylamino]-octanoic acid diethyl-amide Scheme A, optional deprotection step b

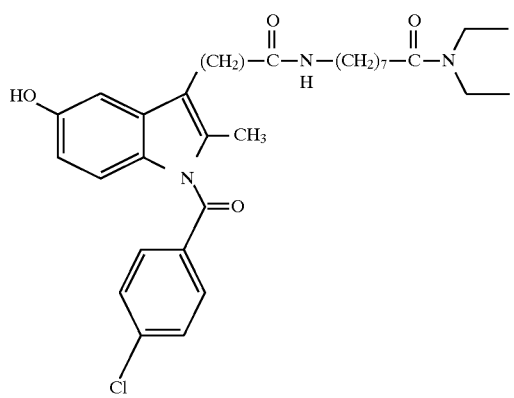

Prepare by a method similar to Example 27 using 8-[[5-methoxy-1-(4-chlorobenzoyl)-2-methyl-1H-indol-3-yl]-acetylamino]-octanoic acid diethyl-amide.

EXAMPLE 111

8-(t-Butoxycarbonyl)amino-octanoic acid pyrrolidine-amide

Scheme C, step b

Prepare by a method similar to Example 70 using pyrrolidine.

EXAMPLE 112

8-Amino-octanoic acid pyrrolidine-amide hydrochloric acid salt

Scheme C, step c

Prepare by a method similar to Example 81 using 8-(t-butoxycarbonyl)amino-octanoic acid pyrrolidine-amide.

EXAMPLE 113

8-[[5-Methoxy-1-(4-chlorobenzoyl)-2-methyl-1H-indol-3-yl]-acetylamino]-octanoic acid pyrrolidine-amide Scheme A, step a

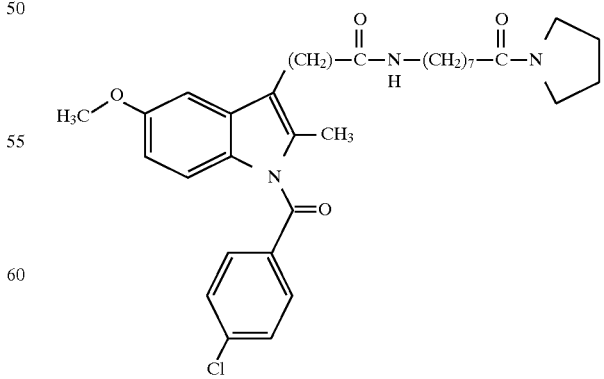

Prepare by a method similar to Example 3 using 8-amino-octanoic acid pyrrolidine-amide hydrochloric acid salt.

EXAMPLE 114

8-[[5-Hydroxy-1-(4-chlorobenzoyl)-2-methyl-1H-indol-3-yl]-acetylamino]-octanoic acid pyrrolidine-amide Scheme A, optional deprotection step b

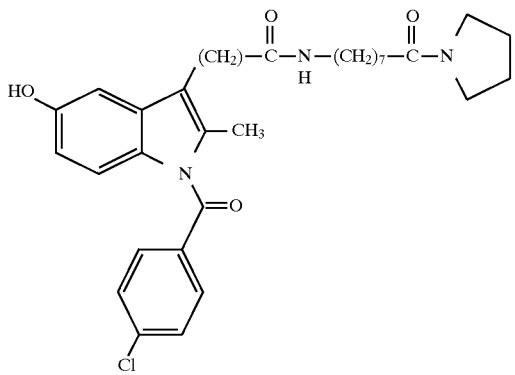

Prepare by a method similar to Example 27 using 8-[[5-methoxy-1-(4-chlorobenzoyl)-2-methyl-1H-indol-3-yl]-acetylamino]-octanoic acid pyrrolidine-amide.

EXAMPLE 115 t-Butyl [5-methoxy-2-methyl-indol-3-yl]-acetate

Scheme B, optional step c

Combine 5-methoxy-2-methyl-indol-3-yl-acetic acid (5.0) and toluene (50 mL). Heat to 65° C. Add dropwise N,N-dimethylformamide di-t-butylacetal (16.4 mL, 64.8 mmol). Heat to 80° C. After 2 hours, cool to ambient temperature and evaporate the reaction mixture in vacuo to give a residue. Partition the residue between dichloromethane and water. Separate the organic layer and extract with a saturated sodium chloride solution. Dry the organic layer over MgSO$_4$, filter, and evaporate in vacuo to give a residue. Chromatograph the residue on silica gel eluting with 1.4/1 ethyl acetate/hexane to give the title compound.

EXAMPLE 116 t-Butyl [5-methoxy-1-(4-methoxybenzoyl)-2-methyl-indol-3-yl]-acetate

Scheme B, optional modification step d

Combine sodium hydride (0.66 g, 60% in oil, 13.1 mmol) and dimethylformamide [50 mL]. Cool to 0° C. using an ice-bath. Add t-butyl (5-methoxy-2-methyl-indol-3-yl]-acetate (3 g, 10.9 mmol). Stir until gas evolution ceases. Add 4-methoxybenzoyl chloride (2.23 g, 13 mmol). Warm to ambient temperature. After 18 hours, add water. Partition the reaction mixture between ethyl acetate and water. Separate the organic layer and extract with a saturated sodium chloride solution. Dry the organic layer over MgSO$_4$, filter, and evaporate in vacuo to give a residue. Chromatograph the residue on silica gel eluting with ¼ ethyl acetate hexane to give the title compound.

EXAMPLE 117

[5-Methoxy-1-(4-methoxybenzoyl)-2-methyl-indol-3-yl]-acetic acid

Scheme B, optional deprotection step d

Combine t-butyl [5-methoxy-1-(4-methoxybenzoyl)-2-methyl-indol-3-yl]-acetate (1 g) and trifluoroacetic acid (8 mL). After 1 hours, evaporate in vacuo to give a residue. Add toluene to the residue and evaporate in vacuo to give the title compound.

EXAMPLE 118

8-[[5-Methoxy-1-(4-methoxybenzoyl)-2-methyl-1H-indol-3-yl]-acetylamino]-octanoic acid methyl-butyl-amide Scheme A, step a

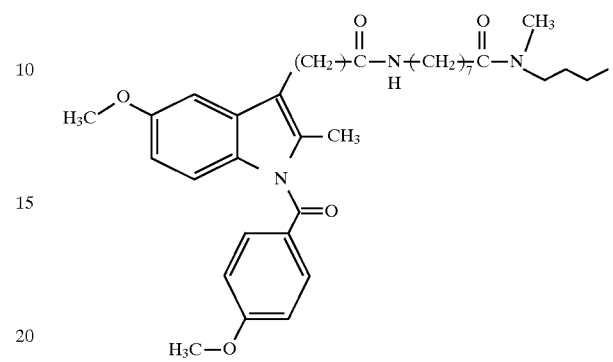

Prepare by a method similar to Example 3 using [5-methoxy-1-(4-methoxybenzoyl)-2-methyl-indol-3-yl]-acetic acid.

EXAMPLE 119

8-[[5-Hydroxy-1-(4-methoxybenzoyl)-2-methyl-1H-indol-3-yl]-acetylamino]-octanoic acid methyl-butyl-amide Scheme A, optional step b

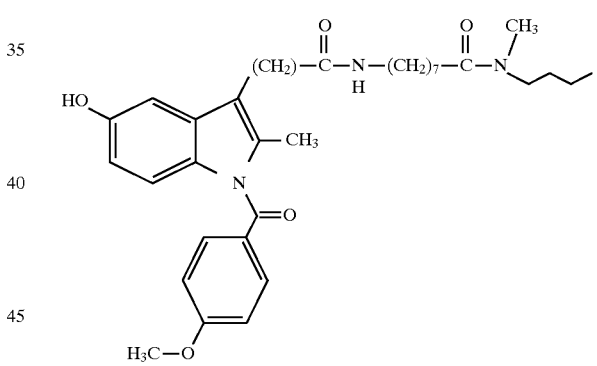

Prepare by a method similar to Example 27 using 8-[[5-Methoxy-1-(4-methoxybenzoyl)-2-methyl-1H-indol-3-yl]-acetylamino]-heptanoic acid methyl-butyl-amide.

EXAMPLE 120

7-(t-Butoxycarbonyl)amino-heptanoic acid

Scheme C, step a

Prepare by a method similar to Example 67 using 7-amino-heptanoic acid.

EXAMPLE 121

7-(t-Butoxycarbonyl)amino-heptanoic acid methyl butyl-amide

Scheme C, step b

Prepare by a method similar to Example 70 using 7-(t-butoxycarbonyl)amino-heptanoic acid.

EXAMPLE 122

7-Amino-heptanoic acid methyl butyl-amide hydrochloric acid salt

Scheme C, step c

Prepare by a method similar to Example 81 using 7-(t-butoxycarbonyl)amino-heptanoic acid methyl butyl-amide.

EXAMPLE 123 t-Butyl [5-methoxy-1-benzoyl-2-methyl-indol-3-yl]-acetate

Scheme B, optional modification step d

Prepare by a method similar to Example 116 using benzoyl chloride.

EXAMPLE 124

[5-Methoxy-1-benzoyl-2-methyl-indol-3-yl]-acetic acid

Scheme B, optional deprotection step d

Prepare by a method similar to Example 117 using t-Butyl [5-methoxy-1-benzoyl-2-methyl-indol-3-yl]-acetate.

EXAMPLE 125

7-[[5-Methoxy-1-benzoyl-2-methyl-1H-indol-3-yl]-acetylamino]-heptanoic acid methyl-butyl-amide Scheme A, step a

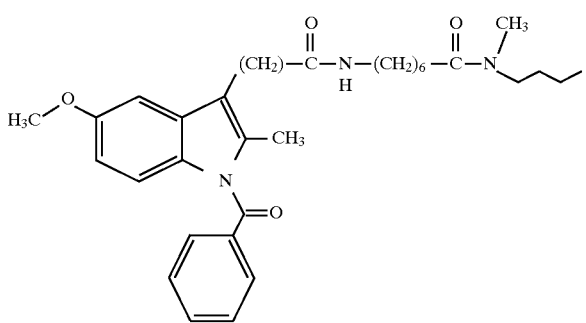

Prepare by a method similar to Example 3 using [5-methoxy-1-benzoyl-2-methyl-indol-3-yl]-acetic acid and 7-amino-heptanoic acid methyl butyl-amide hydrochloric acid salt.

EXAMPLE 126

7-[[5-Hydroxy-1-benzoyl-2-methyl-1H-indol-3-yl]-acetylamino]-heptanoic acid methyl-butyl-amide Scheme A, optional step b

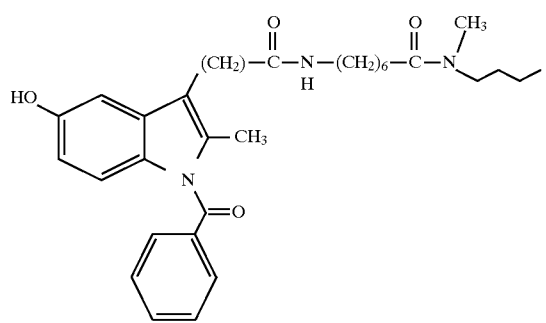

Prepare by a method similar to Example 27 using 7-[[5-methoxy-1-benzoyl-2-methyl-1H-indol-3-yl]-acetylamino]-heptanoic acid methyl-butyl-amide.

EXAMPLE 127

7-(t-Butoxycarbonyl)amino-heptanoic acid methyl phenyl-amide

Scheme C, step b

Prepare by a method similar to Example 70 using 7-(t-butoxycarbonyl)amino-heptanoic acid and N-methylaniline.

EXAMPLE 128

7-Amino-heptanoic acid methyl phenyl-amide hydrochloric acid salt

Scheme C, step c

Prepare by a method similar to Example 81 using 7-(t-butoxycarbonyl)amino-heptanoic acid methyl phenyl-amide.

EXAMPLE 129

7-[[5-Methoxy-1-benzoyl-2-methyl-1H-indol-3-yl]-acetylamino]-heptanoic acid methyl-phenyl-amide Scheme A, step a

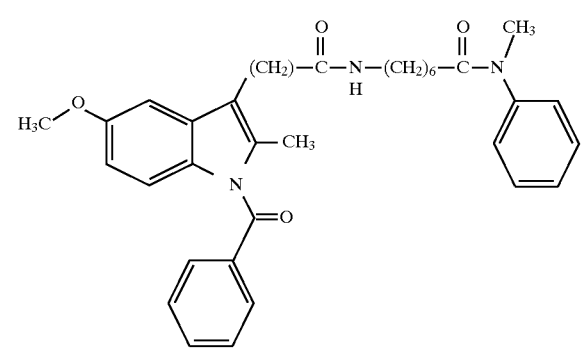

Prepare by a method similar to Example 3 using [5-methoxy-1-benzoyl-2-methyl-indol-3-yl]-acetic acid and 7-amino-heptanoic acid methyl phenyl-amide hydrochloric acid salt.

EXAMPLE 130

7-[[5-Hydroxy-1-benzoyl-2-methyl-1H-indol-3-yl]-acetylamino]-heptanoic acid methyl-phenyl-amide Scheme A, optional step b

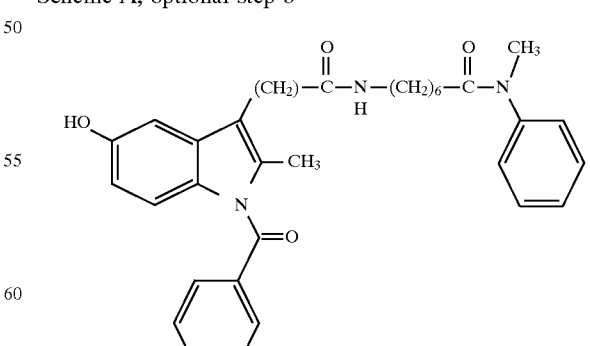

Prepare by a method similar to Example 27 using 7-[[5-methoxy-1-benzoyl-2-methyl-1H-indol-3-yl]-acetylamino]-heptanoic acid methyl-phenyl-amide.

EXAMPLE 131

7-(t-Butoxycarbonyl)amino-heptanoic acid diethyl-amide

Scheme C, step b

Prepare by a method similar to Example 70 using 7-(t-butoxycarbonyl)amino-heptanoic acid and diethylamine.

EXAMPLE 132

7-Amino-heptanoic acid diethyl-amide hydrochloric acid salt

Scheme C, step c

Prepare by a method similar to Example 81 using 7-(t-butoxycarbonyl)amino-heptanoic acid diethyl-amide.

EXAMPLE 133

7-[[5-Methoxy-1-benzoyl-2-methyl-1H-indol-3-yl]-acetylamino]-heptanoic acid diethyl-amide Scheme A, step a

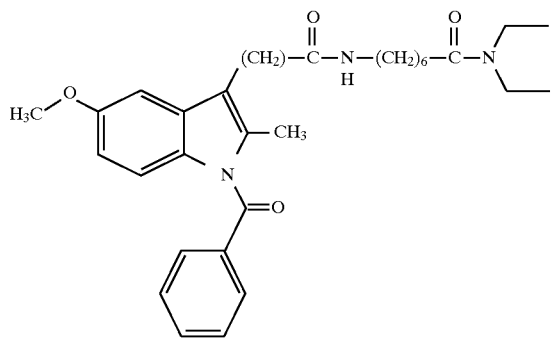

Prepare by a method similar to Example 3 using [5-methoxy-1-benzoyl-2-methyl-indol-3-yl]-acetic acid and 7-amino-heptanoic acid diethyl-amide hydrochloric acid salt.

EXAMPLE 134

7-[[5-Hydroxy-1-benzoyl-2-methyl-1H-indol-3-yl]-acetylamino]-heptanoic acid diethyl-amide Scheme A, optional step b

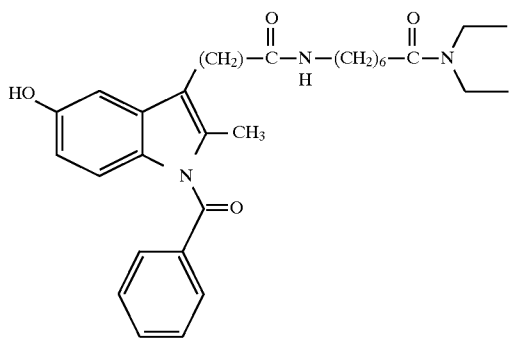

Prepare by a method similar to Example 27 using 7-[[5-methoxy-1-benzoyl-2-methyl-1H-indol-3-yl]-acetylamino]-heptanoic acid diethyl-amide.

EXAMPLE 135 t-Butyl (5-fluoro-indol-3-yl]-acetate

Scheme B, optional step c

Prepare by a method similar to Example 115 using [5-fluoro-indol-3-yl]-acetic acid.

EXAMPLE 136 t-Butyl [5-fluoro-1-benzoyl-indol-3-yl]-acetate

Scheme B, optional modification step d

Prepare by a method similar to Example 116 using t-butyl [5-fluoro-indol-3-yl]-acetate and benzoyl chloride.

EXAMPLE 137

[5-fluoro-1-benzoyl-indol-3-yl]-acetic acid

Scheme B, optional deprotection step d

Prepare by a method similar to Example 117 using t-butyl [5-fluoro-1-benzoyl-indol-3-yl]-acetate.

EXAMPLE 138

7-[[5-fluoro-1-benzoyl-1H-indol-3-yl]-acetylamino]-heptanoic acid diethyl-amide

Scheme A, step a

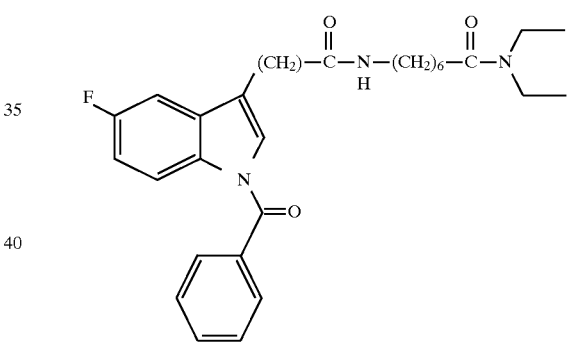

Prepare by a method similar to Example 3 using [5-fluoro-1-benzoyl-indol-3-yl]-acetic acid and 7-amino-heptanoic acid diethyl-amide hydrochloric acid salt.

EXAMPLE 139 t-Butyl [5-methoxy-1-(3-phenylpropionyl)-2-methyl-indol-3-yl]-acetate

Scheme B, optional modification step d

Prepare by a method similar to Example 116 using hydrocinnamoyl chloride.

EXAMPLE 140

[5-Methoxy-1-(3-phenylpropionyl)-2-methyl-indol-3-yl]-acetic acid

Scheme B, optional deprotection step d

Prepare by a method similar to Example 117 using t-Butyl [5-methoxy-1-(3-phenylpropionyl)-2-methyl-indol-3-yl]-acetate.

EXAMPLE 141

8-[[(5-Methoxy-1-(3-phenylpropionyl)-2-methyl-1H-indol-3-yl]-acetylamino]-octanoic acid methyl-butyl-amide Scheme A, step a

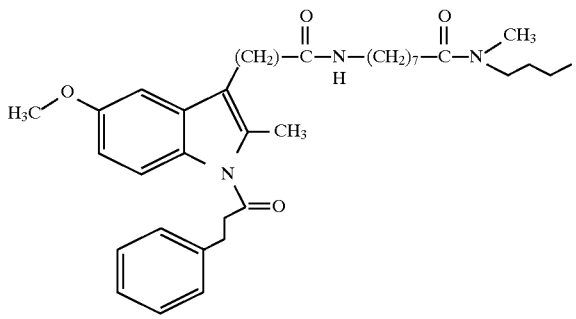

Prepare by a method similar to Example 3 using [5-methoxy-1-(3-phenylpropionyl)-2-methyl-indol-3-yl]-acetic acid and 8-amino-octnoic acid methyl butyl-amide hydrochloric acid salt.

EXAMPLE 142

8-[[5-Hydroxy-1-(3-phenylpropionyl)-2-methyl-1H-indol-3-yl]-acetylamino]-octanoic acid methyl-butyl-amide Scheme A, optional step b

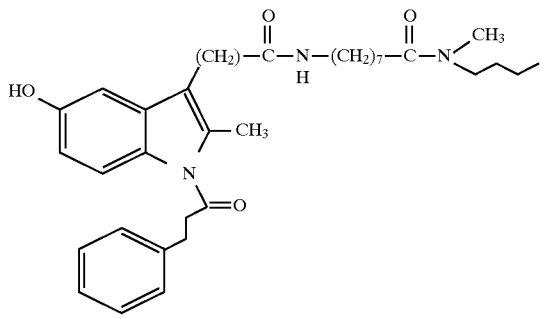

Prepare by a method similar to Example 27 using 8-[[5-methoxy-1-(3-phenylpropionyl)-2-methyl-1H-indol-3-yl]-acetylamino]-octanoic acid methyl-butyl-amide.

EXAMPLE 143

Methyl [5-methoxy-2-methyl-indol-3-yl]-acetate

Scheme B, optional step c

Combine 5-methoxy-2-methyl-indol-3-yl-acetic acid (5.34), methanol (44 mL), and aqueous 12M hydrochloric acid (2.0 mL). Heat to reflux. After 2.75 hours, cool to ambient temperature and evaporate the reaction mixture in vacuo to give a residue. Partition the residue between ethyl acetate and aqueous saturated sodium bicarbonate solution. Separate the organic layer, dry over $MgSO_4$, filter, and evaporate in vacuo to give the title compound.

EXAMPLE 144

Methyl [5-methoxy-1-(3-phenylpropyl)-2-methyl-indol-3-yl]-acetate

Scheme B, optional modification step d

Prepare by a method similar to Example 48 using methyl [5-methoxy-2-methyl-indol-3-yl]-acetate and 3-phenylpropyl bromide.

EXAMPLE 145

[5-Methoxy-1-(3-phenylpropyl)-2-methyl-indol-3-yl]-acetic acid

Scheme B, optional deprotection step d

Prepare by a method similar to Example 105 using methyl [5-methoxy-1-(3-phenylpropyl)-2-methyl-indol-3-yl-acetate.

EXAMPLE 146

7-[[5-Methoxy-1-(3-phenylpropyl)-2-methyl-1H-indol-3-yl]-acetylamino]-heptanoic acid methyl-butyl-amide Scheme A, step a

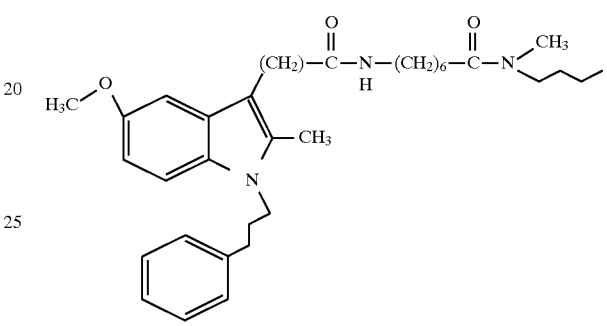

Prepare by a method similar to Example 3 using [5-methoxy-1-(3-phenylpropyl)-2-methyl-indol-3-yl]-acetic acid and 7-amino-heptanoic acid methyl butyl-amide hydrochloric acid salt.

EXAMPLE 147

7-[[5-Hydroxy-1-(3-phenylpropyl)-2-methyl-1H-indol-3-yl]-acetylamino]-heptanoic acid methyl-butyl-amide Scheme A, optional step b

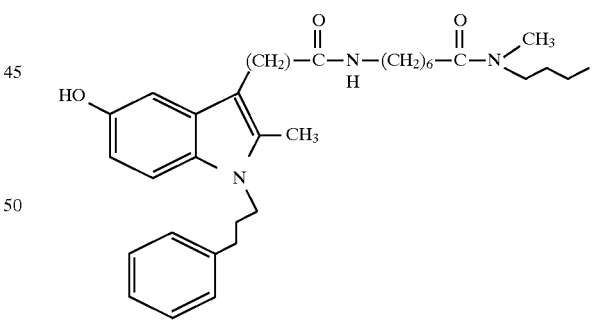

Prepare by a method similar to Example 27 using 7-[[5-methoxy-1-(3-phenylpropyl)-2-methyl-1H-indol-3-yl]-acetylamino]-heptanoic acid methyl-butyl-amide.

EXAMPLE 148

8-(t-Butoxycarbonyl)amino-octanoic acid morpholine-amide

Scheme C, step b

Prepare by a method similar to Example 70 using morpholine.

EXAMPLE 149

8-Amino-octanoic acid morpholine-amide hydrochloric acid salt

Scheme C, step c

Prepare by a method similar to Example 81 using 8-(t-butoxycarbonyl)amino-octanoic acid morpholine-amide.

EXAMPLE 150

8-[[5-Methoxy-1-(4-chlorobenzoyl)-2-methyl-1H-indol-3-yl]-acetylamino]-octanoic acid morpholine-amide Scheme A, step a

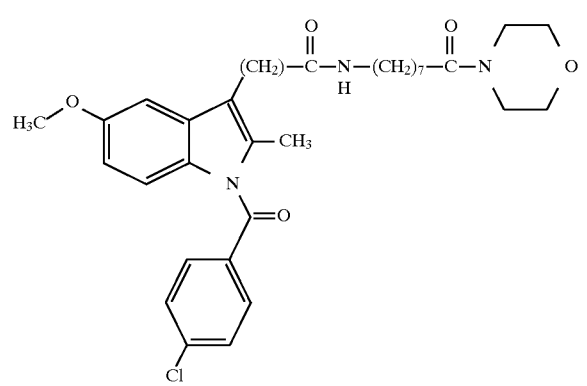

Prepare by a method similar to Example 3 using 8-amino-octanoic acid morpholine-amide hydrochloric acid salt.

EXAMPLE 151

8-[[5-Hydroxy-1-(4-chlorobenzoyl)-2-methyl-1H-indol-3-yl]-acetylamino]-octanoic acid morpholine-amide Scheme A, optional deprotection step b

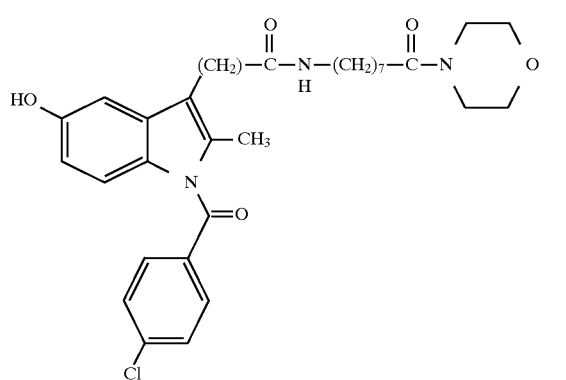

Prepare by a method similar to Example 27 using 8-[[5-methoxy-1-(4-chlorobenzoyl)-2-methyl-1H-indol-3-yl]-acetylamino]-octanoic acid morpholine-amide.

EXAMPLE 152

7-[[5-Methoxy-1-benzyl-2-[(4-methoxy)phenyl]-1H-indol-3-yl]-acetylamino]-heptanoic acid methyl butyl-amide Scheme A, step a

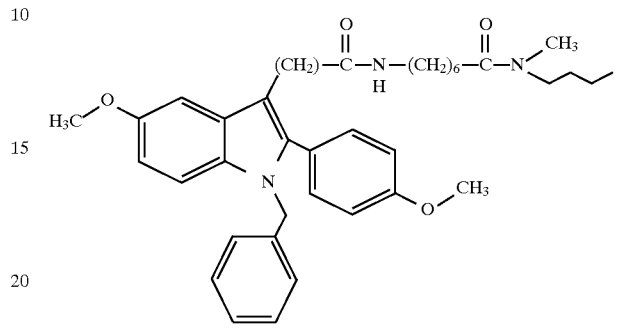

Prepare by a method similar to Example 3 using 1-[5-methoxy-1-benzyl-2-[(4-methoxy)phenyl]-1H-indol-3-yl]-acetic acid and 7-amino-heptanoic acid methyl butyl-amide hydrochloric acid salt.

EXAMPLE 153

7-[[5-Hydroxy-1-benzyl-2-[(4-hydoxy)phenyl]-1H-indol-3-yl]-acetylamino]-heptanoic acid methyl butyl-amide Scheme A, optional deprotection step b

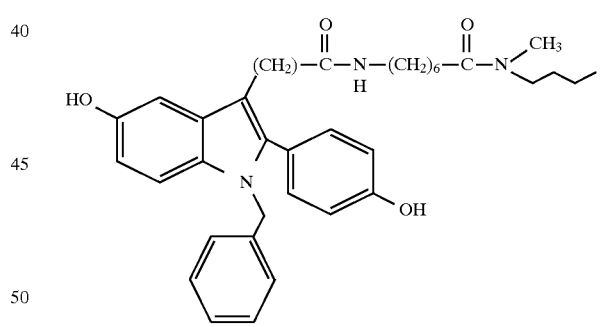

Prepare by a method similar to Example 29 using 7-[[5-methoxy-1-benzyl-2-[(4-methoxy)phenyl]-1H-indol-3-yl]-acetylamino]-heptanoic acid methyl butyl-amide.

EXAMPLE 154

6-[[5-Methoxy-1-(4-chlorobenzoyl)-2-methyl-1H-indol-3-yl]-acetylamino]-hexanoic acid methyl-butyl-amide Scheme A, step a

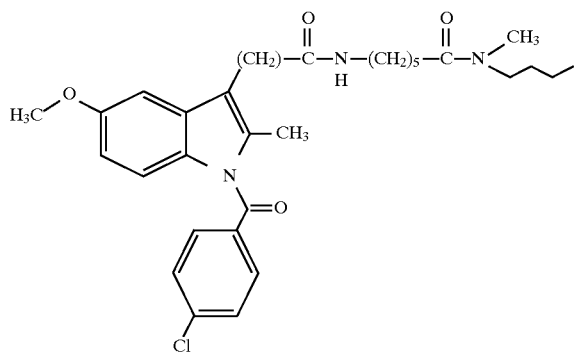

Prepare by a method similar to Example 3 using [5-methoxy-1-(4-chlorobenzoyl)-2-methyl-indol-3-yl]-acetic acid and 6-amino-hexanoic acid methyl butyl-amide hydrochloric acid salt.

EXAMPLE 155

6-[[5-Hydroxy-1-(4-chlorobenzoyl)-2-methyl-1H-indol-3-yl]-acetylamino]-hexanoic acid methyl-butyl-amide Scheme A, optional step b

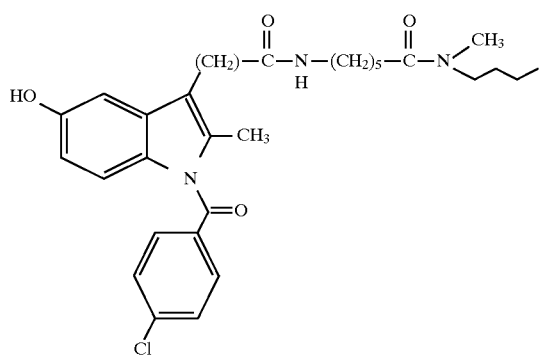

Prepare by a method similar to Example 27 using 6-[[5-methoxy-1-(4-chlorobenzoyl)-2-methyl-1H-indol-3-yl]-acetylamino]-hexanoic acid methyl-butyl-amide.

EXAMPLE 156

Methyl [5-methoxy-2-(4-fluorophenyl)-indol-3-yl]-acetate

Scheme B, step a and step b followed by optional step c

Prepare by a method similar to Example 41 using p-fluorobenzoyl-propionic acid.

EXAMPLE 157

Methyl [5-methoxy-1-benzyl-2-(4-fluorophenyl)-indol-3-yl]-acetate

Scheme B, optional modification step d

Prepare by a method similar to Example 48 using methyl [5-methoxy-2-(4-fluorophenyl)-indol-3-yl]-acetate and benzyl bromide.

EXAMPLE 158

[5-Methoxy-1-benzyl-2-(4-fluorophenyl)-indol-3-yl]-acetic acid

Scheme B, optional deprotection step d

Prepare by a method similar to Example 105 using methyl [5-methoxy-1-benzyl-2-(4-fluorophenyl)-indol-3-yl]-acetate.

EXAMPLE 159

8-[[5-Methoxy-1-benzyl-2-(4-fluorophenyl)-1H-indol-3-yl]-acetylamino]-octanoic acid methyl-butyl-amide Scheme A, step a

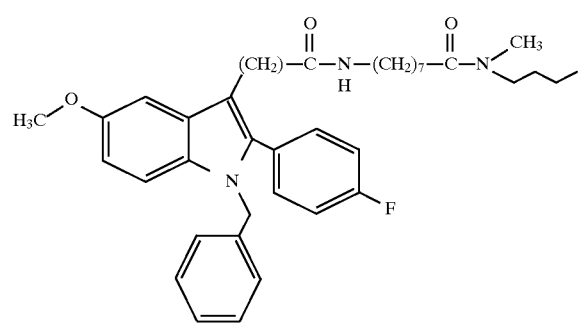

Prepare by a method similar to Example 3 using [5-methoxy-1-benzyl-2-(4-fluorophenyl)-indol-3-yl]-acetic acid and 8-amino-octanoic acid methyl butyl-amide hydrochloric acid salt.

EXAMPLE 160

8-[[5-Hydroxy-1-benzyl-2-(4-fluorophenyl)-1H-indol-3-yl]-acetylamino]-octanoic acid methyl-butyl-amide Scheme A, optional deprotection step b

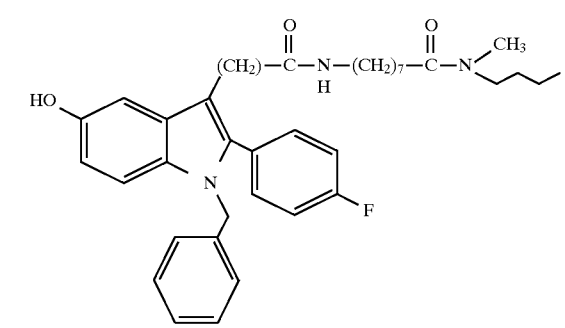

Prepare by a method similar to Example 27 using 8-[[5-methoxy-1-benzyl-2-(4-fluorophenyl)-1H-indol-3-yl]-acetylamino]-octanoic acid methyl butyl-amide.

EXAMPLE 161

7-[[5-Acetoxy-1-(3-phenylpropyl)-2-methyl-1H-indol-3-yl]-acetylamino]-heptanoic acid methyl-butyl-amide Scheme A, optional step b

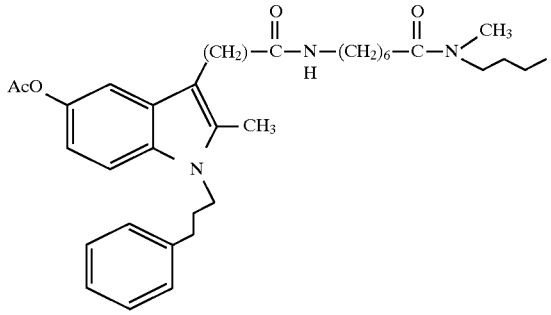

Combine 7-[[5-hydroxy-1-(3-phenylpropyl)-2-methyl-1H-indol-3-yl]-acetylamino]-heptanoic acid methyl-butyl-amide (0.22 g, 0.52 mmol) and acetic anhydride (0.12 mL, 0.11 mmol) and 4-dimethylaminopyridine (0.174 g) in dichloromethane (2.5 mL). After 18 hours, add methanol (0.5 mL) and stir for 10 minutes. Partition the reaction mixture between ethyl acetate and water. Separate the organic layer and extract with aqueous 1M hydrochloric acid solution. Dry the organic layer over $Na_2SO_4$, filter, and evaporate in vacuo to give a residue. Chromatograph the residue on silica gel eluting with ethyl acetate to give the title compound.

EXAMPLE 162

6-[[5-Methoxy-1-benzyl-2-[(4-methoxy)phenyl]-1H-indol-3-yl]-acetylamino]-hexanoic acid methyl-butyl-amide Scheme A, step a

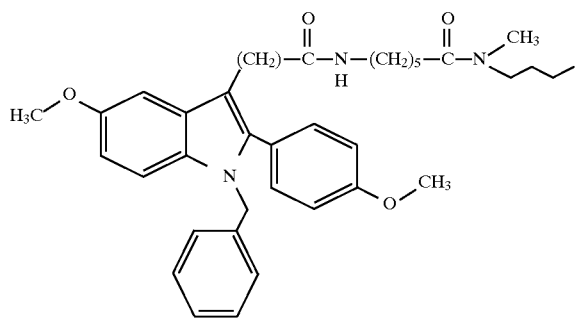

Prepare by a method similar to Example 3 using 1-[5-methoxy-1-benzyl-2-[(4-methoxy)phenyl]-1H-indol-3-yl]-acetic acid and 6-amino-hexanoic acid methyl butyl-amide hydrochloric acid salt.

EXAMPLE 163

6-[[5-Hydroxy-1-benzyl-2-[(4-hydroxy)phenyl]-1H-indol-3-yl]-acetylamino]-hexanoic acid methyl-butyl-amide Scheme A, deprotection step b

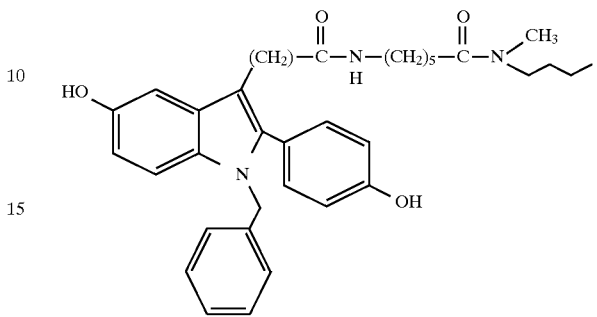

Prepare by a method similar to Example 29 using 6-[[5-methoxy-1-benzyl-2-[(4-methoxy)phenyl]-1H-indol-3-yl]-acetylamino]-hexanoic acid methyl-butyl-amide.

EXAMPLE 164

6-[[5-Acetoxy-1-benzyl-2-[(4-acetoxy)phenyl]-1H-indol-3-yl]-acetylamino]-hexanoic acid methyl-butyl-amide Scheme A, modification step b

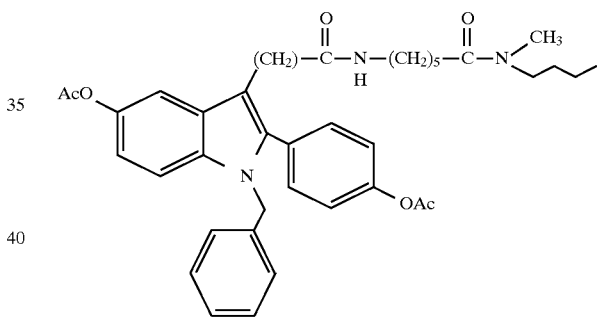

Prepare by a method similar to Example 37 using 6-[[5-hydroxy-1-benzyl-2-[(4-hydroxy)phenyl]-1H-indol-3-yl]-acetylamino]-hexanoic acid methyl-butyl-amide.

EXAMPLE 165 t-Butyl [5-methoxy-1-(carboxylic acid 4-methoxyphenyl amide)-indol-3-yl]-acetate Scheme B, optional modification step d Combine t-butyl [5-methoxy-indol-3-yl]-acetate (1.0 g, 3.6 mmol) and tetrahydrofuran (50 mL). Cool in a dry-ice acetone bath. Add n-butyllithium (1.60 mL, 2.5M in hexane, 3.99 mmol). Warm to ambient temperature. After 30 minutes, cool again in a dry-ice acetone bath. Add 4-methoxyphenyl isocyanate (0.53 mL, 3.99 mmol). Warm again to ambient temperature. After 1 hour, add aqueous saturated ammonium chloride solution. Extract with ethyl acetate. Combine the organic layers and extract with water and then a saturated sodium chloride solution. Dry the organic layer over $MgSO_4$, filter, and evaporate in vacuo to give a residue. Chromatograph the residue on silica gel eluting with ¼ ethyl acetate/hexane to give the title compound.

EXAMPLE 166

[5-Methoxy-1-(carboxylic acid 4-methoxyphenyl amide)-indol-3-yl]-acetic acid

Scheme B, optional deprotection step d

Prepare by a method similar to Example 117 using t-butyl [5-methoxy-1-(carboxylic acid 4-methoxyphenyl amide)-indol-3-yl]-acetate.

EXAMPLE 167

7-[[5-Methoxy-1-(carboxylic acid 4-methoxyphenyl amide)-1H-indol-3-yl]-acetylamino]-heptanoic acid diethyl-amide Scheme A, step a

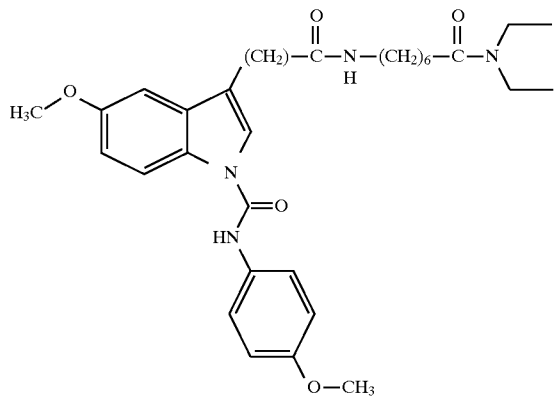

Prepare by a method similar to Example 3 using [5-methoxy-1-(carboxylic acid 4-methoxyphenyl amide)-indol-3-yl]-acetic acid and 7-amino-heptanoic acid diethyl-amide hydrochloric acid salt.

EXAMPLE 168

7-[[5-Hydroxy-1-(carboxylic acid 4-hydroxyphenyl amide)-1H-indol-3-yl]-acetylamino]-heptanoic acid diethyl-amide Scheme A, optional step b

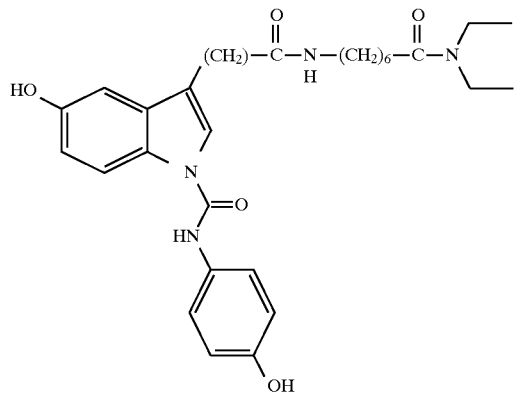

Prepare by a method similar to Example 29 using 7-[[5-methoxy-1-(carboxylic acid 4-methoxyphenyl amide)-1H-indol-3-yl]-acetylamino]-heptanoic acid diethyl-amide.

EXAMPLE 169 t-Butyl [5-methoxy-1-(carboxylic acid 4-chlorophenyl amide)-indol-3-yl]-acetate

Scheme B, optional modification step d

Prepare by a method similar to Example 165 using 4-chlorophenyl isocyanate.

EXAMPLE 170

[5-Methoxy-1-(carboxylic acid 4-chlorophenyl amide)-indol-3-yl]-acetic acid

Scheme B, optional deprotection step d

Prepare by a method similar to Example 117 using t-butyl [5-methoxy-1-(carboxylic acid 4-chlorophenyl amide)-indol-3-yl]-acetate.

EXAMPLE 171

7-[[5-Methoxy-1-(carboxylic acid 4-chlorophenyl amide)-1H-indol-3-yl]-acetylamino]-heptanoic acid diethyl-amide Scheme A, step a Prepare by a method similar to Example 3 using [5-methoxy-1-(carboxylic acid 4-chlorophenyl amide)-indol-3-yl]-acetic acid and 7-amino-heptanoic acid diethyl-amide hydrochloric acid salt.

EXAMPLE 172

7-[[5-Hydroxy-1-(carboxylic acid 4-chlorophenyl amide)-1H-indol-3-yl]-acetylamino]-heptanoic acid diethyl-amide Scheme A, optional step b

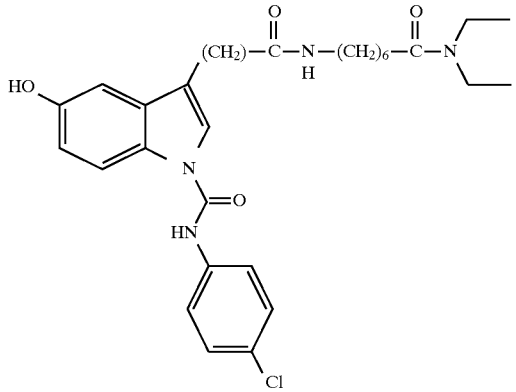

Prepare by a method similar to Example 27 using 7-[[5-methoxy-1-(carboxylic acid 4-chlorophenyl amide)-1H-indol-3-yl]-acetylamino]-heptanoic acid diethyl-amide.

EXAMPLE 173 t-Butyl [5-methoxy-1-(carboxylic acid butyl amide)-indol-3-yl]-acetate

Scheme B, optional modification step d

Prepare by a method similar to Example 165 using butyl isocyanate.

EXAMPLE 174

[5-Methoxy-1-(carboxylic acid butyl amide)-indol-3-yl]-acetic acid

Scheme B, optional deprotection step d

Prepare by a method similar to Example 117 using t-butyl [5-methoxy-1-(carboxylic acid butyl amide)-indol-3-yl]-acetate.

EXAMPLE 175

7-[[5-Methoxy-1-(carboxylic acid butyl amide)-1H-indol-3-yl]-acetylamino]-heptanoic acid diethyl-amide Scheme A, step a

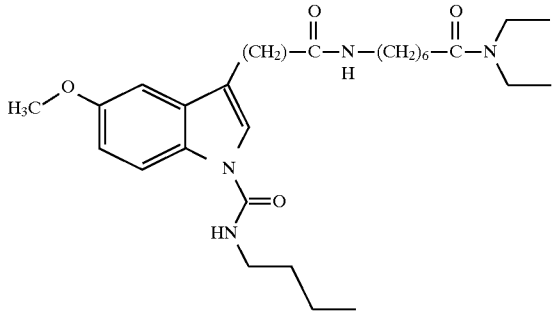

Prepare by a method similar to Example 3 using [5-methoxy-1-(carboxylic acid butyl amide)-indol-3-yl]-acetic acid and 7-amino-heptanoic acid diethyl-amide hydrochloric acid salt.

EXAMPLE 176

7-[[5-Hydroxy-1-(carboxylic acid butyl amide)-1H-indol-3-yl]-acetylamino]-heptanoic acid diethyl-amide Scheme A, optional step b

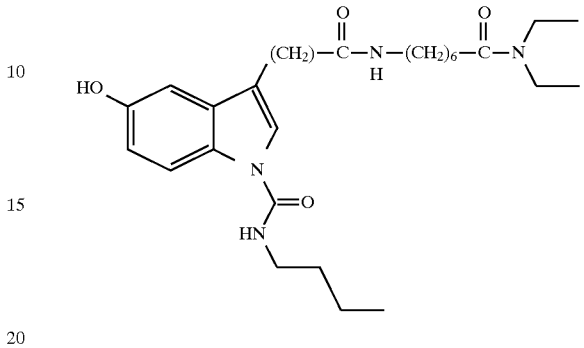

Prepare by a method similar to Example 27 using 7-[[5-methoxy-1-(carboxylic acid butyl amide)-1H-indol-3-yl]-acetylamino]-heptanoic acid diethyl-amide.

EXAMPLE 177 t-Butyl [5-methoxy-1-(4-butylbenzoyl)-2-methyl-indol-3-yl]-acetate

Scheme B, optional modification step d

Prepare by a method similar to Example 116 using 4-butylbenzoyl chloride.

EXAMPLE 178

[5-Methoxy-1-(4-butylbenzoyl)-2-methyl-indol-3-yl]-acetic acid

Scheme B, optional deprotection step d

Prepare by a method similar to Example 117 using t-butyl [5-methoxy-1-(4-butylbenzoyl)-2-methyl-indol-3-yl]-acetate.

EXAMPLE 179

7-[[5-Methoxy-1-(4-butylbenzoyl)-2-methyl-1H-indol-3-yl]-acetylamino]-heptanoic acid diethyl-amide Scheme A, step a

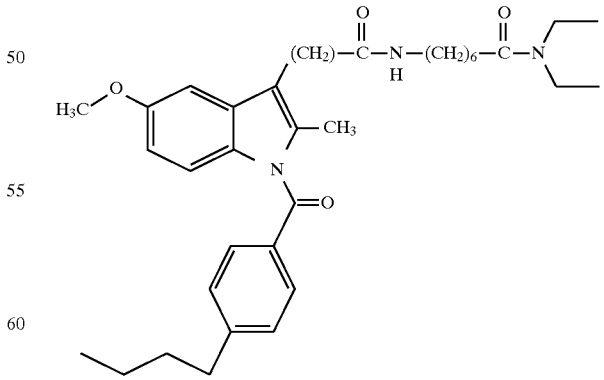

Prepare by a method similar to Example 3 using [5-methoxy-1-(4-butylbenzoyl)-2-methyl-indol-3-yl]-acetic acid and 7-amino-heptanoic acid diethyl-amide hydrochloric acid salt.

EXAMPLE 180

7-[[5-Hydroxy-1-(4-chlorobenzoyl)-2-methyl-1H-indol-3-yl]-acetylamino]-heptanoic acid diethyl-amide
Scheme A, optional deprotection step b

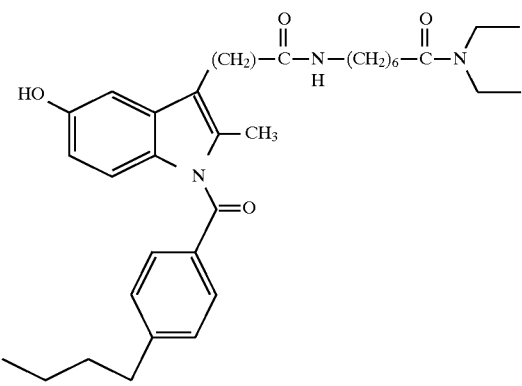

Prepare by a method similar to Example 27 using 7-[[5-methoxy-1-(4-chlorobenzoyl)-2-methyl-1H-indol-3-yl]-acetylamino]-heptanoic acid diethyl-amide.

EXAMPLE 181

8-[[5-Methoxy-2-methyl-1H-indol-3-yl]-acetylamino]-octanoic acid methyl-butyl-amide
Scheme A, step a

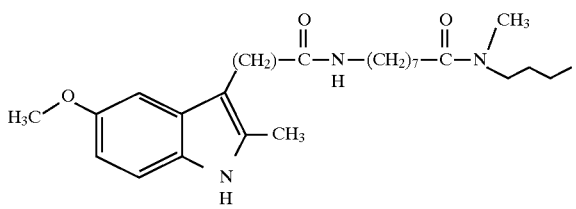

Prepare by a method similar to Example 3 using [5-methoxy-2-methyl-indol-3-yl]-acetic acid and 8-amino-octanoic acid methyl butyl-amide hydrochloric acid salt.

EXAMPLE 182

8-[[5-Hydroxy-2-methyl-1H-indol-3-yl]-acetylamino]-octanoic acid methyl-butyl-amide
Scheme A, optional deprotection step b

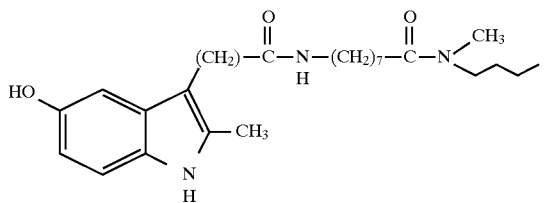

Prepare by a method similar to Example 27 using 8-[[5-methoxy-2-methyl-1H-indol-3-yl]-acetylamino]-octanoic acid methyl butyl-amide.

The present invention also provides a method of inhibiting the development of neoplasms, particularly neoplasms which exhibit uncontrolled estrogen receptor expression. More specifically, the present invention provides a method of inhibiting expression of the estrogen receptor in a patient in need thereof comprising administering to said patient a compound of the formula provided.

In a further embodiment, the present invention provides a method for the treatment of a patient afflicted with a neoplastic disease state comprising the administration thereto of a therapeutically effective antineoplastic amount of a compound of the formula provided.

The term "neoplastic disease state" as used herein refers to an abnormal state or condition characterized by rapidly proliferating cell growth or neoplasm. Neoplastic disease states for which treatment with a compound of Formula I will be particularly useful include: Leukemias such as, but not limited to, acute lymphoblastic, chronic lymphocytic, acute myeloblastic and chronic myelocytic; Carcinomas and Adenocarcinomas, such as, but not limited to, those of the cervix, breast, prostate, esophagus, stomach, small intestines, colon, cervix, ovary and lungs; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease. Neoplastic disease states for which treatment with a compound of the formula will be particularly preferred are neoplastic disease states that are estrogen-dependent including: neoplasias of the breast, ovary, uterus, and cervix.

As used herein, "a therapeutically effective antineoplastic amount" of a compound of the formula provided refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

Another embodiment of the present invention is a method of preventing estrogen-induced transcription via estrogen receptors. As such, the present invention includes a method of treating or alleviating the symptoms of diseases where overexpression of estrogen receptors or activation by estrogens causes, or contributes to symptoms related to, autoimmune diseases. Therefore, the present invention provides a method of treating, or alleviating the symptoms of, autoimmune diseases such as multiple sclerosis, rheumatoid arthritis, insulin-dependent diabetes, Graves' disease, myasthenia gravis, pemphigus vulgaris and systemic lupus erythematosus.

Based on standard clinical and laboratory tests and procedures, an attending diagnostician, as a person skilled in the art, can readily identify those patients who are in need of treatment with an agent such as a compound of the formula.

An effective amount of a compound of the formula is that amount which is effective, upon single or multiple dose administration to a patient, in providing an antitumorigenic effect. An antitumorigenic effect refers to the slowing, interrupting, inhibiting or preventing the further development of neoplastic cells. An antitumorigenic effect also refers to the slowing, interrupting, inhibiting or decreasing estrogen receptor in cells which display or have an increased risk of higher than average numbers of estrogen receptors.

An effective antitumorigenic amount of a compound of the formula can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

In a further embodiment, the present invention provides a method for the prophylactic treatment of a patient at risk of developing a neoplastic disease state comprising the administration thereto of a prophylactically effective antineoplastic amount of a compound of the formula provided.

As used herein, "a prophylactically effective antineoplastic amount" of a compound of the formula provided refers to an amount which is effective, upon single or multiple dose administration to the patient, in preventing or delaying the occurrence of the onset of a neoplastic disease state.

The identification of those patients who are in need of prophylactic treatment for neoplastic disease states is well within the ability and knowledge of one skilled in the art. The methods for identification of patients which are at risk of developing neoplastic disease states are known and appreciated in the medical arts, such as family history of the development of neoplastic disease states and the presence of risk factors associated with the development of neoplastic disease states. A clinician skilled in the art can readily identify, by the use of clinical tests, physical examination and medical/family history, those patients who are at risk of developing neoplastic disease states and thus readily determine if an individual is a patient in need of prophylactic treatment for neoplastic disease states.

An effective amount of a compound of the formula is expected to vary from about 1 microgram per kilogram of body weight per day ($\mu$g/kg/day) to about 500 mg/kg/day. Preferred amounts are expected to vary from about 0.01 to about 50 mg/kg/day.

In effecting treatment of a patient, a compound of the formula can be administered in any form or mode which makes the compound bioavailable in effective amounts, including oral and parenteral routes. For example, compounds of the formula can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, response of the patients and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like. The preferred compound of the formula is administered as a suspension in 20% DMSO/water.

In another embodiment, the present invention provides compositions comprising a compound of the formula in admixture or otherwise in association with one or more inert carriers. These compositions are useful, for example, as assay standards, as convenient means of making bulk shipments, or as pharmaceutical compositions. Inert carriers can be any material which does not degrade or otherwise covalently react with a compound of the formula. Examples of suitable inert carriers are water; aqueous buffers, such as those which are generally useful in High Performance Liquid Chromatography (HPLO) analysis; organic solvents, such as acetonitrile, ethyl acetate, hexane and the like; and pharmaceutically acceptable carriers or excipients.

More particularly, the present invention provides pharmaceutical compositions comprising a compound of the formula in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel®, corn starch and the like; lubricants such as magnesium stearate or Sterotex®; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 milligrams to 5 grams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of the formula in their end-use application. The following specific compounds of formula are especially preferred:

8-[[5-Hydroxy-1-(4-chlorobenzoyl)-2-methyl-1H-indol-3-yl]-acetylamino]-octanoic acid methyl-butyl-amide (MDL 101,906);
8-[[5-Hydroxy-1-benzyl-2-[(4-hydroxy)-phenyl]-1H-indol-3-yl]-acetylamino]-octanoic acid methyl-butyl-amide (MDL 103,324);
8-[[5-Hydroxy-1-methyl-2-[(4-hydroxy)phenyl]-1H-indol-3-yl]-acetylamino]-octanoic acid methyl-butyl-amide (MDL 103,134);
5-Hydroxy-1-methyl-1H-indole-3-carboxylic acid [8-(butyl-methyl-carbamoyl)-octyl]-amide;
8-[[5-Hydroxy-1-benzoyl-2-methyl-1H-indol-3-yl]-acetylamino]-octanoic acid methyl-butyl-amide (MDL 105,813); p0 8-[[5-Acetoxy-1-(4-chlorobenzoyl)-2-methyl-1H-indol-3-yl]-acetylamino]-octanoic acid methyl-butyl-amide;
8-[[5-Acetoxy-1-benzyl-2-[(4-acetoxy)-phenyl]-1H-indol-3-yl]-acetylamino]-octanoic acid methyl-butyl-amide (MDL 104,401);
8-[[5-Acetoxy-1-methyl-2-[(4-acetoxy)phenyl]-1H-indol-3-yl]-acetylamino]-octanoic acid methyl-butyl-amide;
8-[[5-Acetoxy-1-benzoyl-2-methyl-1H-indol-3-yl]-acetylamino]-octanoic acid methyl-butyl-amide;
7-[[5-Hydroxy-1-(4-butylbenzoyl)-2-methyl-1H-indol-3-yl]-acetylamino]-heptanoic acid diethyl-amide (MDL 103, 494);
7-[[5-Acetoxy-1-(4-butylbenzoyl)-2-methyl-1H-indol-3-yl]-acetylamino]-heptanoic acid diethyl-amide;
7-[[5-Hydroxy-1-benzoyl-2-methyl-1H-indol-3-yl]-acetylamino]-heptanoic acid methyl-phenyl-amide (MDL 103,005);
7-[[5-Acetoxy-1-benzoyl-2-methyl-1H-indol-3-yl]-acetylamino]-heptanoic acid methyl-phenyl-amide;
8-[[5-Hydroxy-1-(4-methoxybenzoyl)-2-methyl-1H-indol-3-yl]-acetylamino]-octanoic acid methyl-butyl-amide (MDL 105,517);
8-[[5-Acetoxy-1-(4-methoxybenzoyl)-2-methyl-1H-indol-3-yl]-acetylamino]-octanoic acid methyl-butyl-amide;
8-[[1-Benzyl-1H-indol-3-yl]-acetylamino]-octanoic acid methyl-butyl-amide (MDL 103,948);
8-[[5-Hydroxy-1-(4-chlorobenzoyl)-2-methyl-1H-indol-3-yl]-acetylamino]-octanoic acid diethyl-amide (MDL 104, 631);
8-[[5-Acetoxy-1-(4-chlorobenzoyl)-2-methyl-1H-indol-3-yl]-acetylamino]-octanoic acid diethyl-amide;
7-[[5-Hydroxy-1-benzyl-2-[(4-hydroxy)phenyl]-1H-indol-3-yl]-acetylamino]-heptanoic acid methyl butyl-amide (MDL 103,623);
7-[[5-Acetoxy-1-benzyl-2-[(4-acetoxy)phenyl]-1H-indol-3-yl]-acetylamino]-heptanoic acid methyl butyl-amide;
6-[[5-Hydroxy-1-(4-chlorobenzoyl)-2-methyl-1H-indol-3-yl]-acetylamino]-hexanoic acid methyl-butyl-amide (MDL 105,643);
6-[[5-Acetoxy-1-(4-chlorobenzoyl)-2-methyl-1H-indol-3-yl]-acetylamino]-hexanoic acid methyl-butyl-amide;
7-[[5-Hydroxy-1-(3-phenylpropyl)-2-methyl-1H-indol-3-yl]-acetylamino]-heptanoic acid methyl-butyl-amide (MDL 104,261);
7-[[5-Acetoxy-1-(3-phenylpropyl)-2-methyl-1H-indol-3-yl]-acetylamino]-heptanoic acid methyl-butyl-amide;
8-[[5-Hydroxy-1-benzyl-2-(4-fluorophenyl)-1H-indol-3-yl]-acetylamino]-octanoic acid methyl-butyl-amide (MDL 103,970);
8-[[5-Acetoxy-1-benzyl-2-(4-fluorophenyl)-1H-indol-3-yl]-acetylamino]-octanoic acid methyl-butyl-amide;
8-[[5-Fluoro-1-benzyl-1H-indol-3-yl]-acetylamino]-octanoic acid methyl-butyl-amide (MDL 104,822);
8-[[5-Hydroxy-1-benzyl-2-[(4-hydroxy)phenyl]-1H-indol-3-yl]-acetylamino]-octanoic acid butyl-amide (MDL 104, 262);
8-[[5-Acetoxy-1-benzyl-2-[(4-acetoxy)phenyl]-1H-indol-3-yl]-acetylamino]-octanoic acid butyl-amide;
6-[[5-Hydroxy-1-benzyl-2-[(4-hydroxy)phenyl]-1H-indol-3-yl]-acetylamino]-hexanoic acid methyl-butyl-amide (MDL 104,982);
6-[[5-Acetoxy-1-benzyl-2-[(4-acetoxy)phenyl]-1H-indol-3-yl]-acetylamino]-hexanoic acid methyl-butyl-amide.

The following studies illustrate the utility of the compounds of the formula. These studies are understood to be illustrative only and are not intended to limit the scope of the invention in any way. As used herein the following terms have the indicated meanings: "mL" refers to microliter concentration; "g" refers to gravity; "$\mu$M" refers to micromolar concentration; "Units" refers to the internationally accepted measurement of protein; "S.D." refers to standard deviation; "$\eta$mol" refers to nanomoles; "mg" refers to milligrams; "$\eta$g" refers to nanograms; "IMEM" refers to Improved Minimum Essential Medium; "ER" refers to estrogen receptor; "rpm" refers to revolutions per minute; "HBSS" refers to Hanks Balanced Salt Solution; "PCV" refers to packed cell volume.

EXAMPLE 94

Extraction of Nuclear, Cytosol, and Whole Cell Estrogen Receptors

Monolayers of MCF-7 human breast cancer cells are rinsed once with HBSS and scraped off culture dishes into 15 ml conical tubes with 5 ml HBSS. The cells are sedimented by centrifugation at 250×g for five minutes, suspended in 1 ml HBSS and sedimented by centrifugation at 2000 rpm in a tabletop centrifuge for five minutes in a 1.5 ml microfuge tube. Two PCV of a solution of a lysis buffer (25 mM HEPES, pH 7.8, 50 mM KCl, 0.5% Nonidet P 40, 2 mM dithiothreitol, 0.2 mM phenylmethylsulfonyl fluoride, 0.05 mg/ml leupeptin, 0.05 mg/ml aprotinin, 0.0025 mg/ml pepstatin, 0.005 mg/ml antipain) are added and cells are kept on ice for 15 minutes. Lysed cells are centrifuged for 3 minutes at 10,000×g, supernatant decanted, and kept as the cytosol fraction. Pellets are suspended in two PCV of extraction buffer (25 mM HEPES, pH 7.8, 500 mM KCl, 10% glycerol, 2 mM dithiothreitol and the above protease inhibitors), mixed for 20 minutes by inversion at 4 degrees C. and centrifuged at 10,000×g for 20 minutes. The supernatant is decanted and saved as nuclear extract. Both the nuclear extract and the cytosol are dialyzed for two hours against dialysis buffer (25 mM HEPES, pH 7.8, 50 mM KCl, 10% glycerol, 2 mM dithiothreitol and the above protease inhibitors). Nuclear and cytosol fractions are stored frozen at −80 degrees C. until used for mobility shift assays or determination of estrogen receptor content.

Whole cell extracts of tumor cells are prepared by the method of Reese and Katzenellenbogen, *Nuc. Acids Res.*, 19: 6595–6602 (1991), with some modifications. Cell monolayers are rinsed once with HBSS, then scraped into HBSS and sedimented by centrifugation (5 min., 250×g). After resuspending in 1 mL HBSS, the cells are again sedimented at 250×g for 5 min at 4° C. The cell pellet is resuspended in lysis/extract buffer containing 20 mM Tris, pH 7.5, 10% glycerol (v/v), 0.5M sodium chloride and 0.5% NP-40 (v/v) and incubated on ice for 25 minutes, then the supernatants are dialyzed against 25 mM HEPES, pH 7.8, 10% glycerol (v/v), 0.5 mM dithiothreitol and 50 mM potassium chloride for 2 hours at 4° C. Both the lysis/extraction and the dialysis buffers contain protease inhibitors which included 0.5 mM phenylmethylsulfonylfluoride, 0.05 mg/mL leupeptin, 0.05 mg/mL aprotinin, 0.00–25 mg/mL pepstatin, and 0.005 mg/mL antipain. Dialyzed whole cell extracts are stored in aliquots at −80° C. until used.

The protein concentration for nucleus and cytosol fractions are determined with a BIO-RAD kit, according to the manufacturer's instructions.

Quantification of Estrogen Receptors in Nuclear and Whole Cell Extracts

Estrogen receptor levels in nuclear and whole cell extracts of tumor cells were quanitated using the ER-EIA monoclonal kit manufactured by Abbott Laboratories (Diagnostic Division) according to the kit instructions.

TABLE 1

| Compound Number | $IC_{50}^*$ in $\mu M$ |
|---|---|
| 103,494 | 28† (WCE) |
| 103,005 | 27 |
| 105,517 | 16 |
| 101,906 | 19/8.6 |
| 103,948 | 14† (WCE) |
| 104,631 | 16 |
| 104,261 | 23.5 |
| 103,623 | 16/17 |
| 105,643 | 19 |
| 103,970 | 16 |
| 104,822 | 12 |
| 104,262 | 25 |
| 103,324 | 18 |
| 104,982 | 20 |
| 104,401 | 28 |

*Unless noted otherwise, $IC_{50}$ values are determined for estrogen receptors in nuclear extracts.
†WCE refers to $IC_{50}$ value for estrogen receptors in whole cell extracts.
A slash dividing two numbers indicates the results of two separate experiments.

EXAMPLE 95

Relative Binding Affinities of Indoles on Binding of Estradiol to MCF-7 Estrogen Receptor Competetive binding assays are conducted according to the procedure set forth in Katzenellenbogen J. A., et al., *Biochem.*, 12:4085–4092 (1973) to determine the Relative Binding Affinities (RBAs) of test compounds on estrogen receptor extracted from MCF-7 human breast tumor cells. Briefly, RBAs are determined from competitive binding assays with several concentrations of estradiol (E2) with and without test compound. After 16–18 hours of incubation at 4 degrees C., unbound [$^3$H] E2 is separated from ER-bound [$^3$H] E2. The $IC_{50}$ is determined and the RBA is calculated as:

RBA=$IC_{50}$ E2/$IC_{50}$ Compound×100.

MDL 101,906, 103,324 and 105,813 did not significantly inhibit estradiol binding to MCF-7 ER (inhibition was typically less than 10% at doses of 100 or 200 nM).

EXAMPLE 96

Inhibition of Estrogen Receptor Binding to an Estrogen Response Element in DNA Mobility Shift Assays DNA mobility shifts were performed according to the procedure set forth in Kumar, V. and Chambon, P., *Cell*, 55:145–156 (1988). Briefly, to each reaction tube was added 0.01 mg nuclear extract, 2 $\mu$g poly dIdC, 50 mM NaCl, 1 mM dithiothreitol and 10 mM Tris, pH 7.5 in a total volume of 0.01 ml and the mixture was kept at room temperature for 10 minutes. A $^{32}$P-labelled estrogen response element [ERE] (a 35 bp oligonucleotide containing the consensus estrogen receptor binding sequence as described in Kumar, V. and Chambon, P., *Cell*, 55:145–156 (1988) was added and incubation continued for an additional 20 minutes at room temperature. After addition of 1 $\mu$l of electrophoresis sample buffer (50% glycerol, 0.02% xylene cyanol, 0.02% bromophenol blue, 10 mM Tris pH 7.5), the samples were loaded onto 6% nondenaturing polyacrylamide gels. After electrophoresis, the gels were dried and exposed to Kodak X-OMat autoradiography film to determine the relative mobility of the bound and unbound. The gels were also analyzed quantitatively using phosphoimaging to determine the amount of radioactivity in each band on the gel.

The following results, as integrated volume of shifted ERE oligo as percentage of control, were obtained with various concentrations of MDL 101,906: 2 $\mu$M showed 81% inhibition, 5 $\mu$M showed 76% inhibition, 10 $\mu$M showed 46% inhibition and 20 $\mu$M showed 38% inhibition. The $IC_{50}$ for MDL 101,906 was 8.5 $\mu$M.

The following results, as integrated volume of shifted ERE oligo as percentage of control, were obtained with various concentrations of MDL 105,813: 2 $\mu$M showed 7.6% inhibition, 5 $\mu$M showed 60% inhibition, 10 $\mu$M showed 84% inhibition, 20 $\mu$M showed 33% inhibition and 30 $\mu$M showed 30% inhibition.

The following results, as integrated volume of shifted ERE oligo as percentage of control, were obtained with various concentrations of MDL 103,324: 2 $\mu$M showed 60% inhibition, 5 $\mu$M showed 68% inhibition, 10 $\mu$M showed 58% inhibition, 20 $\mu$M showed 46% inhibition and 30 $\mu$M showed 50% inhibition. The $IC_{50}$ for MDL 103,324 was 8.5 $\mu$M.

The following results, as integrated volume of shifted ERE oligo as percentage of control, were obtained with various concentrations of MDL 104,401: 2 $\mu$M showed 120% inhibition, 5 $\mu$M showed 92% inhibition, 10 $\mu$M showed 59% inhibition, 20 $\mu$M showed 49% inhibition and 30 $\mu$M showed 44% inhibition. The $IC_{50}$ for MDL 103,324 was 18 $\mu$M.

EXAMPLE 97

Depletion of Estrogen Receptor from MCF-7 Human Breast Tumor Cells

The effect of treatment of indoles on nuclear and cystolic ERs is determined. Briefly, 5–7×10$^6$MCF-7 cells are added to 150 mm culture dishes and allowed to grow for 48 hours in IMEM supplemented with 5% charcoal-stripped calf serum. Medium is replenished, test compounds added at concentrations ranging from 2 μM to 30 μM and cells are incubated for 24 hours. Cells are scraped and nuclear and cytosolic fractions prepared as indicated above. ER content is determined by an enzyme immunoassay (Abbott), according to manufacturer's instructions. Table 2 summarizes the results obtained.

TABLE 2

| Treatment | Nuclear ER % Control | Cytosol ER % Control |
|---|---|---|
| 2 μM MDL 101,906 | 108 | |
| 5 μM MDL 101,906 | 94 | |
| 10 μM MDL 101,906 | 81 | |
| 20 μM MDL 101,906 | 64 | 77 |
| 2 μM MDL 105,813 | 75 | |
| 5 μM MDL 105,813 | 86 | |
| 10 μM MDL 105,813 | 83 | |
| 20 μM MDL 105,813 | 53 | 33 |
| 30 μM MDL 105,813 | 37 | |
| 2 μM MDL 103,324 | 96 | |
| 5 μM MDL 103,324 | 106 | |
| 10 μM MDL 103,324 | 82 | |
| 20 μM MDL 103,324 | 56 | 36 |
| 30 μM MDL 103,324 | 37 | |

EXAMPLE 98

Inhibition of Estradiol-Stimulated Transcription of Luciferase Reporter Plasmid

The effect of MDL 101,906 on inhibition of estradiol-induced transcription was studied using an estradiol-dependent luciferase reporter plasmid in MCF-7 cells, previously described.

Construction of the estrogen reporter plasmid pVETLUC is based on previously described estrogen reporter plasmids. Shapiro, D. J., et al., Prog. Hormone Res., 45:29–64 (1989), Chambon, P., et al., Cell, 51(6):941–951 (1987). Briefly, the plasmid pVE2tk-LUC contains two copies of the vitellogenin estrogen response element (ERE), 5'-AGC TTC TTA TCC AGG TCA GCG TGA CCG TCT TAT CCA GGT CAG CGT FAC CG-3', adjacent to a 180 bp fragment encoding thymidine kinanse (tk) promoter [McKnight, S. L., and Kingsbury, R., Science 217:316–324 (1982), cloned into a pGL2-basic vector (Promega Corp.) with a luciferase (Luc) reporter gene.

Human breast tumor MCF-7 cells are transiently transfected by electroporation with either the plasmid pVETLUC and the positive control plasmid pCMVβgal (containing the β-galactosidase gene under the control of a viral enhancer) [Clontech Laboratories, Inc.; pCMBβ].

MCF-7 cells are maintained in IMEM plus 5% fetal bovine serum. On the day of electroporation, cells are trypsinized and suspended in OptiMEM at $2 \times 10^6$ cells/ml. Plasmid DNA is added to the cell suspensions (50 μg/ml pVETLUC or 20 μg/ml pCMVβgal) in an electroporation chamber (GIBCO-BRL), and subjected to a charge (500 volts/cm, 800 microfarads, 0° C., low resistance). After a 1 min recovery period, the cells are resuspended in growth medium and plated in 96-well plates at $2 \times 10^4$ cells/well. The next day, the cells are fed with serum free IMEM plus 0.1 mg/ml fibronectin, ITS+, and gentamycin. Estradiol plus or minus test compounds is added to the wells and left in the cultures for 18 to 22 hr. The cells are harvested by washing once with HBSS and adding 120 μl lysis buffer (Promega). After 20 min agitation at room temperature, the lysates are analyzed for luciferase (Promega assay system) or β-galactisidase activity (Galacto-Light assay system, Tropix) with a luminometer. $IC_{50}$ values were determined from log-log curve fits using Biolinks software (Dynatech).

MDL 101,906 inhibited estradiol-dependent transcription of an estradiol-dependent luciferase reporter plasmid in MCF-7 cells with an $IC_{50}$ of 5.2 μM. MDL 103,324 had an $IC_{50}$ of 2.7 μM. MDL 105,813 had an $IC_{50}$ of 8.4 μM.

EXAMPLE 99

Inhibition of MCF-7 Human Breast Tumor Cells and Tamoxifen-Resistant LY-2 Cells

MDL 101,906 inhibited the growth of MCF-7 and tamoxifen-resistant LY-2 cells, grown in medium supplemented with 0.001 mg/ml insulin, according to the procedure set forth in Bronzert, D. A., et al., Endocrin., 117(4):1409 (1985) with $IC_{50}$ of 3.8 and 4.7 μM, respectively.

EXAMPLE 100

Inhibition of growth of MCF-7 Cells

Intraperitoneal injections of MDL 101,906 (as a suspension in 20% DMSO/water) into female nu/nu mice 14 days after subcutaneous trocar implantation of MCF-7 tumors in the flank (approximately 3 mm³) reduced the size of the tumors compared to control mice according to the protocol set forth in Brunner, N., et al., Cancer Res., 49:1515–1520 (1989). Table 3 summarizes the results obtained.

TABLE 3

| Days after tumor implantation | Control n = 5 | 10 mg/kg n = 5 | 20 mg/kg n = 5 | 50 mg/kg n = 5 | 100 mg/kg n = 5 |
|---|---|---|---|---|---|
| 14 | 65 ± 6 | 49 ± 18 | 58 ± 9 | 77 ± 14 | 56 ± 10 |
| 22 | 147 ± 7 | 111 ± 36 | 140 ± 16 | 143 ± 13 | 81 ± 16 |
| 29 | 240 ± 18 | 155 ± 43 | 197 ± 30 | 178 ± 53 | 110 ± 24 |
| 36 | 376 ± 26 | 255 ± 70 | 282 ± 38 | 291 ± 79 | 170 ± 41 |

Treatment with MDL 101,906 resulted in a dose-dependent decrease in the tumor volume over time. The highest dose of MDL 101,906 resulted in a decrease of 55% over control 36 days after tumor implantation.

EXAMPLE 101

Reduction of Estrogen Receptor and GAPDH mRNA Levels in Treated MCF-7 Human Breast Tumor Cells Human breast tumor MCF-7 cells ($4 \times 10^6$) are grown in IMEM supplemented with 5% charcoal-stripped calf serum and insulin. After treatment with 30 μM drug for 24 hr, total RNA is isolated according to the guanidinium isothiocyanate method using an RNA preparation kit from 5 Prime-3 Prime, Inc., following the manufacturer's instructions. The RNA is separated by formaldehyde gel electrophoresis and transferred to a nylon membrane. The membrane is first hybridized with a 1.8 kb ER cDNA (sequence disclosed in Tora, L, et al., *EMBO J.* 8(7):1981–1986 (1989) and Green, S., et al., *Nature* 320:134 (1986)), stripped and then hybridized with a positive control, GAPDH probe (glyceraldehyde 3-phosphate dehydrogenase: probe sequence disclosed Tso, J. Y., et al., Nucleic Acids Res., 13(7):2485 (1985)). The intensity of the radioactive mRNA bands is determined using Molecular Dynamics Phosphoimager according to the method of Johnston, R. F., et al., *Electrophoresis* 11:355–360 (1990). The results are summarized in Table 4.

TABLE 4

| Treatment | Estrogen Receptor | GAPDH | ER/GAPDH | mean | % Control |
|---|---|---|---|---|---|
| Control 1 | 24,504 | 5,534 | 4.43 | 3.73 | 100 |
| Control 2 | 22,646 | 7,454 | 3.03 | | |
| MDL 101,906 1 | 5,142 | 5,227 | 0.98 | 0.53 | 18 |
| MDL 101,906 2 | 1,916 | 5,077 | 0.38 | | |
| MDL 103,324 1 | 5,128 | 8,300 | 0.61 | 0.74 | 20 |
| MDL 103,324 2 | 7,077 | 8,118 | 0.87 | | |
| MDL 105,813 1 | 5,288 | 6,996 | 0.75 | 0.63 | 17 |
| MDL 105,813 2 | 2,418 | 4,830 | 0.5 | | |

EXAMPLE 102

Clonigenic Assay for MCF-7 Human Breast Tumor Cells

MCF-7 cells ($10^7$) are added to 100 mm tissue culture dishes, allowed to adhere for 24 hours and then treated with either MDL 101,906 or ICI 164,384 for 24 hours. The cells are removed from the dishes with trypsin/EDTA, and washed twice by centrifugation. The cells were counted and 500 cells from each treatment group are added to triplicate wells of 6-well culture dishes. The cells are grown for 22 days. Colonies 1 mm diameter or greater are counted. The results are summarized in Table 5.

TABLE 5

| Treatment | Colonies ± S.D. | % Control |
|---|---|---|
| Control | 33 ± 7 | 100 |
| 10 μM MDL 101,906 | 30 ± 10 | 91 |
| 20 μM MDL 101,906 | 27 ± 5 | 82 |
| 50 μM MDL 101,906 | 12 ± 2 | 36 |
| 0.1 μM ICI 164,384 | 48 ± 6 | 145 |
| 1.0 μM ICI 164,384 | 40 ± 2 | 121 |

What is claimed is:

1. A compound of the formula

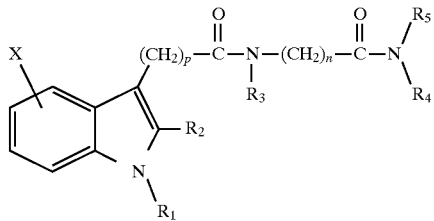

wherein n is an integer from 1 to 12;

P is 0 or 1;

X is from 1 to 3 substituents independently selected from the group consisting of hydrogen, halogen, hydroxy, $C_1$–$C_4$ alkyl, $C_1$–$C_4$ alkoxy and —OC(O)$R_6$;

$R_1$ is hydrogen, $C_1$–$C_4$ alkyl, or a radical chosen from the group consisting of

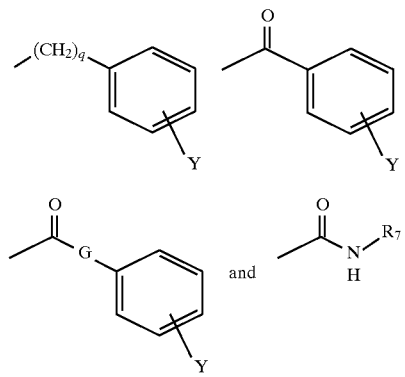

wherein q is 1, 2, 3, or 4;

Y is each time taken from 1 to 3 substituents independently selected from the group consisting of hydrogen, halogen, hydroxy, $C_1$–$C_4$ alkyl, $C_1$–$C_4$ alkoxy, and —OC(O)$R_6$;

G is —NH— or —(CH$_2$)$_r$— wherein r is 1, 2, or 3;

$R_7$ is $C_1$–$C_6$ alkyl;

$R_2$ is hydrogen, $C_1$–$C_4$ alkyl, or the radical

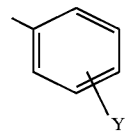

$R_3$ is hydrogen or $C_1$–$C_4$ alkyl;

$R_4$ is hydrogen or $C_1$–$C_4$ alkyl;

$R_5$ is hydrogen, $C_1$–$C_8$ alkyl, or phenyl; or $R_4$ and $R_5$ may be taken together with the adjacent nitrogen to form a ring —CH$_2$—CH$_2$—G$_1$—CH$_2$—CH$_2$ wherein G$_1$ is a direct bond, —NCH$_3$—, —CH$_2$—, or —O—; and $R_6$ is each time taken is independently selected from the group consisting of $C_1$–$C_4$ alkyl, phenyl and substituted phenyl having from 1 to 3 substituents independently selected from the group consisting of hydrogen, halogen, hydroxy, $C_1$–$C_4$ alkyl, or $C_1$–$C_4$ alkoxy;

with the proviso that when n is 1 then at least one $R_1$, $R_2$, $R_3$, $R_4$, and $R_5$ is not hydrogen; and with the additional proviso that when p is 0 and $R_3$ is H, then n is greater than 1; or their pharmaceutically acceptable salts.

2. The compound according to claim 1, wherein Y is from 1 to 3 substituents independently selected from the group consisting of hydrogen, halogen, hydroxy, $C_1$–$C_4$ alkyl, and $C_1$–$C_4$ alkoxy.

3. The compound according to claim 1, wherein Y is —OC(O)$R_6$.

4. The compound according to claim 1, wherein X is hydroxy or —OC(O)$R_6$.

5. The compound according to claim 1, wherein n is an integer from 4 to 8.

6. The compound according to claim 5, wherein n is an integer from 5 to 7.

7. The compound according to claim 1, wherein $R_3$ is hydrogen or methyl.

8. The compound of claim 1 wherein the compound is 8-[[5-Hydroxy-1-benzyl-2-methyl-1H-indol-3-yl]-acetylamino]-octanoic acid methyl-butyl-amide or 8-[[5-Acetoxy-1-benzyl-2-methyl-1H-indol-3-yl]-acetylamino]-octanoic acid methyl-butyl-amide.

9. The compound of claim 1 wherein the compound is 8-[[5-Hydroxy-1-(4-chlorobenzoyl)-2-methyl-1H-indol-3-yl]-acetylamino]-octanoic acid methyl-butyl-amide or 8-[[5-Acetoxy-1-(4-chlorobenzoyl)-2-methyl-1H-indol-3-yl]-acetylamino]-octanoic acid methyl-butyl-amide.

10. The compound of claim 1 wherein the compound is 8-[[5-Hydroxy-1-benzyl-2-[(4-hydroxy)-phenyl]-1H-indol-3-yl]-acetylamino]-octanoic acid methyl-butyl-amide or 8-[[5-Acetoxy-1-benzyl-2-[(4-acetoxy)-phenyl]-1H-indol-3-yl]-acetylamino]-octanoic acid methyl-butyl-amide.

11. The compound of claim 1 wherein the compound is 8-[[5-Hydroxy-1-benzyl-2-[(4-hydroxy)-phenyl]-1H-indol-3-yl]-acetylamino]-octanoic acid butyl-amide or 8-[[5-Acetoxy-1-benzyl-2-[(4-acetoxy)-phenyl]-1H-indol-3-yl]-acetylamino]-octanoic acid butyl-amide.

12. The compound of claim 1 wherein the compound is 8-[[5-Hydroxy-1-benzoyl-2-methyl-1H-indol-3-yl]-acetylamino]-octanoic acid methyl-butyl-amide or 8-[[5-Acetoxy-1-benzoyl-2-methyl-1H-indol-3-yl]-acetylamino]-octanoic acid methyl-butyl-amide.

13. The compound of claim 1 wherein the compound is 6-[[5-Hydroxy-1-benzyl-2-[(4-hydroxy)phenyl]-1H-indol-3-yl]-acetylamino]-hexanoic acid methyl-butyl-amide or 6-[[5-Acetoxy-1-benzyl-2-[(4-acetoxy)phenyl]-1H-indol-3-yl]-acetylamino]-hexanoic acid methyl-butyl-amide.

14. The compound of claim 1 wherein the compound is 8-[[5-Acetoxy-1-benzyl-2-[(4-acetoxy)-phenyl]-1H-indol-3-yl]-acetylamino]-octanoic acid methyl-butyl-amide.

15. The compound of claim 1 wherein the compound is 8-[[1-Benzyl-1H-indol-3-yl]-acetylamino]-octanoic acid methyl-butyl-amide.

16. The compound of claim 1 wherein the compound is 8-[[5-Methoxy-1-(4-chlorobenzoyl)-2-methyl-1H-indol-3-yl]-acetylamino]-octanoic acid diethyl-amide.

17. The compound of claim 1 wherein the compound is 8-[[5-Hydroxy-1-(4-chlorobenzoyl)-2-methyl-1H-indol-3-yl]-acetylamino]-octanoic acid diethyl-amide or 8-[[5-Acetoxy-1-(4-chlorobenzoyl)-2-methyl-1H-indol-3-yl]-acetylamino]-octanoic acid diethyl-amide.

18. The compound of claim 1 wherein the compound is 8-[[5-Methoxy-1-(4-chlorobenzoyl)-2-methyl-1H-indol-3-yl]-acetylamino]-octanoic acid pyrrolidine-amide.

19. The compound of claim 1 wherein the compound is 8-[[5-Hydroxy-1-(4-chlorobenzoyl)-2-methyl-1H-indol-3-yl]-acetylamino]-octanoic acid pyrrolidine-amide or 8-[[5-Acetoxy-1-(4-chlorobenzoyl)-2-methyl-1H-indol-3-yl]-acetylamino]-octanoic acid pyrrolidine-amide.

20. The compound of claim 1 wherein the compound is 8-[[5-Methoxy-1-(4-methoxybenzoyl)-2-methyl-1H-indol-3-yl]-acetylamino]-octanoic acid methyl-butyl-amide.

21. The compound of claim 1 wherein the compound is 8-[[5-Hydroxy-1-(4-methoxybenzoyl)-2-methyl-1H-indol-3-yl]-acetylamino]-octanoic acid methyl-butyl-amide.

22. The compound of claim 1 wherein the compound is 8-[[5-Acetoxy-1-(4-methoxybenzoyl)-2-methyl-1H-indol-3-yl]-acetylamino]-octanoic acid methyl-butyl-amide.

23. The compound of claim 1 wherein the compound is 7-[[5-Methoxy-1-benzoyl-2-methyl-1H-indol-3-yl]-acetylamino]-heptanoic acid methyl-butyl-amide.

24. The compound of claim 1 wherein the compound is 7-[[5-Hydroxy-1-benzoyl-2-methyl-1H-indol-3-yl]-acetylamino]-heptanoic acid methyl-butyl-amide or 7-[[5-Acetoxy-1-benzoyl-2-methyl-1H-indol-3-yl]-acetylamino]-heptanoic acid methyl-butyl-amide.

25. The compound of claim 1 wherein the compound is 7-[[5-Methoxy-1-benzoyl-2-methyl-1H-indol-3-yl]-acetylamino]-heptanoic acid methyl-phenyl-amide.

26. The compound of claim 1 wherein the compound is 7-[[5-Hydroxy-1-benzoyl-2-methyl-1H-indol-3-yl]-acetylamino]-heptanoic acid methyl-phenyl-amide or 7-[[5-Acetoxy-1-benzoyl-2-methyl-1H-indol-3-yl]-acetylamino]-heptanoic acid methyl-phenyl-amide.

27. The compound of claim 1 wherein the compound is 7-[[5-Methoxy-1-benzoyl-2-methyl-1H-indol-3-yl]-acetylamino]-heptanoic acid diethyl-amide.

28. The compound of claim 1 wherein the compound is 7-[[5-Hydroxy-1-benzoyl-2-methyl-1H-indol-3-yl]-acetylamino]-heptanoic acid diethyl-amide.

29. The compound of claim 1 wherein the compound is 7-[[5-Acetoxy-1-benzoyl-2-methyl-1H-indol-3-yl]-acetylamino]-heptanoic acid diethyl-amide.

30. The compound of claim 1 wherein the compound is 7-[[5-fluoro-1-benzoyl-1H-indol-3-yl]-acetylamino]-heptanoic acid diethyl-amide.

31. The compound of claim 1 wherein the compound is 8-[[5-fluoro-1-benzyl-1H-indol-3-yl]-acetylamino]-octanoic acid methyl-butyl-amide.

32. The compound of claim 1 wherein the compound is 8-[[5-Methoxy-1-(3-phenylpropionyl)-2-methyl-1H-indol-3-yl]-acetylamino]-octanoic acid methyl-butyl-amide.

33. The compound of claim 1 wherein the compound is 8-[[5-Hydroxy-1-(3-phenylpropionyl)-2-methyl-1H-indol-3-yl]-acetylamino]-octanoic acid methyl-butyl-amide or 8-[[5-Acetoxy-1-(3-phenylpropionyl)-2-methyl-1H-indol-3-yl]-acetylamino]-octanoic acid methyl-butyl-amide.

34. The compound of claim 1 wherein the compound is 7-[[5-Methoxy-1-(3-phenylpropyl)-2-methyl-1H-indol-3-yl]-acetylamino]-heptanoic acid methyl-butyl-amide.

35. The compound of claim 1 wherein the compound is 7-[[5-Hydroxy-1-(3-phenylpropyl)-2-methyl-1H-indol-3-yl]-acetylamino]-heptanoic acid methyl-butyl-amide.

36. The compound of claim 1 wherein the compound is 7-[[5-Acetoxy-1-(3-phenylpropyl)-2-methyl-1H-indol-3-yl]-acetylamino]-heptanoic acid methyl-butyl-amide.

37. The compound of claim 1 wherein the compound is 8-[[5-Methoxy-1-(4-chlorobenzoyl)-2-methyl-1H-indol-3-yl]-acetylamino]-octanoic acid morpholine-amide.

38. The compound of claim 1 wherein the compound is 8-[[5-Hydroxy-1-(4-chlorobenzoyl)-2-methyl-1H-indol-3-yl]-acetylamino]-octanoic acid morpholine-amide or 8-[[5-Acetoxy-1-(4-chlorobenzoyl)-2-methyl-1H-indol-3-yl]-acetylamino]-octanoic acid morpholine-amide.

39. The compound of claim 1 wherein the compound is 7-[[5-Methoxy-1-benzyl-2-[(4-methoxy)phenyl]-1H-indol-3-yl]-acetylamino]-heptanoic acid methyl butyl-amide.

40. The compound of claim 1 wherein the compound is 7-[[5-Hydroxy-1-benzyl-2-[(4-hydroxy)phenyl]-1H-indol-3-yl]-acetylamino]-heptanoic acid methyl butyl-amide.

41. The compound of claim 1 wherein the compound is 7-[[5-Acetoxy-1-benzyl-2-[(4-acetoxy)phenyl]-1H-indol-3-yl]-acetylamino]-heptanoic acid methyl butyl-amide.

42. The compound of claim 1 wherein the compound is 6-[[5-Methoxy-1-(4-chlorobenzoyl)-2-methyl-1H-indol-3-yl]-acetylamino]-hexanoic acid methyl-butyl-amide.

43. The compound of claim 1 wherein the compound is 6-[[5-Hydroxy-1-(4-chlorobenzoyl)-2-methyl-1H-indol-3-yl]-acetylamino]-hexanoic acid methyl-butyl-amide or 6-[[5-Acetoxy-1-(4-chlorobenzoyl)-2-methyl-1H-indol-3-yl]-acetylamino]-hexanoic acid methyl-butyl-amide.

44. The compound of claim 1 wherein the compound is 8-[[5-Methoxy-1-benzyl-2-(4-fluorophenyl)-1H-indol-3-yl]-acetylamino]-octanoic acid methyl-butyl-amide.

45. The compound of claim 1 wherein the compound is 8-[[5-Hydroxy-1-benzyl-2-(4-fluorophenyl)-1H-indol-3-yl]-acetylamino]-octanoic acid methyl-butyl-amide.

46. The compound of claim 1 wherein the compound is 8-[[5-Acetoxy-1-benzyl-2-(4-fluorophenyl)-1H-indol-3-yl]-acetylamino]-octanoic acid methyl-butyl-amide.

47. The compound of claim 1 wherein the compound is 6-[[5-Methoxy-1-benzyl-2-[(4-methoxy)phenyl]-1H-indol-3-yl]-acetylamino]-hexanoic acid methyl-butyl-amide.

48. The compound of claim 1 wherein the compound is 6-[[5-Hydroxy-1-benzyl-2-[(4-hydroxy)phenyl]-1H-indol-3-yl]-acetylamino]-hexanoic acid methyl-butyl-amide or 6-[[5-Acetoxy-1-benzyl-2-[(4-acetoxy)phenyl]-1H-indol-3-yl]-acetylamino]-hexanoic acid methyl-butyl-amide.

49. The compound of claim 1 wherein the compound is 7-[[5-Methoxy-1-(carboxylic acid 4-methoxyphenyl amide)-1H-indol-3-yl]-acetylamino]-heptanoic acid diethyl-amide.

50. The compound of claim 1 wherein the compound is 7-[[5-Hydroxy-1-(carboxylic acid 4-hydroxyphenyl amide)-1H-indol-3-yl]-acetylamino]-heptanoic acid diethyl-amide or 7-[[5-Acetoxy-1-(carboxylic acid 4-hydroxyphenyl amide)-1H-indol-3-yl]-acetylamino]-heptanoic acid diethyl-amide.

51. The compound of claim 1 wherein the compound is 7-[[5-Methoxy-1-(carboxylic acid 4-chlorophenyl amide)-1H-indol-3-yl]-acetylamino]-heptanoic acid diethyl-amide.

52. The compound of claim 1 wherein the compound is 7-[[5-Hydroxy-1-(carboxylic acid 4-chlorophenyl amide)-1H-indol-3-yl]-acetylamino]-heptanoic acid diethyl-amide or 7-[[5-Acetoxy-1-(carboxylic acid 4-chlorophenyl amide)-1H-indol-3-yl]-acetylamino]-heptanoic acid diethyl-amide.

53. The compound of claim 1 wherein the compound is 7-[[5-Methoxy-1-(carboxylic acid butyl amide)-1H-indol-3-yl]-acetylamino]-heptanoic acid diethyl-amide.

54. The compound of claim 1 wherein the compound is 7-[[5-Hydroxy-1-(carboxylic acid butyl amide)-1H-indol-3-yl]-acetylamino]-heptanoic acid diethyl-amide or 7-[[5-Acetoxy-1-(carboxylic acid butyl amide)-1H-indol-3-yl]-acetylamino]-heptanoic acid diethyl-amide.

55. The compound of claim 1 wherein the compound is 7-[[5-Methoxy-1-(4-butylbenzoyl)-2-methyl-1H-indol-3-yl]-acetylamino]-heptanoic acid diethyl-amide.

56. The compound of claim 1 wherein the compound is 7-[[5-Hydroxy-1-(4-butylbenzoyl)-2-methyl-1H-indol-3-yl]-acetylamino]-heptanoic acid diethyl-amide or 7-[[5-Acetoxy-1-(4-butylbenzoyl)-2-methyl-1H-indol-3-yl]-acetylamino]-heptanoic acid diethyl-amide.

57. The compound of claim 1 wherein the compound is 8-[[5-Methoxy-2-methyl-1H-indol-3-yl]-acetylamino]-octanoic acid methyl-butyl-amide.

58. The compound of claim 1 wherein the compound is 8-[[5-Hydroxy-2-methyl-1H-indol-3-yl]-acetylamino]-octanoic acid methyl-butyl-amide or 8-[[5-Acetoxy-2-methyl-1H-indol-3-yl]-acetylamino]-octanoic acid methyl-butyl-amide.

59. A method for the treatment of a patient afflicted with a neoplastic disease state comprising the administration thereto of a compound according to claim 1.

60. The method according to claim 59, wherein a therapeutically effective antineoplastic amount of a compound is administered.

61. The method according to claim 59, wherein the neoplastic disease state is estrogen-dependent.

62. The method according to claim 59, wherein the neoplastic disease is breast, ovarian, uterine or cervical neoplasia.

63. The method according to claim 62, wherein the neoplastic disease is breast neoplasia.

64. A method for the prophylactic treatment of a patient at risk of developing a neoplastic disease state comprising the administration thereto of a compound according to claim 1.

65. The method according to claim 64, wherein a prophylactically effective antineoplastic amount of a compound is administered.

66. The method according to claim 64, wherein the neoplastic disease state is estrogen-dependent.

67. The method according to claim 64, wherein the neoplastic disease is breast, ovarian, uterine or cervical neoplasia.

68. The method according to claim 64, wherein the neoplastic disease is breast neoplasia.

69. A method for the treatment of a patient afflicted with an autoimmune disease comprising the administration thereto of a compound according to claim 1.

70. The method according to claim 69, wherein the autoimmune disease is estrogen-dependent.

71. A pharmaceutical composition comprising a compound according to claim 1.

72. The pharmaceutical composition according to claim 71, wherein the compound is in admixture with a carrier or excipient.

* * * * *